(12) United States Patent
Virji

(10) Patent No.: US 7,449,302 B2
(45) Date of Patent: Nov. 11, 2008

(54) THERAPEUTIC PEPTIDES

(75) Inventor: Mumtaz Virji, Bristol (GB)

(73) Assignee: The University of Bristol, University Walk, Bristol (GB)

( * ) Notice: Subject to any disclaimer, the term of this patent is extended or adjusted under 35 U.S.C. 154(b) by 41 days.

(21) Appl. No.: 11/097,749

(22) Filed: Apr. 1, 2005

(65) Prior Publication Data

US 2005/0267028 A1 Dec. 1, 2005

Related U.S. Application Data

(63) Continuation-in-part of application No. PCT/GB03/04273, filed on Oct. 1, 2003.

(30) Foreign Application Priority Data

| Oct. 2, 2002 | (GB) | ................................. | 0222764.3 |
| Apr. 15, 2004 | (GB) | ................................. | 0408390.3 |
| Sep. 3, 2004 | (GB) | ................................. | 0419594.7 |

(51) Int. Cl.
  G01N 33/53 (2006.01)
  A61K 38/04 (2006.01)
(52) U.S. Cl. ........................................ 435/7.1; 530/324
(58) Field of Classification Search ...................... None
  See application file for complete search history.

(56) References Cited

FOREIGN PATENT DOCUMENTS

WO   WO 98/28333   7/1998

OTHER PUBLICATIONS

Philippe N'Guessan; The USPA1 protein of *M. catarrhalis* induces CEAMA-1 dependent apoptosis in alverolar epithelial cells. Inflamm. Res. Supp(2), S74, A13, 2007.*

Database EMBL, Sequence of UspA1, retrieved from EBI, Database accession No. Q9XD56, XP002273230 (1999).

Hill et al., "A novel-cell-binding mechanism of *Moraxella catarrhalis* ubiquitous surface protein UspA: specific targeting of the N-domain of carcinoembryonic antigen-related cell adhesion molecules by uspA1", Molecular Micrbiology 48(1):117-129 (2003).

Lafontaine et al., "The UspA1 Protein and a Second Type of UspA2 Protein Mediate Adherence of *Moraxella catarrhalis* to Human Epithelial Cells In Vitro", Journal of Bacteriology, 182(5):1364-1373 (2000).

Meier et al., "The outer membrane proteins UspA1 and UspA2 of *Moraxella catarrhalis* are highly conserved in nasopharyngeal isolates from young children", Vaccine 20:1754-1760 (2002).

Chen et al., "Evaluation of Purified UspA from *Moraxella catarrhalis* as a Vaccine in a Murine Model after Active Immunization", Infection and Immunity 64(6):1900-1905 (1996).

Virji et al., "Carcinoembryonic antigens are targeted by diverse strains of typable and non-typable *Haemophilus influenzae*", Molecular Microbiology, 36(4):784-795 (2000).

Virji et al., "Critical determinants of host receptor targeting by *Neisseria meningitides* and *Neisseria gonorrhoeae*: identification of Opa adhesiotopes on the N-domain of CD66 molecules", Molecular Microbiology, 34(3):538-551 (1999).

Hill et al., "Carcinoembroyonic antigen-related cell adhesion molecule (CEACAM)-binding recombinant polypeptide confers protection against infection by respiratory and urogenital pathogens", Molecular Microbiology, 55(5):1515-1527 (2005).

\* cited by examiner

*Primary Examiner*—Maher M Haddad
(74) *Attorney, Agent, or Firm*—Edwards Angell Palmer & Dodge LLP; Peter C. Lauro; Melissa Hunter-Endsor

(57) ABSTRACT

The present invention provides a ligand isolated from *Moraxella catarrhalis* outer membrane protein which binds to CEACAM receptors, said ligand comprising a receptor binding domain comprising an amino acid sequence selected from the group disclosed, or a fragment, homologue, functional equivalent, derivative, degenerate or hydroxylation, sulphonation or glycosylation product or other secondary processing product thereof. The invention also provides medicaments and vaccines comprising said ligand, and their use in the treatment or prophylaxis of infection. Also provided is a screening method for the identification of novel therapeutic compounds.

4 Claims, 31 Drawing Sheets

| Input Summary | |
|---|---|
| Date & Time | Thu Aug 02 11:55:23 2001 UTC (Search Time: 17.38 sec.) |
| Sample ID | 11020EE20-7-01 |
| Database | NCBInr (2001/07/29) |
| Taxonomy Category | All-taxa |
| Protein Mass Range | 80 - 100 kDa |
| Protein pI Range | 0.0 - 14.0 |
| Search for | Single protein only |
| Digest Chemistry | Trypsin |
| Max Missed Cut | 1 |
| Modifications | None |
| Charge State | MH+ |
| Peptide Masses (Da,Average) | |
| Tolerance(AVG) | 1.00 ppm |
| Peptide Masses (Da,Monoisotopic) | 679.514 684.348 842.510 897.421 1036.535 1126.566 1157.592 1179.598 1277.702 1300.538 1302.633 1306.630 1307.681 1311.689 1379.718 1383.708 1415.714 1424.752 1434.769 1438.723 1440.774 1458.736 1474.731 1475.757 1637.850 1638.859 1648.850 1657.807 1700.854 1701.869 1707.781 1715.823 1716.858 1731.876 1757.875 1794.809 1807.903 1826.798 1837.968 1851.920 1890.972 1895.922 1909.054 1922.930 1927.947 1940.931 1955.978 1987.056 1993.976 2016.988 2064.139 2081.967 2087.974 2150.075 2184.140 2211.104 2221.129 2225.129 2230.218 2239.136 2261.122 2283.164 2297.197 2299.182 2383.981 2399.049 2408.087 2564.193 2663.346 2705.179 2717.129 2720.281 2748.314 2781.924 2791.004 2792.915 2805.359 2807.327 2825.331 2872.402 2914.526 2921.383 |
| Tolerance(MON) | 20.00 ppm |
| Number of Peptides | 82 |

Figure 4b

ProFound - Search Result Summary

Version 4.10.5
The Rockefeller University Edition

Protein Candidates for search C2BABE89-01DC-745F3E9 [731183 sequences searched]

| Rank | Probability | Est'd Z | Protein Information and Sequence Analyse Tools (T) | % | pI | kDa |
|---|---|---|---|---|---|---|
| +1 | 1.0e+000 | 2.34 | T gi|5453174|gb|AAD43465.1|AF113606_1 (AF113606) UspA1 [Moraxella catarrhalis] | 18 | 5.7 | 90.52 |
|  |  |  | T gi|7208237|gb|AAF40122.1|AF181076_1 (AF181076) USPA1 [Moraxella catarrhalis] | 14 | 5.4 | 91.86 |
|  |  |  | T gi|5453178|gb|AAD43467.1|AF113608_1 (AF113608) UspA1 [Moraxella catarrhalis] | 15 | 5.7 | 99.06 |
|  |  |  | T gi|5453182|gb|AAD43469.1|AF113610_1 (AF113610) UspA1 [Moraxella catarrhalis] | 13 | 5.3 | 95.75 |
|  |  |  | T gi|7208229|gb|AAF40118.1|AF181072_1 (AF181072) USPA1 [Moraxella catarrhalis] | 11 | 5.6 | 96.95 |
|  |  |  | T gi|8572547|gb|AAB96359.21 (U57551) high molecular weight outer membrane protein [Moraxella catarrhalis] | 8 | 4.9 | 88.27 |
| 2 | 1.6e-011 |  | T gi|2128720|pir||E64449 hypothetical protein MJ1198 - Methanococcus jannaschii | 8 | 5.6 | 85.92 |
| 3 | 1.3e-012 |  | T gi|7108403|gb|AAF36416.1|U61725_1 (U61725) USPA1 [Moraxella catarrhalis] | 13 | 5.7 | 93.34 |
| 4 | 9.5e-013 |  | T gi|13366277|emb|CAB51587.2| (AL031687) dJ998H6.1 (ortholog of rat PB-Cadherin) [Homo sapiens] | 12 | 4.6 | 89.07 |
| 5 | 7.9e-013 |  | T gi|1127080|sp|rl|H81749 DNA topoisomerase I TC0012 [imported] - Chlamydia muridarum (strain Nigg) | 10 | 9.2 | 97.92 |
| 6 | 5.4e-013 |  | T gi|9629643|ref|NP_044927.1| capsid [adeno-associated virus 4] | 11 | 6.1 | 80.62 |
| 7 | 4.9e-013 |  | T gi|7497065|pir||T15778 hypothetical protein C35B8.2 - Caenorhabditis elegans | 9 | 6.0 | 97.36 |
| 8 | 4.3e-013 |  | T gi|14009690|gb|AAK51717.1| (AF348175) PA protein [Influenza A virus (A/Hong Kong/1/68(H3N2))] | 9 | 5.3 | 82.91 |
| 9 | 3.0e-013 |  | T gi|14973264|gb|AAK75842.1| (AE007469) glycosyl transferase, family 8 [Streptococcus pneumoniae] | 9 | 5.2 | 94.60 |
| 10 | 1.2e-013 |  | T gi|13423336|gb|AAK23864.1| (AE005862) ribonucleotide reductase-related protein [Caulobacter crescentus] | 10 | 5.1 | 98.47 |

Figure 4c

¹MNKIYKVKKNAAGHLVACSEFAKGHTKKAVLGSLLIVGILGMATTASAQKVGKATNKISGGDNNTANGTYLTIGGGDY ⁷⁸

⁷⁹NKTKGRYSTIGGGLFNEATNEYSTIGSGGYNKAKGRYSTIGGGGYNEATNQYSTIGGGDNNTAKGRYSTIGGGGYNEATI¹⁵⁸

¹⁵⁹ENSTVGGGGYNQAKGRNSTVAGGYNNEATGTDSTIAGGRKNQATGKGSFAAGIDNKANADNAVALGNKNTIEGENSVA²³⁶

²³⁷IGSNNTVKKGQQNVFILGSNTDTTNAQNGSVLLGHNTAGKAATIVNSAEVGGLSLTGFAGASKTGNGTVSVGKKGKERQI³¹⁶

³¹⁷VHVGAGEISDTSTDAVNGSQLHALATVVAQNKADIKDLDDEVGLLGEEINSLEGEIFNNQDAIAKNQADIKTLESNVEEG³⁹⁶

³⁹⁷LLDLSGRLLDQKADIDNNINNIYELAQQQDQHSSDIKTLKNNVEEGLLDLSGRLIDQKADLTKDIKALESNVEEGLLDLSGRLI⁴⁸⁰

⁴⁸¹DQKADIAKNQADIAQNQTDIQDLAAYNELQDAYAKQQTEAIDALNKASSANTDRIATAELGIAENKKDAQIAKAQANEN⁵⁵⁹

⁵⁶⁰KDGIAKNQADIQLHDKKITNLGILHSMVARAVGNNTQGVATNKADIAKNQADIANNIKNIYELAQQQDQHSSDIKTLAK⁶³⁸

⁶³⁹VSAANTDRIAKNKAEADASFETLTKNQNTLIEQGEALVEQNKAINQELEGFAAHADVQDKQILQNQADITTNKTAIEQNIN⁷¹⁹

⁷²⁰RTVANGFEIEKNKAGIATNKQELILQNDRLNRINETNNHQDQKIDQLGYNLKEQGQHFNNRISAVERQTAGGIANAIAIATL⁸⁰¹

⁸⁰²PSPSRAGEHHVLFGSGYHNGQAAVSLGAAGLSDTGKSTYKIGLSWSDAGGLSGGVGGSYRWK⁸⁶³

Figure 6

⁴⁶³ALESHVEEGLLDLSGRLI⁴⁸⁰

⁴⁸¹DQKADIAKNQADIAQNQTDIQDLAAYNELQDAYAKQQTEAIDALNKASSANTDRIATAELGIAENKKDAQIAKAQANEN⁵⁵⁹

⁵⁶⁰KDGIAKNQADIQLHDKKITNLGILHSMVARAVGNNTQGVATNKADIAKNQADIANNIKNIYELAQQQDQHSSDIKTLAK⁶³⁸

⁶³⁹VSAANTDRIAKNKAEADASFETLTKNQNTLIEQGEALVEQNKAINQELEGFAAHADVQDKQILQNQADITTNKTAIEQNIN⁷¹⁹

⁷²⁰RTVANGFEIEKNKAGIATMKQELILQMDRLNRINETNNHQDQKIDQLGYALKEQGQHFNNRISAVERQTAGGIANAIAIATL⁸⁰¹

⁸⁰²PSPSRAGEHHVLFGSGYHNGQAAVSLGAAGLSDTGKSTYKIGLSWSDAGGLSGGVGGSYRWK⁸⁶³

Figure 8

$^{427}$qhssdiktlknnveeglldlsgrlidqkadltkdikalesnveeglldlsgrli$^{480}$ $^{481}$dqkadiaknqadiaqnqtdiqdlaaynelqdayakqqteaidalnkassantdriataelgiaenkkdaqiakaqanen$^{559}$ $^{560}$kdgiaknqadiqlhdkkitnlgilhsmvaravgnntqgvatnkadiaknqadiannikniyelaqqqdqhssdiktlak$^{638}$ $^{639}$vsaantdriaknkaeadasfetltknqntl$^{668}$       ↑T

<u>33-mer:</u>
   a ntdriatael giaenkkdaq iakaqanen<u>k</u> dg
<u>47-mer:</u>
                                     en<u>k</u>dgiaknqadiqlhdkkitnlgilhsmvaravgnntqgvatnkad
<u>30-mer:</u>
                   kdaq iakaqanen<u>k</u> dgiaknqadi qlhdkk
<u>Overlapping peptides:</u>
                        q iakaqanen<u>k</u> dgiaknqad
                            <u>k</u> dgiaknqadi qlhdkkitn
                                  i qlhdkkitnl gilhsmvar
                                        l gilhsmvara vgnntqgva
                                              a vgnntqgvat nkadiaknq
                                                      t
                                               nkadiaknqa diannikni <u>other non-binders:</u>        nk dgi
                             en<u>k</u> dgia

Figure 20

```
    ASSANTDRIATAELGIAENKKDAQIAKAQANENKDGIAKNQADIQLHDKK    Majority

1 ASSANTDRIATAELGIAENKKDAQIAKAQANENKDGIAKNQADIQLHDKK           TTA24D-7
  1 ASSANTDRIATAELGIAENKKDAQIAKAQANENKDGIAK----------------     TTA37D-7
  1 ASSANTDRIATAELGIAENKKDAQIAKAQANENKDGIAKNQADIQLHDKK    p44D-7
  1 ASSANTDRIATAELGIAENKKDAQIAKAQANENKDGIAKNQADIQLHDKK    O12ED-7
  1 --------------------------ASSENTQNIAK-------------------------------    O35ED-7
  1 ASSANTDRIATAELGIAENKKDAQIAKAQANENKDGIAKNQADIQLHDKK    O46ED-7
  1 ASSANTDRIATAELGIAENKKDAQIAKAQANENKDGIAKNQADIQLHDKK    MX2D-7
  1 ASSANTDRIATAELGIAENKKDAQIAKAQANENKDGIAKNQADIQLHDKK    V1171D-7
  1 -------------------LGIAENKKDAQIAKAQANENKDGIAKNQADIQLHDKK    MX3D-7
  1 ------------------- -------ENKKDAQIAKAQANENKDGIAKNQADIQLHDKK    MX4D-7

ITNLGILHSMVARAVGNNTQGVATNKADIAKNQADIANNIKNIYELAQQQ    Majority

51 ITNLGILHSMVARAVGNNTQGVATNKADIAKNQADIANNIKNIYELAQQQ    TTA24D-7
 40 ----------------------------- ------ -----------NQADIANNIKNIYELAQQQ    TTA37D-7
 51 ITNLGILHSMVARAVGNNTQGVATNKADIAKNQADIANNIKNIYELAQQQ    p44D-7
 51 ITNLGILHSMVARAVGNNTQGVATNKADIAKNQADIANNIKNIYELAQQQ    O12ED-7
 12 ------------------- -------------------------NQADIANNINNIKNIYELAQQQ    O35ED-7
 51 ITNLGILHSMVARAVGNNTQGVATNKADIAKNQADIANNIKNIYELAQQQ    O46ED-7
 51 ITNLGILHSMVARAVGNNTQGVATNKADIAKNQADIANNIKNIYELAQQQ    MX2D-7
 51 ITNLGILHSMVARAVGNNTQGVATNKADIAKNQADIANNIKNIYELAQQQ    V1171D-7
 38 ITNLGILHSMVARAVGNNTQGVATNKADIAKNQADIANNIKNIYELAQQQ    MX3D-7
 34 ITNLGILHSMVARAVGNNTQGVATNKADIAKNQADIANNIKNIYELAQQQ    MX4D-7

DQHSSDIKTLAKVSAANTDRIAKNKAEADASFETLTKNQNTL            Majority

101 DQHSSDIKTLAKVSAANTDRIAKNKAEADASFETLTKNQNTL            TTA24D-7
 59 DQHSSDIKTLAKVSAANTDRIAKNKAEADASFETLTKNQNTL            TTA37D-7
101 DQHSSDIKTLAKVSAANTDRIAKNKAEADASFETLTKNQNTL            p44D-7
101 DQHSSDIKTLAKVSAANTDRIAKNKAEADASFETLTKNQNTL            O12ED-7
 31 DQHSSDIKTLAKVSAANTDRIAKNKAEADASFETLTKNQNTL            O35ED-7
101 DQHSSDIKTLAKVSAANTDRIAKNKAEADASFETLTKNQNTL            46ED-7
101 DQHSSDIKTLAKVSAANTDRIAKNKAEADASFETLTKNQNTL            MX2D-7
101 DQHSSDIKTLAKVSAANTDRIAKNKAEADASFETLTKNQNTL            V1171D-7
 88 DQHSSDIKTLAKVSAANTDRIAKNKAEADASFETLTKNQNTL            MX3D-7
 84 DQHSSDIKTLAKVSAANTDRIAKNKAEADASFETLTKNQNTL            MX4D-7
```

Figure 21

ASSANTDRIATAELGIAENKKDAQIAKAQANENKDGIAKN Majority

1 ASSANTDRIATAELGIAENKKDAQIAKAQANENKDGIAKN MX2D-7
1 ASS--------------------EN--------------------------------- O35ED-7

QADIQLHDKKITNLGILHSMVARAVGNNTQGVATNKADIA Majority

41 QADIQLHDKKITNLGILHSMVARAVGNNTQGVATNKADIA MX2D-7
 6 ----------------------------------------TQ------N----IA O35ED-7

KNQADIANNINNIYELAQQQDQHSSDIKTLAKVSAANTDR Majority

81 KNQADIANNIKNIYELAQQQDQHSSDIKTLAKVSAANTDR MX2D-7
11 KNQADIANNINNIYELAQQQDQHSSDIKTLAKVSAANTDR O35ED-7

IAKNKAEADASFETLTKNQNTL              Majority

121 IAKNKAEADASFETLTKNQNTL              MX2D-7
 51 IAKNKAEADASFETLTKNQNTL              O35ED-7

Figure 22

Pair Distances of D-7align.meg ClustalW (Slow/Accurate, Gonnet)

Percent Similarity in upper triangle
Percent Divergence in lower triangle

|  | 1) | 2) | 3) | 4) | 5) | 6) | 7) | 8) | 9) | 10) |  |
|---|---|---|---|---|---|---|---|---|---|---|---|
| 1) TTA24D-7 | *** | 100.0 | 100.0 | 100.0 | 88.9 | 100.0 | 100.0 | 100.0 | 100.0 | 100.0 | 1) TTA24D-7 |
| 2) TTA37D-7 | 0.0 | *** | 100.0 | 100.0 | 90.3 | 100.0 | 100.0 | 100.0 | 87.0 | 83.0 | 2) TTA37D-7 |
| 3) P44D-7 | 0.0 | 0.0 | *** | 100.0 | 88.9 | 100.0 | 100.0 | 100.0 | 100.0 | 100.0 | 3) P44D-7 |
| 4) O12ED-7 | 0.0 | 0.0 | 0.0 | *** | 88.9 | 100.0 | 100.0 | 100.0 | 100.0 | 100.0 | 4) O12ED-7 |
| 5) O35ED-7 | 10.4 | 10.4 | 10.4 | 10.4 | *** | 88.9 | 88.9 | 88.9 | 88.9 | 88.9 | 5) O35ED-7 |
| 6) O46ED-7 | 0.0 | 0.0 | 0.0 | 0.0 | 10.4 | *** | 100.0 | 100.0 | 100.0 | 100.0 | 6) O46ED-7 |
| 7) MX2D-7 | 0.0 | 0.0 | 0.0 | 0.0 | 10.4 | 0.0 | *** | 100.0 | 100.0 | 100.0 | 7) MX2D-7 |
| 8) V1171D-7 | 0.0 | 0.0 | 0.0 | 0.0 | 10.4 | 0.0 | 0.0 | *** | 100.0 | 100.0 | 8) V1171D-7 |
| 9) MX3D-7 | 0.0 | 0.0 | 0.0 | 0.0 | 10.4 | 0.0 | 0.0 | 0.0 | *** | 100.0 | 9) MX3D-7 |
| 10)MX4D-7 | 0.0 | 0.0 | 0.0 | 0.0 | 10.4 | 0.0 | 0.0 | 0.0 | 0.0 | *** | 10)MX4D-7 |
|  | 1) | 2) | 3) | 4) | 5) | 6) | 7) | 8) | 9) | 10) |  |

```
                    *         20         *         40         *
ATCC25238_  : QHSSDIKTLKNNVEEGLLDLSGRLIDQKADLTKDIKALESNVEEGLLDLS  :  50
P44_frag    : QHSSDIKTLKNNVEEGLLDLSGRLIDQKADLTKDIKALENNVEEGLLDLS  :  50
TTA37_frag  : QHSSDIKTLKNNVEEGLLDLSGRLIDQKADLTKDIKALENNVEEGLLDLS  :  50
V1171_frag  : QHSSDIKTLKNNVEEGLLDLSGRLIDQKADLTKDIKTLESNVEEGLLDLS  :  50
O46E_frag   : QHSSDIKTLKKNVEEGLLDLSGRLIDQKADLTKDIKTLENNVEEGLLDLS  :  50
TTA24_frag  : QHSSDIKTLKNNVEEGLLDLSGRLIDQKADLTKDIKTLKNNVEEGLLDLS  :  50
O12E_frag   : QHSSDIKTLKN---------------------------NVEEGLLDLS  :  21
O35E_frag   : QHSSDIKTLKN---------------------------NVEEGLLDLS  :  21

60         *         80         *        100
ATCC25238_  : GRLIDQKADIAKNQADIAQNQTDIQDLAAYNELQDAYAKQQTEAIDALNK  : 100
P44_frag    : GRLIDQKADIAKNQADIAQNQTDIQDLAAYNELQDAYAKQQTEAIDALNK  : 100
TTA37_frag  : GRLIDQKADIAKNQA-------DIQDLAAYNELQDQYAQKQTEAIDALNK  :  93
V1171_frag  : GRLIDQKADIAKNQADIAQNQTDIQDLAAYNELQDQYAQKQTEAIDALNK  : 100
O46E_frag   : GRLIDQKADIAKNQADIAQNQTDIQDLAAYNELQDQYAQKQTEAIDALNK  : 100
TTA24_frag  : GRLIDQKADIAKNQADIAQNQTDIQDLAAYNELQDQYAQKQTEAIDALNK  : 100
O12E_frag   : GRLIDQKADIAKNQADIAQNQTDIQDLAAYNELQDAYAKQQTEAIDALNK  :  71
O35E_frag   : GRLIDQKADIAKNQADIAQNQTDIQDLAAYNELQDQYAQKQTEAIDALNK  :  71

*        120         *        140         *
ATCC25238_  : ASSANTDRIATAELGIAENKKDAQIAKAQANENKDGIAKNQADIQLHDKK  : 150
P44_frag    : ASSANTDRIATAELGIAENKKDAQIAKAQANENKDGIAKNQADIQLHDKK  : 150
TTA37_frag  : ASSANTDRIATAELGIAENKKDAQIAKAQANENKDGIAK----------  : 132
V1171_frag  : ASSANTDRIATAELGIAENKKDAQIAKAQANENKDGIAKNQADIQLHDKK  : 150
O46E_frag   : ASSANTDRIATAELGIAENKKDAQIAKAQANENKDGIAKNQADIQLHDKK  : 150
TTA24_frag  : ASSANTDRIATAELGIAENKKDAQIAKAQANENKDGIAKNQADIQLHDKK  : 150
O12E_frag   : ASSANTDRIATAELGIAENKKDAQIAKAQANENKDGIAKNQADIQLHDKK  : 121
O35E_frag   : ASSENTQNIA---------------------------------------  :  81

160         *        180         *
ATCC25238_  : ITNLGILHSMVARAVGNNTQGVATNKADIAKNQADIANNIKNIYELA  : 197
P44_frag    : ITNLGILHSMVARAVGNNTQGVATNKADIAKNQADIANNIKNIYELA  : 197
TTA37_frag  : -------------------------------NQADIANNIKNIYELA  : 148
V1171_frag  : ITNLGILHSMVARAVGNNTQGVATNKADIAKNQADIANNIKNIYELA  : 197
O46E_frag   : ITNLGILHSMVARAVGNNTQGVATNKADIAKNQADIANNIKNIYELA  : 197
TTA24_frag  : ITNLGILHSMVARAVGNNTQGVATNKADIAKNQADIANNIKNIYELA  : 197
O12E_frag   : ITNLGILHSMVARAVGNNTQGVATNKADIAKNQADIANNIKNIYELA  : 168
O35E_frag   : ------------------------------KNQADIANNINNIYELA  :  98
```

Figure 28

SEQUENCE LISTING

```
<160> NUMBER OF SEQ ID NOS: 60

<210> SEQ ID NO 1
<211> LENGTH: 27
<212> TYPE: PRT
<213> ORGANISM: Moraxella catarrhalis
<220> FEATURE:
<221> NAME/KEY: MOD_RES
<222> LOCATION: (5)
<223> OTHER INFORMATION: His or Arg

<400> SEQUENCE: 1

Glu Thr Asn Asn Xaa Gln Asp Gln Lys Ile Asp Gln Leu Gly Tyr Ala
 1               5                  10                  15

Leu Lys Glu Gln Gly Gln His Phe Asn Asn Arg
            20                  25

<210> SEQ ID NO 2
<211> LENGTH: 863
<212> TYPE: PRT
<213> ORGANISM: Moraxella catarrhalis

<400> SEQUENCE: 2

Met Asn Lys Ile Tyr Lys Val Lys Lys Asn Ala Ala Gly His Leu Val
 1               5                  10                  15

Ala Cys Ser Glu Phe Ala Lys Gly His Thr Lys Lys Ala Val Leu Gly
```

-continued

```
                20                  25                  30
Ser Leu Leu Ile Val Gly Ile Leu Gly Met Ala Thr Thr Ala Ser Ala
         35                  40                  45
Gln Lys Val Gly Lys Ala Thr Asn Lys Ile Ser Gly Gly Asp Asn Asn
     50                  55                  60
Thr Ala Asn Gly Thr Tyr Leu Thr Ile Gly Gly Asp Tyr Asn Lys
 65                  70                  75                  80
Thr Lys Gly Arg Tyr Ser Thr Ile Gly Gly Leu Phe Asn Glu Ala
                 85                  90                  95
Thr Asn Glu Tyr Ser Thr Ile Gly Ser Gly Gly Tyr Asn Lys Ala Lys
             100                 105                 110
Gly Arg Tyr Ser Thr Ile Gly Gly Gly Tyr Asn Glu Ala Thr Asn
         115                 120                 125
Gln Tyr Ser Thr Ile Gly Gly Gly Asp Asn Asn Thr Ala Lys Gly Arg
     130                 135                 140
Tyr Ser Thr Ile Gly Gly Gly Gly Tyr Asn Glu Ala Thr Ile Glu Asn
145                 150                 155                 160
Ser Thr Val Gly Gly Gly Gly Tyr Asn Gln Ala Lys Gly Arg Asn Ser
                 165                 170                 175
Thr Val Ala Gly Gly Tyr Asn Asn Glu Ala Thr Gly Thr Asp Ser Thr
             180                 185                 190
Ile Ala Gly Gly Arg Lys Asn Gln Ala Thr Gly Lys Gly Ser Phe Ala
         195                 200                 205
Ala Gly Ile Asp Asn Lys Ala Asn Ala Asp Asn Ala Val Ala Leu Gly
     210                 215                 220
Asn Lys Asn Thr Ile Glu Gly Glu Asn Ser Val Ala Ile Gly Ser Asn
225                 230                 235                 240
Asn Thr Val Lys Lys Gly Gln Gln Asn Val Phe Ile Leu Gly Ser Asn
                 245                 250                 255
Thr Asp Thr Thr Asn Ala Gln Asn Gly Ser Val Leu Leu Gly His Asn
             260                 265                 270
Thr Ala Gly Lys Ala Ala Thr Ile Val Asn Ser Ala Glu Val Gly Gly
         275                 280                 285
Leu Ser Leu Thr Gly Phe Ala Gly Ala Ser Lys Thr Gly Asn Gly Thr
     290                 295                 300
Val Ser Val Gly Lys Lys Gly Lys Glu Arg Gln Ile Val His Val Gly
305                 310                 315                 320
Ala Gly Glu Ile Ser Asp Thr Ser Thr Asp Ala Val Asn Gly Ser Gln
                 325                 330                 335
Leu His Ala Leu Ala Thr Val Val Ala Gln Asn Lys Ala Asp Ile Lys
             340                 345                 350
Asp Leu Asp Asp Glu Val Gly Leu Leu Gly Glu Glu Ile Asn Ser Leu
         355                 360                 365
Glu Gly Glu Ile Phe Asn Asn Gln Asp Ala Ile Ala Lys Asn Gln Ala
     370                 375                 380
Asp Ile Lys Thr Leu Glu Ser Asn Val Glu Glu Gly Leu Leu Asp Leu
385                 390                 395                 400
Ser Gly Arg Leu Ile Asp Gln Lys Ala Asp Ile Asp Asn Asn Ile Asn
                 405                 410                 415
Asn Ile Tyr Glu Leu Ala Gln Gln Gln Asp Gln His Ser Ser Asp Ile
             420                 425                 430
Lys Thr Leu Lys Asn Asn Val Glu Glu Gly Leu Leu Asp Leu Ser Gly
         435                 440                 445
```

-continued

```
Arg Leu Ile Asp Gln Lys Ala Asp Leu Thr Lys Asp Ile Lys Ala Leu
    450                 455                 460
Glu Ser Asn Val Glu Glu Gly Leu Leu Asp Leu Ser Gly Arg Leu Ile
465                 470                 475                 480
Asp Gln Lys Ala Asp Ile Ala Lys Asn Gln Ala Asp Ile Ala Gln Asn
                485                 490                 495
Gln Thr Asp Ile Gln Asp Leu Ala Ala Tyr Asn Glu Leu Gln Asp Ala
            500                 505                 510
Tyr Ala Lys Gln Gln Thr Glu Ala Ile Asp Ala Leu Asn Lys Ala Ser
        515                 520                 525
Ser Ala Asn Thr Asp Arg Ile Ala Thr Ala Glu Leu Gly Ile Ala Glu
    530                 535                 540
Asn Lys Lys Asp Ala Gln Ile Ala Lys Ala Gln Ala Asn Glu Asn Lys
545                 550                 555                 560
Asp Gly Ile Ala Lys Asn Gln Ala Asp Ile Gln Leu His Asp Lys Lys
                565                 570                 575
Ile Thr Asn Leu Gly Ile Leu His Ser Met Val Ala Arg Ala Val Gly
            580                 585                 590
Asn Asn Thr Gln Gly Val Ala Thr Asn Lys Ala Asp Ile Ala Lys Asn
        595                 600                 605
Gln Ala Asp Ile Ala Asn Asn Ile Lys Asn Ile Tyr Glu Leu Ala Gln
    610                 615                 620
Gln Gln Asp Gln His Ser Ser Asp Ile Lys Thr Leu Ala Lys Val Ser
625                 630                 635                 640
Ala Ala Asn Thr Asp Arg Ile Ala Lys Asn Lys Ala Glu Ala Asp Ala
                645                 650                 655
Ser Phe Glu Thr Leu Thr Lys Asn Gln Asn Thr Leu Ile Glu Gln Gly
            660                 665                 670
Glu Ala Leu Val Glu Gln Asn Lys Ala Ile Asn Gln Glu Leu Glu Gly
        675                 680                 685
Phe Ala Ala His Ala Asp Val Gln Asp Lys Gln Ile Leu Gln Asn Gln
    690                 695                 700
Ala Asp Ile Thr Thr Asn Lys Thr Ala Ile Glu Gln Asn Ile Asn Arg
705                 710                 715                 720
Thr Val Ala Asn Gly Phe Glu Ile Glu Lys Asn Lys Ala Gly Ile Ala
                725                 730                 735
Thr Asn Lys Gln Glu Leu Ile Leu Gln Asn Asp Arg Leu Asn Arg Ile
            740                 745                 750
Asn Glu Thr Asn Asn His Gln Asp Gln Lys Ile Asp Gln Leu Gly Tyr
        755                 760                 765
Ala Leu Lys Glu Gln Gly Gln His Phe Asn Asn Arg Ile Ser Ala Val
    770                 775                 780
Glu Arg Gln Thr Ala Gly Gly Ile Ala Asn Ala Ile Ala Ile Ala Thr
785                 790                 795                 800
Leu Pro Ser Pro Ser Arg Ala Gly Glu His His Val Leu Phe Gly Ser
                805                 810                 815
Gly Tyr His Asn Gly Gln Ala Ala Val Ser Leu Gly Ala Ala Gly Leu
            820                 825                 830
Ser Asp Thr Gly Lys Ser Thr Tyr Lys Ile Gly Leu Ser Trp Ser Asp
        835                 840                 845
Ala Gly Gly Leu Ser Gly Gly Val Gly Gly Ser Tyr Arg Trp Lys
    850                 855                 860
```

<210> SEQ ID NO 3
<211> LENGTH: 401
<212> TYPE: PRT
<213> ORGANISM: Moraxella catarrhalis

<400> SEQUENCE: 3

```
Ala Leu Glu Ser Asn Val Glu Gly Leu Leu Asp Leu Ser Gly Arg
 1               5                  10                  15

Leu Ile Asp Gln Lys Ala Asp Ile Ala Lys Asn Gln Ala Asp Ile Ala
                 20                  25                  30

Gln Asn Gln Thr Asp Ile Gln Asp Leu Ala Ala Tyr Asn Glu Leu Gln
             35                  40                  45

Asp Ala Tyr Ala Lys Gln Gln Thr Glu Ala Ile Asp Ala Leu Asn Lys
     50                  55                  60

Ala Ser Ser Ala Asn Thr Asp Arg Ile Ala Thr Ala Glu Leu Gly Ile
 65                  70                  75                  80

Ala Glu Asn Lys Lys Asp Ala Gln Ile Ala Lys Ala Gln Ala Asn Glu
                 85                  90                  95

Asn Lys Asp Gly Ile Ala Lys Asn Gln Ala Asp Ile Gln Leu His Asp
            100                 105                 110

Lys Lys Ile Thr Asn Leu Gly Ile Leu His Ser Met Val Ala Arg Ala
            115                 120                 125

Val Gly Asn Asn Thr Gln Gly Val Ala Thr Asn Lys Ala Asp Ile Ala
            130                 135                 140

Lys Asn Gln Ala Asp Ile Ala Asn Asn Ile Lys Asn Ile Tyr Glu Leu
145                 150                 155                 160

Ala Gln Gln Gln Asp Gln His Ser Ser Asp Ile Lys Thr Leu Ala Lys
                165                 170                 175

Val Ser Ala Ala Asn Thr Asp Arg Ile Ala Lys Asn Lys Ala Glu Ala
            180                 185                 190

Asp Ala Ser Phe Glu Thr Leu Thr Lys Asn Gln Asn Thr Leu Ile Glu
            195                 200                 205

Gln Gly Glu Ala Leu Val Glu Gln Asn Lys Ala Ile Asn Gln Glu Leu
        210                 215                 220

Glu Gly Phe Ala Ala His Ala Asp Val Gln Asp Lys Gln Ile Leu Gln
225                 230                 235                 240

Asn Gln Ala Asp Ile Thr Thr Asn Lys Thr Ala Ile Glu Gln Asn Ile
                245                 250                 255

Asn Arg Thr Val Ala Asn Gly Phe Glu Ile Glu Lys Asn Lys Ala Gly
            260                 265                 270

Ile Ala Thr Asn Lys Gln Glu Leu Ile Leu Gln Asn Asp Arg Leu Asn
            275                 280                 285

Arg Ile Asn Glu Thr Asn Asn His Gln Asp Gly Lys Ile Asp Gln Leu
        290                 295                 300

Gly Tyr Ala Leu Lys Glu Gln Gly Gln His Phe Asn Asn Arg Ile Ser
305                 310                 315                 320

Ala Val Glu Arg Gln Thr Ala Gly Gly Ile Ala Asn Ala Ile Ala Ile
                325                 330                 335

Ala Thr Leu Pro Ser Pro Ser Arg Ala Gly Glu His Val Leu Phe
            340                 345                 350

Gly Ser Gly Tyr His Asn Gly Gln Ala Ala Val Ser Leu Gly Ala Ala
            355                 360                 365

Gly Leu Ser Asp Thr Gly Lys Ser Thr Tyr Lys Ile Gly Leu Ser Trp
        370                 375                 380
```

```
Ser Asp Ala Gly Gly Leu Ser Gly Gly Val Gly Gly Ser Tyr Arg Trp
385                 390                 395                 400

Lys

<210> SEQ ID NO 4
<211> LENGTH: 10
<212> TYPE: PRT

<213> ORGANISM: Moraxella catarrhalis

<400> SEQUENCE: 4

Ala Leu Glu Ser Asn Val Glu Glu Gly Leu
1               5                   10

<210> SEQ ID NO 5
<211> LENGTH: 242
<212> TYPE: PRT
<213> ORGANISM: Moraxella catarrhalis

<400> SEQUENCE: 5

Gln His Ser Ser Asp Ile Lys Thr Leu Lys Asn Asn Val Glu Glu Gly
1               5                   10                  15

Leu Leu Asp Leu Ser Gly Arg Leu Ile Asp Gln Lys Ala Asp Leu Thr
                20                  25                  30

Lys Asp Ile Lys Ala Leu Glu Ser Asn Val Glu Glu Gly Leu Leu Asp
            35                  40                  45

Leu Ser Gly Arg Leu Ile Asp Gln Lys Ala Asp Ile Ala Lys Asn Gln
    50                  55                  60

Ala Asp Ile Ala Gln Asn Gln Thr Asp Ile Gln Asp Leu Ala Ala Tyr
65                  70                  75                  80

Asn Glu Leu Gln Asp Ala Tyr Ala Lys Gln Gln Thr Glu Ala Ile Asp
                85                  90                  95

Ala Leu Asn Lys Ala Ser Ser Ala Asn Thr Asp Arg Ile Ala Thr Ala
            100                 105                 110

Glu Leu Gly Ile Ala Glu Asn Lys Lys Asp Ala Gln Ile Ala Lys Ala
        115                 120                 125

Gln Ala Asn Glu Asn Lys Asp Gly Ile Ala Lys Asn Gln Ala Asp Ile
    130                 135                 140

Gln Leu His Asp Lys Lys Ile Thr Asn Leu Gly Ile Leu His Ser Met
145                 150                 155                 160

Val Ala Arg Ala Val Gly Asn Asn Thr Gln Gly Val Ala Thr Asn Lys
                165                 170                 175

Ala Asp Ile Ala Lys Asn Gln Ala Asp Ile Ala Asn Asn Ile Lys Asn
            180                 185                 190

Ile Tyr Glu Leu Ala Gln Gln Gln Asp Gln His Ser Ser Asp Ile Lys
        195                 200                 205

Thr Leu Ala Lys Val Ser Ala Ala Asn Thr Asp Arg Ile Ala Lys Asn
    210                 215                 220

Lys Ala Glu Ala Asp Ala Ser Phe Glu Thr Leu Thr Lys Asn Gln Asn
225                 230                 235                 240

Thr Leu

<210> SEQ ID NO 6
<211> LENGTH: 21
<212> TYPE: PRT
<213> ORGANISM: Moraxella catarrhalis
```

```
<400> SEQUENCE: 6

Lys Asp Glu His Asp Lys Leu Ile Thr Ala Asn Lys Thr Ala Ile Asp
 1               5                  10                  15

Ala Asn Lys Ala Ser
            20

<210> SEQ ID NO 7
<211> LENGTH: 6
<212> TYPE: PRT
<213> ORGANISM: Moraxella catarrhalis

<400> SEQUENCE: 7

Ala Leu Glu Ser Asn Val
 1               5

<210> SEQ ID NO 8
<211> LENGTH: 10
<212> TYPE: PRT
<213> ORGANISM: Moraxella catarrhalis

<400> SEQUENCE: 8

Gln His Ser Ser Asp Ile Lys Thr Leu Lys
 1               5                  10

<210> SEQ ID NO 9
<211> LENGTH: 25
<212> TYPE: PRT
<213> ORGANISM: Moraxella catarrhalis

<400> SEQUENCE: 9

Asn Val Glu Glu Gly Leu Leu Asp Leu Ser Gly Arg Leu Ile Asp Gln
 1               5                  10                  15

Lys Ala Asp Leu Thr Lys Asp Ile Lys
            20                  25

<210> SEQ ID NO 10
<211> LENGTH: 25
<212> TYPE: PRT
<213> ORGANISM: Moraxella catarrhalis

<400> SEQUENCE: 10

Asn Val Glu Glu Gly Leu Leu Asp Leu Ser Gly Arg Leu Ile Asp Gln
 1               5                  10                  15

Lys Ala Asp Ile Ala Lys Asn Gln Ala
            20                  25

<210> SEQ ID NO 11
<211> LENGTH: 7
<212> TYPE: PRT
<213> ORGANISM: Moraxella catarrhalis

<400> SEQUENCE: 11

Asp Ile Ala Gln Asn Gln Thr
 1               5

<210> SEQ ID NO 12
<211> LENGTH: 13
<212> TYPE: PRT
<213> ORGANISM: Moraxella catarrhalis

<400> SEQUENCE: 12

Asp Ile Gln Asp Leu Ala Ala Tyr Asn Glu Leu Gln Asp
 1               5                  10
```

<210> SEQ ID NO 13
<211> LENGTH: 13
<212> TYPE: PRT
<213> ORGANISM: Moraxella catarrhalis

<400> SEQUENCE: 13

Gln Thr Glu Ala Ile Asp Ala Leu Asn Lys Ala Ser Ser
1               5                   10

<210> SEQ ID NO 14
<211> LENGTH: 29
<212> TYPE: PRT
<213> ORGANISM: Moraxella catarrhalis

<400> SEQUENCE: 14

Thr Ala Glu Leu Gly Ile Ala Glu Asn Lys Lys Asp Ala Gln Ile Ala
1               5                   10                  15

Lys Ala Gln Ala Asn Glu Asn Lys Asp Gly Ile Ala Lys
            20                  25

<210> SEQ ID NO 15
<211> LENGTH: 42
<212> TYPE: PRT
<213> ORGANISM: Moraxella catarrhalis

<400> SEQUENCE: 15

Asn Gln Ala Asp Ile Gln Leu His Asp Lys Lys Ile Thr Asn Leu Gly
1               5                   10                  15

Ile Leu His Ser Met Val Ala Arg Ala Val Gly Asn Asn Thr Gln Gly
            20                  25                  30

Val Ala Thr Asn Lys Ala Asp Ile Ala Lys
        35                  40

<210> SEQ ID NO 16
<211> LENGTH: 16
<212> TYPE: PRT
<213> ORGANISM: Moraxella catarrhalis

<400> SEQUENCE: 16

Asn Gln Ala Asp Ile Ala Asn Asn Ile Lys Asn Ile Tyr Glu Leu Ala
1               5                   10                  15

<210> SEQ ID NO 17
<211> LENGTH: 9
<212> TYPE: PRT
<213> ORGANISM: Moraxella catarrhalis

<400> SEQUENCE: 17

Asn Gln Ala Asp Ile Ala Asn Asn Ile
1               5

<210> SEQ ID NO 18
<211> LENGTH: 6
<212> TYPE: PRT
<213> ORGANISM: Moraxella catarrhalis

<400> SEQUENCE: 18

Asn Ile Tyr Glu Leu Ala
1               5

<210> SEQ ID NO 19
<211> LENGTH: 12

<212> TYPE: PRT
<213> ORGANISM: Moraxella catarrhalis

<400> SEQUENCE: 19

Ala Asn Ala Asp Asn Ala Val Ala Leu Gly Asn Lys
 1               5                  10

<210> SEQ ID NO 20
<211> LENGTH: 13
<212> TYPE: PRT
<213> ORGANISM: Moraxella catarrhalis

<400> SEQUENCE: 20

Asn Asn Val Glu Glu Gly Leu Leu Asp Leu Ser Gly Arg
 1               5                  10

<210> SEQ ID NO 21
<211> LENGTH: 16
<212> TYPE: PRT
<213> ORGANISM: Moraxella catarrhalis

<400> SEQUENCE: 21

Ala Leu Glu Ser Asn Val Glu Glu Gly Leu Leu Asp Leu Ser Gly Arg
 1               5                  10                  15

<210> SEQ ID NO 22
<211> LENGTH: 16
<212> TYPE: PRT
<213> ORGANISM: Moraxella catarrhalis

<400> SEQUENCE: 22

Thr Leu Glu Ser Asn Val Glu Glu Gly Leu Leu Asp Leu Ser Gly Arg
 1               5                  10                  15

<210> SEQ ID NO 23
<211> LENGTH: 20
<212> TYPE: PRT
<213> ORGANISM: Moraxella catarrhalis

<400> SEQUENCE: 23

Ile Gly Leu Ser Trp Ser Asp Ala Gly Gly Leu Ser Gly Gly Val Gly
 1               5                  10                  15

Gly Ser Tyr Arg
            20

<210> SEQ ID NO 24
<211> LENGTH: 20
<212> TYPE: PRT
<213> ORGANISM: Moraxella catarrhalis

<400> SEQUENCE: 24

Gln Thr Ala Gly Gly Ile Ala Asn Ala Ile Ala Ile Ala Thr Leu Pro
 1               5                  10                  15

Ser Pro Ser Arg
            20

<210> SEQ ID NO 25
<211> LENGTH: 17
<212> TYPE: PRT
<213> ORGANISM: Moraxella catarrhalis

<400> SEQUENCE: 25

Asn Gln Asn Thr Leu Ile Glu Gln Gly Glu Ala Leu Val Glu Gln Asn
 1               5                  10                  15

Lys

<210> SEQ ID NO 26
<211> LENGTH: 18
<212> TYPE: PRT
<213> ORGANISM: Moraxella catarrhalis

<400> SEQUENCE: 26

Ala Ile Asn Gln Glu Leu Glu Gly Phe Ala Ala His Ala Asp Val Gln
 1               5                  10                  15

Asp Lys

<210> SEQ ID NO 27
<211> LENGTH: 17
<212> TYPE: PRT
<213> ORGANISM: Moraxella catarrhalis

<400> SEQUENCE: 27

Asn Ile Tyr Glu Leu Ala Gln Gln Asp Gln His Ser Ser Asp Ile
 1               5                  10                  15

Lys

<210> SEQ ID NO 28
<211> LENGTH: 21
<212> TYPE: PRT
<213> ORGANISM: Moraxella catarrhalis

<400> SEQUENCE: 28

Ala Leu Glu Ser Asn Val Glu Glu Gly Leu Leu Asp Leu Ser Gly Arg
 1               5                  10                  15

Leu Ile Asp Gln Lys
            20

<210> SEQ ID NO 29
<211> LENGTH: 33
<212> TYPE: PRT
<213> ORGANISM: Moraxella catarrhalis

<400> SEQUENCE: 29

Ala Asn Thr Asp Arg Ile Ala Thr Ala Glu Leu Gly Ile Ala Glu Asn
 1               5                  10                  15

Lys Lys Asp Ala Gln Ile Ala Lys Ala Gln Ala Asn Glu Asn Lys Asp
            20                  25                  30

Gly

<210> SEQ ID NO 30
<211> LENGTH: 47
<212> TYPE: PRT
<213> ORGANISM: Moraxella catarrhalis

<400> SEQUENCE: 30

Glu Asn Lys Asp Gly Ile Ala Lys Asn Gln Ala Asp Ile Gln Leu His
 1               5                  10                  15

Asp Lys Lys Ile Thr Asn Leu Gly Ile Leu His Ser Met Val Ala Arg
            20                  25                  30

Ala Val Gly Asn Asn Thr Gln Gly Val Ala Thr Asn Lys Ala Asp
        35                  40                  45

<210> SEQ ID NO 31
<211> LENGTH: 30

```
<212> TYPE: PRT
<213> ORGANISM: Moraxella catarrhalis

<400> SEQUENCE: 31

Lys Asp Ala Gln Ile Ala Lys Ala Gln Ala Asn Glu Asn Lys Asp Gly
 1               5                  10                  15

Ile Ala Lys Asn Gln Ala Asp Ile Gln Leu His Asp Lys Lys
            20                  25                  30

<210> SEQ ID NO 32
<211> LENGTH: 20
<212> TYPE: PRT
<213> ORGANISM: Moraxella catarrhalis

<400> SEQUENCE: 32

Gln Ile Ala Lys Ala Gln Ala Asn Glu Asn Lys Asp Gly Ile Ala Lys
 1               5                  10                  15

Asn Gln Ala Asp
            20

<210> SEQ ID NO 33
<211> LENGTH: 20
<212> TYPE: PRT
<213> ORGANISM: Moraxella catarrhalis

<400> SEQUENCE: 33

Lys Asp Gly Ile Ala Lys Asn Gln Ala Asp Ile Gln Leu His Asp Lys
 1               5                  10                  15

Lys Ile Thr Asn
            20

<210> SEQ ID NO 34
<211> LENGTH: 20
<212> TYPE: PRT
<213> ORGANISM: Moraxella catarrhalis

<400> SEQUENCE: 34

Ile Gln Leu His Asp Lys Lys Ile Thr Asn Leu Gly Ile Leu His Ser
 1               5                  10                  15

Met Val Ala Arg
            20

<210> SEQ ID NO 35
<211> LENGTH: 20
<212> TYPE: PRT
<213> ORGANISM: Moraxella catarrhalis

<400> SEQUENCE: 35

Leu Gly Ile Leu His Ser Met Val Ala Arg Ala Val Gly Asn Asn Thr
 1               5                  10                  15

Gln Gly Val Ala
            20

<210> SEQ ID NO 36
<211> LENGTH: 20
<212> TYPE: PRT
<213> ORGANISM: Moraxella catarrhalis

<400> SEQUENCE: 36

Ala Val Gly Asn Asn Thr Gln Gly Val Ala Thr Asn Lys Ala Asp Ile
 1               5                  10                  15

Ala Lys Asn Gln
```

```
<210> SEQ ID NO 37
<211> LENGTH: 20
<212> TYPE: PRT
<213> ORGANISM: Moraxella catarrhalis

<400> SEQUENCE: 37

Thr Asn Lys Ala Asp Ile Ala Lys Asn Gln Ala Asp Ile Ala Asn Asn
 1               5                  10                  15

Ile Lys Asn Ile
            20

<210> SEQ ID NO 38
<211> LENGTH: 5
<212> TYPE: PRT
<213> ORGANISM: Moraxella catarrhalis

<400> SEQUENCE: 38

Asn Lys Asp Gly Ile
 1               5

<210> SEQ ID NO 39
<211> LENGTH: 7
<212> TYPE: PRT
<213> ORGANISM: Moraxella catarrhalis

<400> SEQUENCE: 39

Glu Asn Lys Asp Gly Ile Ala
 1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 40

His His His His His His
 1               5

<210> SEQ ID NO 41
<211> LENGTH: 142
<212> TYPE: PRT
<213> ORGANISM: Moraxella catarrhalis

<400> SEQUENCE: 41

Ala Ser Ser Ala Asn Thr Asp Arg Ile Ala Thr Ala Glu Leu Gly Ile
 1               5                  10                  15

Ala Glu Asn Lys Lys Asp Ala Gln Ile Ala Lys Ala Gln Ala Asn Glu
                20                  25                  30

Asn Lys Asp Gly Ile Ala Lys Asn Gln Ala Asp Ile Gln Leu His Asp
            35                  40                  45

Lys Lys Ile Thr Asn Leu Gly Ile Leu His Ser Met Val Ala Arg Ala
        50                  55                  60

Val Gly Asn Asn Thr Gln Gly Val Ala Thr Asn Lys Ala Asp Ile Ala
 65                  70                  75                  80

Lys Asn Gln Ala Asp Ile Ala Asn Asn Ile Lys Asn Ile Tyr Glu Leu
                85                  90                  95

Ala Gln Gln Gln Asp Gln His Ser Ser Asp Ile Lys Thr Leu Ala Lys
```

```
                    100                 105                 110

Val Ser Ala Ala Asn Thr Asp Arg Ile Ala Lys Asn Lys Ala Glu Ala
            115                 120                 125

Asp Ala Ser Phe Glu Thr Leu Thr Lys Asn Gln Asn Thr Leu
        130                 135                 140

<210> SEQ ID NO 42
<211> LENGTH: 142
<212> TYPE: PRT
<213> ORGANISM: Moraxella catarrhalis

<400> SEQUENCE: 42

Ala Ser Ser Ala Asn Thr Asp Arg Ile Ala Thr Ala Glu Leu Gly Ile
  1               5                  10                  15

Ala Glu Asn Lys Lys Asp Ala Gln Ile Ala Lys Ala Gln Ala Asn Glu
             20                  25                  30

Asn Lys Asp Gly Ile Ala Lys Asn Gln Ala Asp Ile Gln Leu His Asp
         35                  40                  45

Lys Lys Ile Thr Asn Leu Gly Ile Leu His Ser Met Val Ala Arg Ala
     50                  55                  60

Val Gly Asn Asn Thr Gln Gly Val Ala Thr Asn Lys Ala Asp Ile Ala
 65                  70                  75                  80

Lys Asn Gln Ala Asp Ile Ala Asn Asn Ile Lys Asn Ile Tyr Glu Leu
                 85                  90                  95

Ala Gln Gln Gln Asp Gln His Ser Ser Asp Ile Lys Thr Leu Ala Lys
            100                 105                 110

Val Ser Ala Ala Asn Thr Asp Arg Ile Ala Lys Asn Lys Ala Glu Ala
        115                 120                 125

Asp Ala Ser Phe Glu Thr Leu Thr Lys Asn Gln Asn Thr Leu
    130                 135                 140

<210> SEQ ID NO 43
<211> LENGTH: 100
<212> TYPE: PRT
<213> ORGANISM: Moraxella catarrhalis

<400> SEQUENCE: 43

Ala Ser Ser Ala Asn Thr Asp Arg Ile Ala Thr Ala Glu Leu Gly Ile
  1               5                  10                  15

Ala Glu Asn Lys Lys Asp Ala Gln Ile Ala Lys Ala Gln Ala Asn Glu
             20                  25                  30

Asn Lys Asp Gly Ile Ala Lys Asn Gln Ala Asp Ile Ala Asn Asn Ile
         35                  40                  45

Lys Asn Ile Tyr Glu Leu Ala Gln Gln Gln Asp Gln His Ser Ser Asp
     50                  55                  60

Ile Lys Thr Leu Ala Lys Val Ser Ala Ala Asn Thr Asp Arg Ile Ala
 65                  70                  75                  80

Lys Asn Lys Ala Glu Ala Asp Ala Ser Phe Glu Thr Leu Thr Lys Asn
                 85                  90                  95

Gln Asn Thr Leu
            100

<210> SEQ ID NO 44
<211> LENGTH: 142
<212> TYPE: PRT
<213> ORGANISM: Moraxella catarrhalis

<400> SEQUENCE: 44
```

```
Ala Ser Ser Ala Asn Thr Asp Arg Ile Ala Thr Ala Glu Leu Gly Ile
 1               5                  10                  15

Ala Glu Asn Lys Lys Asp Ala Gln Ile Ala Lys Ala Gln Ala Asn Glu
             20                  25                  30

Asn Lys Asp Gly Ile Ala Lys Asn Gln Ala Asp Ile Gln Leu His Asp
         35                  40                  45

Lys Lys Ile Thr Asn Leu Gly Ile Leu His Ser Met Val Ala Arg Ala
     50                  55                  60

Val Gly Asn Asn Thr Gln Gly Val Ala Thr Asn Lys Ala Asp Ile Ala
 65                  70                  75                  80

Lys Asn Gln Ala Asp Ile Ala Asn Asn Ile Lys Asn Ile Tyr Glu Leu
             85                  90                  95

Ala Gln Gln Gln Asp Gln His Ser Ser Asp Ile Lys Thr Leu Ala Lys
            100                 105                 110

Val Ser Ala Ala Asn Thr Asp Arg Ile Ala Lys Asn Lys Ala Glu Ala
            115                 120                 125

Asp Ala Ser Phe Glu Thr Leu Thr Lys Asn Gln Asn Thr Leu
130                 135                 140
```

<210> SEQ ID NO 45
<211> LENGTH: 142
<212> TYPE: PRT
<213> ORGANISM: Moraxella catarrhalis

<400> SEQUENCE: 45

```
Ala Ser Ser Ala Asn Thr Asp Arg Ile Ala Thr Ala Glu Leu Gly Ile
 1               5                  10                  15

Ala Glu Asn Lys Lys Asp Ala Gln Ile Ala Lys Ala Gln Ala Asn Glu
             20                  25                  30

Asn Lys Asp Gly Ile Ala Lys Asn Gln Ala Asp Ile Gln Leu His Asp
         35                  40                  45

Lys Lys Ile Thr Asn Leu Gly Ile Leu His Ser Met Val Ala Arg Ala
     50                  55                  60

Val Gly Asn Asn Thr Gln Gly Val Ala Thr Asn Lys Ala Asp Ile Ala
 65                  70                  75                  80

Lys Asn Gln Ala Asp Ile Ala Asn Asn Ile Lys Asn Ile Tyr Glu Leu
             85                  90                  95

Ala Gln Gln Gln Asp Gln His Ser Ser Asp Ile Lys Thr Leu Ala Lys
            100                 105                 110

Val Ser Ala Ala Asn Thr Asp Arg Ile Ala Lys Asn Lys Ala Glu Ala
            115                 120                 125

Asp Ala Ser Phe Glu Thr Leu Thr Lys Asn Gln Asn Thr Leu
130                 135                 140
```

<210> SEQ ID NO 46
<211> LENGTH: 72
<212> TYPE: PRT
<213> ORGANISM: Moraxella catarrhalis

<400> SEQUENCE: 46

```
Ala Ser Ser Glu Asn Thr Gln Asn Ile Ala Lys Asn Gln Ala Asp Ile
 1               5                  10                  15

Ala Asn Asn Ile Asn Asn Ile Tyr Glu Leu Ala Gln Gln Gln Asp Gln
             20                  25                  30

His Ser Ser Asp Ile Lys Thr Leu Ala Lys Val Ser Ala Ala Asn Thr
         35                  40                  45
```

```
Asp Arg Ile Ala Lys Asn Lys Ala Glu Ala Asp Ala Ser Phe Glu Thr
         50                  55                  60

Leu Thr Lys Asn Gln Asn Thr Leu
 65                  70

<210> SEQ ID NO 47
<211> LENGTH: 142
<212> TYPE: PRT
<213> ORGANISM: Moraxella catarrhalis

<400> SEQUENCE: 47

Ala Ser Ser Ala Asn Thr Asp Arg Ile Ala Thr Ala Glu Leu Gly Ile
 1               5                  10                  15

Ala Glu Asn Lys Lys Asp Ala Gln Ile Ala Lys Ala Gln Ala Asn Glu
                20                  25                  30

Asn Lys Asp Gly Ile Ala Lys Asn Gln Ala Asp Ile Gln Leu His Asp
             35                  40                  45

Lys Lys Ile Thr Asn Leu Gly Ile Leu His Ser Met Val Ala Arg Ala
         50                  55                  60

Val Gly Asn Asn Thr Gln Gly Val Ala Thr Asn Lys Ala Asp Ile Ala
 65                  70                  75                  80

Lys Asn Gln Ala Asp Ile Ala Asn Asn Ile Lys Asn Ile Tyr Glu Leu
                85                  90                  95

Ala Gln Gln Gln Asp Gln His Ser Ser Asp Ile Lys Thr Leu Ala Lys
            100                 105                 110

Val Ser Ala Ala Asn Thr Asp Arg Ile Ala Lys Asn Lys Ala Glu Ala
        115                 120                 125

Asp Ala Ser Phe Glu Thr Leu Thr Lys Asn Gln Asn Thr Leu
    130                 135                 140

<210> SEQ ID NO 48
<211> LENGTH: 142
<212> TYPE: PRT
<213> ORGANISM: Moraxella catarrhalis

<400> SEQUENCE: 48

Ala Ser Ser Ala Asn Thr Asp Arg Ile Ala Thr Ala Glu Leu Gly Ile
 1               5                  10                  15

Ala Glu Asn Lys Lys Asp Ala Gln Ile Ala Lys Ala Gln Ala Asn Glu
                20                  25                  30

Asn Lys Asp Gly Ile Ala Lys Asn Gln Ala Asp Ile Gln Leu His Asp
             35                  40                  45

Lys Lys Ile Thr Asn Leu Gly Ile Leu His Ser Met Val Ala Arg Ala
         50                  55                  60

Val Gly Asn Asn Thr Gln Gly Val Ala Thr Asn Lys Ala Asp Ile Ala
 65                  70                  75                  80

Lys Asn Gln Ala Asp Ile Ala Asn Asn Ile Lys Asn Ile Tyr Glu Leu
                85                  90                  95

Ala Gln Gln Gln Asp Gln His Ser Ser Asp Ile Lys Thr Leu Ala Lys
            100                 105                 110

Val Ser Ala Ala Asn Thr Asp Arg Ile Ala Lys Asn Lys Ala Glu Ala
        115                 120                 125

Asp Ala Ser Phe Glu Thr Leu Thr Lys Asn Gln Asn Thr Leu
    130                 135                 140

<210> SEQ ID NO 49
```

<211> LENGTH: 142
<212> TYPE: PRT
<213> ORGANISM: Moraxella catarrhalis

<400> SEQUENCE: 49

```
Ala Ser Ser Ala Asn Thr Asp Arg Ile Ala Thr Ala Glu Leu Gly Ile
  1               5                  10                  15
Ala Glu Asn Lys Lys Asp Ala Gln Ile Ala Lys Ala Gln Ala Asn Glu
                 20                  25                  30
Asn Lys Asp Gly Ile Ala Lys Asn Gln Ala Asp Ile Gln Leu His Asp
             35                  40                  45
Lys Lys Ile Thr Asn Leu Gly Ile Leu His Ser Met Val Ala Arg Ala
 50                  55                  60
Val Gly Asn Asn Thr Gln Gly Val Ala Thr Asn Lys Ala Asp Ile Ala
 65                  70                  75                  80
Lys Asn Gln Ala Asp Ile Ala Asn Asn Ile Lys Asn Ile Tyr Glu Leu
                 85                  90                  95
Ala Gln Gln Gln Asp Gln His Ser Ser Asp Ile Lys Thr Leu Ala Lys
            100                 105                 110
Val Ser Ala Ala Asn Thr Asp Arg Ile Ala Lys Asn Lys Ala Glu Ala
            115                 120                 125
Asp Ala Ser Phe Glu Thr Leu Thr Lys Asn Gln Asn Thr Leu
            130                 135                 140
```

<210> SEQ ID NO 50
<211> LENGTH: 129
<212> TYPE: PRT
<213> ORGANISM: Moraxella catarrhalis

<400> SEQUENCE: 50

```
Leu Gly Ile Ala Glu Asn Lys Lys Asp Ala Gln Ile Ala Lys Ala Gln
  1               5                  10                  15
Ala Asn Glu Asn Lys Asp Gly Ile Ala Lys Asn Gln Ala Asp Ile Gln
                 20                  25                  30
Leu His Asp Lys Lys Ile Thr Asn Leu Gly Ile Leu His Ser Met Val
             35                  40                  45
Ala Arg Ala Val Gly Asn Asn Thr Gln Gly Val Ala Thr Asn Lys Ala
 50                  55                  60
Asp Ile Ala Lys Asn Gln Ala Asp Ile Ala Asn Asn Ile Lys Asn Ile
 65                  70                  75                  80
Tyr Glu Leu Ala Gln Gln Gln Asp Gln His Ser Ser Asp Ile Lys Thr
                 85                  90                  95
Leu Ala Lys Val Ser Ala Ala Asn Thr Asp Arg Ile Ala Lys Asn Lys
            100                 105                 110
Ala Glu Ala Asp Ala Ser Phe Glu Thr Leu Thr Lys Asn Gln Asn Thr
            115                 120                 125
Leu
```

<210> SEQ ID NO 51
<211> LENGTH: 125
<212> TYPE: PRT
<213> ORGANISM: Moraxella catarrhalis

<400> SEQUENCE: 51

```
Glu Asn Lys Lys Asp Ala Gln Ile Ala Lys Ala Gln Ala Asn Glu Asn
  1               5                  10                  15
Lys Asp Gly Ile Ala Lys Asn Gln Ala Asp Ile Gln Leu His Asp Lys
```

-continued

```
                20                  25                  30
Lys Ile Thr Asn Leu Gly Ile Leu His Ser Met Val Ala Arg Ala Val
             35                  40                  45

Gly Asn Asn Thr Gln Gly Val Ala Thr Asn Lys Ala Asp Ile Ala Lys
         50                  55                  60

Asn Gln Ala Asp Ile Ala Asn Asn Ile Lys Asn Ile Tyr Glu Leu Ala
     65                  70                  75                  80

Gln Gln Gln Asp Gln His Ser Ser Asp Ile Lys Thr Leu Ala Lys Val
                 85                  90                  95

Ser Ala Ala Asn Thr Asp Arg Ile Ala Lys Asn Lys Ala Glu Ala Asp
            100                 105                 110

Ala Ser Phe Glu Thr Leu Thr Lys Asn Gln Asn Thr Leu
        115                 120                 125

<210> SEQ ID NO 52
<211> LENGTH: 197
<212> TYPE: PRT
<213> ORGANISM: Moraxella catarrhalis

<400> SEQUENCE: 52

Gln His Ser Ser Asp Ile Lys Thr Leu Lys Asn Asn Val Glu Glu Gly
  1               5                  10                  15

Leu Leu Asp Leu Ser Gly Arg Leu Ile Asp Gln Lys Ala Asp Leu Thr
             20                  25                  30

Lys Asp Ile Lys Ala Leu Glu Ser Asn Val Glu Glu Gly Leu Leu Asp
         35                  40                  45

Leu Ser Gly Arg Leu Ile Asp Gln Lys Ala Asp Ile Ala Lys Asn Gln
     50                  55                  60

Ala Asp Ile Ala Gln Asn Gln Thr Asp Ile Gln Asp Leu Ala Ala Tyr
 65                  70                  75                  80

Asn Glu Leu Gln Asp Ala Tyr Ala Lys Gln Gln Thr Glu Ala Ile Asp
                 85                  90                  95

Ala Leu Asn Lys Ala Ser Ser Ala Asn Thr Asp Arg Ile Ala Thr Ala
            100                 105                 110

Glu Leu Gly Ile Ala Glu Asn Lys Lys Asp Ala Gln Ile Ala Lys Ala
        115                 120                 125

Gln Ala Asn Glu Asn Lys Asp Gly Ile Ala Lys Asn Gln Ala Asp Ile
    130                 135                 140

Gln Leu His Asp Lys Lys Ile Thr Asn Leu Gly Ile Leu His Ser Met
145                 150                 155                 160

Val Ala Arg Ala Val Gly Asn Asn Thr Gln Gly Val Ala Thr Asn Lys
                165                 170                 175

Ala Asp Ile Ala Lys Asn Gln Ala Asp Ile Ala Asn Asn Ile Lys Asn
            180                 185                 190

Ile Tyr Glu Leu Ala
        195

<210> SEQ ID NO 53
<211> LENGTH: 197
<212> TYPE: PRT
<213> ORGANISM: Moraxella catarrhalis

<400> SEQUENCE: 53

Gln His Ser Ser Asp Ile Lys Thr Leu Lys Asn Asn Val Glu Glu Gly
  1               5                  10                  15

Leu Leu Asp Leu Ser Gly Arg Leu Ile Asp Gln Lys Ala Asp Leu Thr
```

-continued

```
                20                  25                  30
Lys Asp Ile Lys Ala Leu Glu Asn Asn Val Glu Glu Gly Leu Leu Asp
        35                  40                  45

Leu Ser Gly Arg Leu Ile Asp Gln Lys Ala Asp Ile Ala Lys Asn Gln
    50                  55                  60

Ala Asp Ile Ala Gln Asn Gln Thr Asp Ile Gln Asp Leu Ala Ala Tyr
65                  70                  75                  80

Asn Glu Leu Gln Asp Ala Tyr Ala Lys Gln Gln Thr Glu Ala Ile Asp
                85                  90                  95

Ala Leu Asn Lys Ala Ser Ser Asn Thr Asp Arg Ile Ala Thr Ala
            100                 105                 110

Glu Leu Gly Ile Ala Glu Asn Lys Asp Ala Gln Ile Ala Lys Ala
        115                 120                 125

Gln Ala Asn Glu Asn Lys Asp Gly Ile Ala Lys Asn Gln Ala Asp Ile
    130                 135                 140

Gln Leu His Asp Lys Lys Ile Thr Asn Leu Gly Ile Leu His Ser Met
145                 150                 155                 160

Val Ala Arg Ala Val Gly Asn Asn Thr Gln Gly Val Ala Thr Asn Lys
                165                 170                 175

Ala Asp Ile Ala Lys Asn Gln Ala Asp Ile Ala Asn Asn Ile Lys Asn
            180                 185                 190

Ile Tyr Glu Leu Ala
        195

<210> SEQ ID NO 54
<211> LENGTH: 148
<212> TYPE: PRT
<213> ORGANISM: Moraxella catarrhalis

<400> SEQUENCE: 54

Gln His Ser Ser Asp Ile Lys Thr Leu Lys Asn Asn Val Glu Glu Gly
1               5                   10                  15

Leu Leu Asp Leu Ser Gly Arg Leu Ile Asp Gln Lys Ala Asp Leu Thr
            20                  25                  30

Lys Asp Ile Lys Ala Leu Glu Asn Asn Val Glu Glu Gly Leu Leu Asp
        35                  40                  45

Leu Ser Gly Arg Leu Ile Asp Gln Lys Ala Asp Ile Ala Lys Asn Gln
    50                  55                  60

Ala Asp Ile Gln Asp Leu Ala Ala Tyr Asn Glu Leu Gln Asp Gln Tyr
65                  70                  75                  80

Ala Gln Lys Gln Thr Glu Ala Ile Asp Ala Leu Asn Lys Ala Ser Ser
                85                  90                  95

Ala Asn Thr Asp Arg Ile Ala Thr Ala Glu Leu Gly Ile Ala Glu Asn
            100                 105                 110

Lys Lys Asp Ala Gln Ile Ala Lys Ala Gln Ala Asn Glu Asn Lys Asp
        115                 120                 125

Gly Ile Ala Lys Asn Gln Ala Asp Ile Ala Asn Asn Ile Lys Asn Ile
    130                 135                 140

Tyr Glu Leu Ala
145

<210> SEQ ID NO 55
<211> LENGTH: 197
<212> TYPE: PRT
<213> ORGANISM: Moraxella catarrhalis
```

<400> SEQUENCE: 55

```
Gln His Ser Ser Asp Ile Lys Thr Leu Lys Asn Asn Val Glu Glu Gly
  1               5                  10                  15

Leu Leu Asp Leu Ser Gly Arg Leu Ile Asp Gln Lys Ala Asp Leu Thr
             20                  25                  30

Lys Asp Ile Lys Thr Leu Glu Ser Asn Val Glu Glu Gly Leu Leu Asp
         35                  40                  45

Leu Ser Gly Arg Leu Ile Asp Gln Lys Ala Asp Ile Ala Lys Asn Gln
     50                  55                  60

Ala Asp Ile Ala Gln Asn Gln Thr Asp Ile Gln Asp Leu Ala Ala Tyr
 65                  70                  75                  80

Asn Glu Leu Gln Asp Gln Tyr Ala Gln Lys Gln Thr Glu Ala Ile Asp
                 85                  90                  95

Ala Leu Asn Lys Ala Ser Ser Ala Asn Thr Asp Arg Ile Ala Thr Ala
             100                 105                 110

Glu Leu Gly Ile Ala Glu Asn Lys Lys Asp Ala Gln Ile Ala Lys Ala
         115                 120                 125

Gln Ala Asn Glu Asn Lys Asp Gly Ile Ala Lys Asn Gln Ala Asp Ile
     130                 135                 140

Gln Leu His Asp Lys Lys Ile Thr Asn Leu Gly Ile Leu His Ser Met
145                 150                 155                 160

Val Ala Arg Ala Val Gly Asn Asn Thr Gln Gly Val Ala Thr Asn Lys
                 165                 170                 175

Ala Asp Ile Ala Lys Asn Gln Ala Asp Ile Ala Asn Asn Ile Lys Asn
             180                 185                 190

Ile Tyr Glu Leu Ala
         195
```

<210> SEQ ID NO 56
<211> LENGTH: 197
<212> TYPE: PRT
<213> ORGANISM: Moraxella catarrhalis

<400> SEQUENCE: 56

```
Gln His Ser Ser Asp Ile Lys Thr Leu Lys Lys Asn Val Glu Glu Gly
  1               5                  10                  15

Leu Leu Asp Leu Ser Gly Arg Leu Ile Asp Gln Lys Ala Asp Leu Thr
             20                  25                  30

Lys Asp Ile Lys Thr Leu Glu Asn Asn Val Glu Glu Gly Leu Leu Asp
         35                  40                  45

Leu Ser Gly Arg Leu Ile Asp Gln Lys Ala Asp Ile Ala Lys Asn Gln
     50                  55                  60

Ala Asp Ile Ala Gln Asn Gln Thr Asp Ile Gln Asp Leu Ala Ala Tyr
 65                  70                  75                  80

Asn Glu Leu Gln Asp Gln Tyr Ala Gln Lys Gln Thr Glu Ala Ile Asp
                 85                  90                  95

Ala Leu Asn Lys Ala Ser Ser Ala Asn Thr Asp Arg Ile Ala Thr Ala
             100                 105                 110

Glu Leu Gly Ile Ala Glu Asn Lys Lys Asp Ala Gln Ile Ala Lys Ala
         115                 120                 125

Gln Ala Asn Glu Asn Lys Asp Gly Ile Ala Lys Asn Gln Ala Asp Ile
     130                 135                 140

Gln Leu His Asp Lys Lys Ile Thr Asn Leu Gly Ile Leu His Ser Met
145                 150                 155                 160
```

```
Val Ala Arg Ala Val Gly Asn Asn Thr Gln Gly Val Ala Thr Asn Lys
            165                 170                 175

Ala Asp Ile Ala Lys Asn Gln Ala Asp Ile Ala Asn Asn Ile Lys Asn
            180                 185                 190

Ile Tyr Glu Leu Ala
        195

<210> SEQ ID NO 57
<211> LENGTH: 197
<212> TYPE: PRT
<213> ORGANISM: Moraxella catarrhalis

<400> SEQUENCE: 57

Gln His Ser Ser Asp Ile Lys Thr Leu Lys Asn Asn Val Glu Glu Gly
 1               5                   10                  15

Leu Leu Asp Leu Ser Gly Arg Leu Ile Asp Gln Lys Ala Asp Leu Thr
            20                  25                  30

Lys Asp Ile Lys Thr Leu Lys Asn Asn Val Glu Glu Gly Leu Leu Asp
        35                  40                  45

Leu Ser Gly Arg Leu Ile Asp Gln Lys Ala Asp Ile Ala Lys Asn Gln
    50                  55                  60

Ala Asp Ile Ala Gln Asn Gln Thr Asp Ile Gln Asp Leu Ala Ala Tyr
65                  70                  75                  80

Asn Glu Leu Gln Asp Gln Tyr Ala Lys Gln Thr Glu Ala Ile Asp
                85                  90                  95

Ala Leu Asn Lys Ala Ser Ser Ala Asn Thr Asp Arg Ile Ala Thr Ala
            100                 105                 110

Glu Leu Gly Ile Ala Glu Asn Lys Lys Asp Ala Gln Ile Ala Lys Ala
            115                 120                 125

Gln Ala Asn Glu Asn Lys Asp Gly Ile Ala Lys Asn Gln Ala Asp Ile
        130                 135                 140

Gln Leu His Asp Lys Lys Ile Thr Asn Leu Gly Ile Leu His Ser Met
145                 150                 155                 160

Val Ala Arg Ala Val Gly Asn Asn Thr Gln Gly Val Ala Thr Asn Lys
            165                 170                 175

Ala Asp Ile Ala Lys Asn Gln Ala Asp Ile Ala Asn Asn Ile Lys Asn
            180                 185                 190

Ile Tyr Glu Leu Ala
        195

<210> SEQ ID NO 58
<211> LENGTH: 168
<212> TYPE: PRT
<213> ORGANISM: Moraxella catarrhalis

<400> SEQUENCE: 58

Gln His Ser Ser Asp Ile Lys Thr Leu Lys Asn Asn Val Glu Glu Gly
 1               5                   10                  15

Leu Leu Asp Leu Ser Gly Arg Leu Ile Asp Gln Lys Ala Asp Ile Ala
            20                  25                  30

Lys Asn Gln Ala Asp Ile Ala Gln Asn Gln Thr Asp Ile Gln Asp Leu
        35                  40                  45

Ala Ala Tyr Asn Glu Leu Gln Asp Ala Tyr Ala Lys Gln Gln Thr Glu
    50                  55                  60

Ala Ile Asp Ala Leu Asn Lys Ala Ser Ser Ala Asn Thr Asp Arg Ile
65                  70                  75                  80
```

```
Ala Thr Ala Glu Leu Gly Ile Ala Glu Asn Lys Lys Asp Ala Gln Ile
                85                  90                  95

Ala Lys Ala Gln Ala Asn Glu Asn Lys Asp Gly Ile Ala Lys Asn Gln
            100                 105                 110

Ala Asp Ile Gln Leu His Asp Lys Lys Ile Thr Asn Leu Gly Ile Leu
        115                 120                 125

His Ser Met Val Ala Arg Ala Val Gly Asn Asn Thr Gln Gly Val Ala
    130                 135                 140

Thr Asn Lys Ala Asp Ile Ala Lys Asn Gln Ala Asp Ile Ala Asn Asn
145                 150                 155                 160

Ile Lys Asn Ile Tyr Glu Leu Ala
                165
```

<210> SEQ ID NO 59
<211> LENGTH: 98
<212> TYPE: PRT
<213> ORGANISM: Moraxella catarrhalis

<400> SEQUENCE: 59

```
Gln His Ser Ser Asp Ile Lys Thr Leu Lys Asn Asn Val Glu Glu Gly
  1               5                  10                  15

Leu Leu Asp Leu Ser Gly Arg Leu Ile Asp Gln Lys Ala Asp Ile Ala
             20                  25                  30

Lys Asn Gln Ala Asp Ile Ala Gln Asn Gln Thr Asp Ile Gln Asp Leu
         35                  40                  45

Ala Ala Tyr Asn Glu Leu Gln Asp Gln Tyr Ala Gln Lys Gln Thr Glu
     50                  55                  60

Ala Ile Asp Ala Leu Asn Lys Ala Ser Ser Glu Asn Thr Gln Asn Ile
 65                  70                  75                  80

Ala Lys Asn Gln Ala Asp Ile Ala Asn Asn Ile Asn Asn Ile Tyr Glu
                 85                  90                  95

Leu Ala
```

<210> SEQ ID NO 60
<211> LENGTH: 142
<212> TYPE: PRT
<213> ORGANISM: Moraxella catarrhalis

<400> SEQUENCE: 60

```
Ala Ser Ser Ala Asn Thr Asp Arg Ile Ala Thr Ala Glu Leu Gly Ile
  1               5                  10                  15

Ala Glu Asn Lys Lys Asp Ala Gln Ile Ala Lys Ala Gln Ala Asn Glu
             20                  25                  30

Asn Lys Asp Gly Ile Ala Lys Asn Gln Ala Asp Ile Gln Leu His Asp
         35                  40                  45

Lys Lys Ile Thr Asn Leu Gly Ile Leu His Ser Met Val Ala Arg Ala
     50                  55                  60

Val Gly Asn Asn Thr Gln Gly Val Ala Thr Asn Lys Ala Asp Ile Ala
 65                  70                  75                  80

Lys Asn Gln Ala Asp Ile Ala Asn Asn Ile Asn Asn Ile Tyr Glu Leu
                 85                  90                  95

Ala Gln Gln Gln Asp Gln His Ser Ser Asp Ile Lys Thr Leu Ala Lys
            100                 105                 110
```

```
Val Ser Ala Ala Asn Thr Asp Arg Ile Ala Lys Asn Lys Ala Glu Ala
        115                 120                 125
Asp Ala Ser Phe Glu Thr Leu Thr Lys Asn Gln Asn Thr Leu
    130                 135                 140
```

THERAPEUTIC PEPTIDES

RELATED APPLICATIONS

This application is a continuation-in-part of and claims priority to international application number PCT/GB2003/004273, filed Oct. 1, 2003, which designates the United States and was published in English on Apr. 15, 2004 as international publication number WO 2004/031236 A2, which in turn claims priority to GB 02227643, filed Oct. 2, 2002. This application also claims priority to GB 0408390.3, filed Apr. 15, 2004, and GB 0419594.7, filed Sep. 3, 2004. The disclosures of each of PCT/GB2003/004273, filed Oct. 1, 2003, GB 02227643, filed Oct. 2, 2002, GB 0408390.3, filed Apr. 15, 2004 and GB 0419594.7, filed Sep. 3, 2004 are incorporated herein in their entireties by this reference.

This invention relates to therapeutic peptides and in particular to therapeutic peptides which are useful in the preparation of vaccines or other treatments for infection as well as in the screening of compounds for potential pharmaceutical activity in the treatment of infections.

The present inventors have previously identified that Carcinoembryonic antigen related cell adhesion molecules (CEACAMs) are receptors for pathogens of mucosal membranes, especially for respiratory pathogens such as *Neisseria meningitidis*, *Haemophilus influenzae* and *Moraxella catarrhalis*. CEACAMs belong to the CarcinoEmbryonic Antigen (CEA) family, a member of the Immunoglobulin superfamily. The CEA gene family comprises surface expressed (CEA) and secreted (pregnancy-specific glycoprotein, PSG) sub-families. The membrane-associated sub-family redefined as CEACAM (CEA-related cell adhesion molecule) [20] comprises several related glycoproteins of which CEACAM1 is the most widely expressed in distinct human tissues [12]. The studies reported by the inventors primarily used Chinese Hamster Ovary (CHO) cells transfected with CEACAM1 (previously termed CD66a and BGPc) that contains four extracellular domains, a TM region and a short (S) or a long (L) cytoplasmic tail (molecular formula: NA1BA2-TM-S or L). In addition, soluble truncated constructs containing one or more of the extracellular domains were used. Previous studies demonstrated that both *Neisseria meningitidis* and *Haemophilus influenzae* primarily target the N-domain of several CEACAMs [7,9,10]. Such targeting may lead to cell surface attachment as well as cellular invasion [9]. In addition, bacteria may bind to CEACAMs on phagocytic cells and T and B lymphocytes. Such interactions may lead to bacterial cell death [8], target cell death or inhibition of immune function, e.g. of T and B lymphcytes when *N. gonorrhoeae* (closely related to *N. meningitidis*) binds to CEACAMs of these lymphocytes [21,22], The presence of CEACAM-binding ligands in *Moraxella catarrhalis* and *Haemophilus influenzae* has been a surprising find to the present inventors since CEACAMs have long been associated with outer membrane opacity-associated Opa proteins of *Neisseriae* and neither *Haemophilus influenzae* nor *Moraxella catarrhalis* produce Opa proteins. In the description which follows, the present invention will be described with particular reference to infection of the mucosal membranes, especially of the respiratory membranes, or to infection of the ear (especially otitis media) but it is to be understood that the invention finds equal utility in other areas such as the genital mucosa or the urethrae where CEACAM receptors are implicated in infection or other receptor-binding processes or elsewhere in human infection where bacteria may become disseminated from mucosal surfaces.

The mucosal pathogens *Neisseria meningitidis* (Nm), *Haemophilus influenzae* (Hi) and *Moraxella catarrhalis* (Mx) are human specific organisms and reside in the upper respiratory tract from where they may disseminate to cause serious infections. Meningococcal strains of distinct serogroups may be carried within the nasopharynx of up to 25% of healthy individuals[1]. However, in a number of subjects, the organism invades the mucosal barrier to cause one of the most rapidly advancing and extremely serious diseases. The precise factors that increase host susceptibility to meningococcal infection are not fully understood. Moreover, the limited protection afforded by group-specific vaccines and the non-immunogenicity of the group B polysaccharide underscore the need for fundamental studies to understand host susceptibility and identify salient sub-capsular features that could serve as common targets to combat meningococci. Studies by the present inventors have provided an understanding of the molecular basis of meningococcal colonization, the nature of its interactions with human barrier cells (epithelial and endothelial) as well as phagocytic cells. In recent years, the basis for mucosal colonization by commensal *Neisseriae* has been investigated to understand the features which differentiate between largely harmless colonisers and occasional but serious pathogens such as Nm. In addition, the studies have determined whether commensal *Neisseriae* could be used as carriers of potential vaccine antigens of Nm.

Up to 75% of healthy individuals may carry strains belonging to the species *H. influenzae* [2]. Although as a result of the Hib vaccine, there has been a dramatic decrease in the incidence of the type b disease in the West, diseases caused by non-typable Hi (NTHi) strains remain a major problem. NTHi cause localized as well as disseminated infections including epiglottitis, otitis media, cellulitis, pneumonia, endocarditis, bacteraemia and meningitis. Otitis media is one of the major problems in paediatric medicine and NTHi are responsible for over 20% of episodes in children during the first year of life [2,3]. NTHi are also associated with acute recurrent and persistent infections in patients with chronic obstructive pulmonary disease (COPD) and cystic fibrosis. What determines recurrent infections by NTHi in these patients or multiple episodes of otitis media in children is unclear[2,3,4].

*Moraxella catarrhalis*, another resident of the human respiratory tract, is often isolated from cases of localized infections together with Hi. Both organisms are associated with sinusitis and exacerbations of asthmatic conditions [5,6]. Mx is the third most common cause of otitis media in children (estimated to be responsible for 3-4 million cases annually). It also causes lower respiratory tract infections in adults especially in patients with COPD [5]. On rare occasions, it has been associated with disseminated infections [5]. Both Hi and Mx cause persistent infections and are believed to escape host immune mechanisms and antibiotics by tissue penetration [4]. Several outer membrane proteins of Mx have been studied with respect to their adhesive properties. However, few cellular receptors for Mx have been identified and many of the details of pathogenic mechanisms remain to be investigated [4,5,6].

A primary requirement for respiratory mucosal pathogens is establishment of firm contact with respiratory epithelial cells. The targets of these human tropic pathogens are human specific molecules and studies have to rely on in vitro human tissue and organ cultures. The attachment is often mediated by bacterial phase- and antigenically-variable structures. In addition, it is becoming increasingly clear that attachment of pathogens is multi-faceted and environmental adaptation plays a significant role in the manner of attachment. Although many recent studies have begun to define various stages in the complex cellular targeting mechanisms, the details of environmental adaptation or host-microbial cross-talk remain to be described.

Recent studies by the present inventors have shown that Nm[7-9] and Hi[10,11] share some distinct and other common mechanisms of targeting certain human cell surface receptors CEACAMs[12]. Furthermore, the present inventors have recently identified that clinical isolates of *Moraxella catarrhalis* also target the human CEACAM molecules. In addition, it has now been found that a *Moraxella* outer membrane protein of high molecular weight binds to the receptor. Expression of CEACAMs in distinct tissues[12] including respiratory epithelial cells has been demonstrated [24]. These observations imply that specific targeting of CEACAMs is of particular advantage to respiratory bacteria and may have arisen as a result of convergent evolution.

Amongst the adhesion factors elaborated by *Neisseria meningitidis* are pili (fimbriae)[13,14,16] and the outer membrane opacity proteins, Opa and Opc [15,16] Nm pili are long filamentous protein structures composed of multiple pilin subunits. They are generally regarded as the most important adhesins in capsulate bacteria[13,14,16] due the fact that capsule partly or totally masks outer membrane ligands resulting in their reduced functional efficacy, whilst pili traverse the capsule and remain functional in fully capsulate bacteria. Opa are antigenically variable family of proteins and occur in *N. meningitidis* as well as *N. gonorrhoeae*. In meningococci, 3-4 opa gene loci code for related transmembrane proteins with four surface exposed loops, three of which undergo sequence variation [16,17]. Opc, another trans-membrane protein, is largely invariant[15,16]. Over the last 12 years, the present inventors have investigated structure/function relationships of Nm pili, the virulence potential of Opa and Opc proteins and identified two human receptors for the neisserial opacity proteins. Further, the role of surface sialic acids in bacterial interactions with human target cells as well as the role of LPS and other factors in cellular toxicity have been studied by the present inventors.

The present invention results from the identification by the inventors of a ligand of high molecular weight isolated from *Moraxella* outer membrane protein which binds to CEACAM receptors.

The ligand can be characterized by its SDS-PAGE migration pattern which is indicative of the USP-family of proteins in that it is broken down to monomers having a molecular weight of between approximately 60 and 150 kD when boiled for a prolonged period. The ligand has also been characterized in Mx strain ATCC 25238 (MX2) as UspA1 and its amino acid sequence determined. The ligand has been further characterized to determine the receptor binding region or domain, i.e. peptide or peptide-associated features that bind to the receptor.

Accordingly, the present invention provides a ligand isolated from *Moraxella catarrhalis* outer membrane protein which binds to CEACAM receptors, wherein said ligand is a polypeptide comprising or consisting of a receptor binding domain comprising or consisting of an amino acid sequence selected from the group consisting of residues 463 to 863, 527 to 623, 527 to 668, 527 to 863, 427 to 623, 427 to 668, and 427 to 863 of the sequence shown in FIG. 6, or a fragment, homologue, functional equivalent, derivative, degenerate or hydroxylation, sulphonation or glycosylation product or other secondary processing product thereof.

In a preferred embodiment, the ligand is a polypeptide comprising or consisting of an amino acid sequence selected from the group consisting of residues 527 to 623, 527 to 668, and 427 to 623 of the sequence shown in FIG. 6, or a fragment, homologue, functional equivalent, derivative, degenerate or hydroxylation, sulphonation or glycosylation product or other secondary processing product thereof.

The term ligand is used herein to denote both the whole molecule which binds to the receptor and any part thereof which includes the receptor binding domain such that it retains the receptor binding property. Thus "ligand" encompasses molecules which consist only of the receptor binding domain i.e. the peptide region or regions required for receptor binding.

In another preferred embodiment, the polypeptide comprises or consists of at least one of the conserved sequences from within the region 427 to 623 of the sequence shown in FIG. 6 which are identified in the alignment shown in FIG. 27. Hence, in this embodiment, the polypeptide comprises or consists of at least one of:

QHSSDIKTLK (SEQ ID NO: 8),
NVEEGLLDLSGRLIDQKADLTKDIK (SEQ ID NO: 9),
NVEEGLLDLSGRLIDQKADIAKNQA (SEQ ID NO: 10),
DIAQNQT (SEQ ID NO: 11),
DIQDLAAYNELQD (SEQ ID NO: 12),
QTEAIDALNKASS (SEQ ID NO: 13),
TAELGIAENKKDAQIAKAQANENKDGIAK (SEQ ID NO: 14),
NQADIQLHDKKITNLGILHSM-VARAVGNNTQGVATNKADIAK (SEQ ID NO: 15),
NQADIANNIKNIYELA (SEQ ID NO: 16),
NQADIANNI (SEQ ID NO: 17),
NIYELA (SEQ ID NO: 18).

It will be understood that the polypeptide ligands of the invention can comprise a receptor binding domain of sequence recited herein which is modified by the addition or deletion of amino acid residues to or from the sequences recited herein at either or both the N or C termini, which modified peptides retain the ability to bind CEACAM receptors. Accordingly, the invention further provides a ligand comprising or consisting of a polypeptide in which 50, 40, 30, 20, 10, 5, 3 or 1 amino acid residues have been added to or deleted from an amino acid sequence recited herein at either or both the N or C termini, wherein said modified polypeptide retains the ability to bind CEACAM receptors and/or elicit an immune response against the non-modified peptide. Preferably, the amino acid at position 560 is retained in the modified peptide.

As regards fragments of the polypeptides of the invention, any size fragment may be used in the invention provided that the fragment retains the ability to bind CEACAM receptors. It may be desirable to isolate a minimal peptide which contains only those regions required for receptor binding.

Polypeptide ligands according to the invention may be derived from known *Moraxella catarrhalis* UspA1 proteins by truncation at either or both of the N- and C-termini. Accordingly, the invention further provides a wild-type UspA1 sequence lacking at least (or exactly) 20, 30, 40, 50, 60, 70, 80, 100, 120, 140, 160 etc to 520 amino acids from the N-terminus, and/or lacking at least (or exactly) 20, 30, 40, 50, 60, 70, 80, 100, 120, 140, 160, 180 or 200 amino acids from the C-terminus. Preferably, the truncate retains CEACAM binding function. Possible truncates may be selected from those shown in the following table, all of which are within the scope of the invention.

TABLE I

Possible combinations of truncations to the N- and C-termini of wild-type UspA1 protein
No. of amino acids lacking, at least or exactly:

| From the N-terminus | | | | | | From the C-terminus | | | | | | | | |
|---|---|---|---|---|---|---|---|---|---|---|---|---|---|---|
| 0   | X | 20 | 30 | 40 | 50 | 60 | 70 | 80 | 100 | 120 | 140 | 160 | 180 | 200 |
| 20  | 0 | 20 | 30 | 40 | 50 | 60 | 70 | 80 | 100 | 120 | 140 | 160 | 180 | 200 |
| 30  | 0 | 20 | 30 | 40 | 50 | 60 | 70 | 80 | 100 | 120 | 140 | 160 | 180 | 200 |
| 40  | 0 | 20 | 30 | 40 | 50 | 60 | 70 | 80 | 100 | 120 | 140 | 160 | 180 | 200 |
| 50  | 0 | 20 | 30 | 40 | 50 | 60 | 70 | 80 | 100 | 120 | 140 | 160 | 180 | 200 |
| 60  | 0 | 20 | 30 | 40 | 50 | 60 | 70 | 80 | 100 | 120 | 140 | 160 | 180 | 200 |
| 70  | 0 | 20 | 30 | 40 | 50 | 60 | 70 | 80 | 100 | 120 | 140 | 160 | 180 | 200 |
| 80  | 0 | 20 | 30 | 40 | 50 | 60 | 70 | 80 | 100 | 120 | 140 | 160 | 180 | 200 |
| 100 | 0 | 20 | 30 | 40 | 50 | 60 | 70 | 80 | 100 | 120 | 140 | 160 | 180 | 200 |
| 120 | 0 | 20 | 30 | 40 | 50 | 60 | 70 | 80 | 100 | 120 | 140 | 160 | 180 | 200 |
| 140 | 0 | 20 | 30 | 40 | 50 | 60 | 70 | 80 | 100 | 120 | 140 | 160 | 180 | 200 |
| 160 | 0 | 20 | 30 | 40 | 50 | 60 | 70 | 80 | 100 | 120 | 140 | 160 | 180 | 200 |
| 180 | 0 | 20 | 30 | 40 | 50 | 60 | 70 | 80 | 100 | 120 | 140 | 160 | 180 | 200 |
| 200 | 0 | 20 | 30 | 40 | 50 | 60 | 70 | 80 | 100 | 120 | 140 | 160 | 180 | 200 |
| 220 | 0 | 20 | 30 | 40 | 50 | 60 | 70 | 80 | 100 | 120 | 140 | 160 | 180 | 200 |
| 240 | 0 | 20 | 30 | 40 | 50 | 60 | 70 | 80 | 100 | 120 | 140 | 160 | 180 | 200 |
| 260 | 0 | 20 | 30 | 40 | 50 | 60 | 70 | 80 | 100 | 120 | 140 | 160 | 180 | 200 |
| 280 | 0 | 20 | 30 | 40 | 50 | 60 | 70 | 80 | 100 | 120 | 140 | 160 | 180 | 200 |
| 300 | 0 | 20 | 30 | 40 | 50 | 60 | 70 | 80 | 100 | 120 | 140 | 160 | 180 | 200 |
| 320 | 0 | 20 | 30 | 40 | 50 | 60 | 70 | 80 | 100 | 120 | 140 | 160 | 180 | 200 |
| 340 | 0 | 20 | 30 | 40 | 50 | 60 | 70 | 80 | 100 | 120 | 140 | 160 | 180 | 200 |
| 360 | 0 | 20 | 30 | 40 | 50 | 60 | 70 | 80 | 100 | 120 | 140 | 160 | 180 | 200 |
| 380 | 0 | 20 | 30 | 40 | 50 | 60 | 70 | 80 | 100 | 120 | 140 | 160 | 180 | 200 |
| 400 | 0 | 20 | 30 | 40 | 50 | 60 | 70 | 80 | 100 | 120 | 140 | 160 | 180 | 200 |
| 420 | 0 | 20 | 30 | 40 | 50 | 60 | 70 | 80 | 100 | 120 | 140 | 160 | 180 | 200 |
| 440 | 0 | 20 | 30 | 40 | 50 | 60 | 70 | 80 | 100 | 120 | 140 | 160 | 180 | 200 |
| 460 | 0 | 20 | 30 | 40 | 50 | 60 | 70 | 80 | 100 | 120 | 140 | 160 | 180 | 200 |
| 480 | 0 | 20 | 30 | 40 | 50 | 60 | 70 | 80 | 100 | 120 | 140 | 160 | 180 | 200 |
| 500 | 0 | 20 | 30 | 40 | 50 | 60 | 70 | 80 | 100 | 120 | 140 | 160 | 180 | 200 |
| 520 | 0 | 20 | 30 | 40 | 50 | 60 | 70 | 80 | 100 | 120 | 140 | 160 | 180 | 200 |

Known wild-type UspA1 sequences that may be truncated in this way are those of strains ATCC25238 (MX2; GenBank accession no. AAD43465), P44 (AAN84895), O35E (AAB96359), TTA37 (AAF40122), O12E (AAF40118), O46E (AAF36416), V1171 (AAD43469), TTA24 (AAD43467) (see Example 10, Table II). Ideally the UspA1 truncate of this embodiment comprises or consists of an amino acid sequence selected from the group consisting of residues 463 to 863, 527 to 623, 527 to 668, 527 to 863, 427 to 623, 427 to 668, and 427 to 863 of the sequence shown in FIG. 6, or a fragment, homologue, functional equivalent, derivative, degenerate or hydroxylation, sulphonation or glycosylation product or other secondary processing product thereof; or comprises or consists of at least one of the conserved sequences from within the region 427 to 623 of the sequence shown in FIG. 6 which are identified in the alignment shown in FIG. 27, for example:

QHSSDIKTLK (SEQ ID NO: 8),
NVEEGLLDLSGRLIDQKADLTKDIK (SEQ ID NO: 9),
NVEEGLLDLSGRLIDQKADIAKNQA (SEQ ID NO: 10),
DIAQNQT (SEQ ID NO: 11),
DIQDLAAYNELQD (SEQ ID NO: 12),
QTEAIDALNKASS (SEQ ID NO: 13),
TAELGIAENKKDAQIAKAQANENKDGIAK (SEQ ID NO: 14),
NQADIQLHDKKITNLGILHSM-VARAVGNNTQGVATNKADIAK (SEQ ID NO: 15),
NQADIANNIKNIYELA (SEQ ID NO: 16),
NQADIANNI (SEQ ID NO: 17),
NIYELA (SEQ ID NO: 18).

It may be convenient to produce fusion proteins containing polypeptide ligands as described herein. Accordingly, in a further embodiment, the invention provides fusion proteins comprising polypeptide ligands according to the invention. Preferably a fusion protein according to this embodiment is less than 50% identical to any known full length sequence over its entire length.

Homologous peptides may be identified by sequence comparison. Homologous peptides are preferably at least 60% identical, more preferably at least 70%, 80%, 90%, 95% or 99% identical in ascending order of preference to the peptide sequences disclosed herein or fragments thereof over their entire length. Preferably the homologous peptide retains the ability to bind CEACAM receptors and/or elicit an immune response against the peptide sequences disclosed herein or fragment thereof. Preferably the amino acid at position 560 or homologous position is lysine.

FIG. 20 shows an alignment of peptide sequences of different origin which indicates regions of sequence that are capable of being modified whilst retaining function (i.e. CEACAM binding ability).

The inventors have determined that the CEACAM binding ability of the peptide ligand is associated with an α-helical based conformation as determined by circular dichroism (CD) spectroscopy, as opposed to a random coil structure. Accordingly, in a preferred embodiment, the peptide ligand or receptor binding domain of the invention or fragment or homologue or other derivative thereof adopts an α-helical structure. Optionally, the structure is a coiled coil structure. Preferably, CD spectroscopy is performed as described in the accompanying examples.

In a further embodiment, the invention provides peptides which are structurally homologous to the peptides disclosed herein or fragments thereof. A structurally homologous peptide is a homologous peptide as described above which gives a circular dichroism (CD) spectroscopy trace indicative of an α-helical based conformation as shown in FIG. 18. Mimotopes of the peptides disclosed herein or fragments thereof are also envisaged. Mimotopes may comprise D-amino acids or non-natural amino acid substitutions but still retain the functional characteristics of the peptides disclosed herein, including a CD trace indicative of an α-helical based conformation.

The α-helical based conformation revealed by the inventors indicates that the peptides disclosed herein possess a globular sub-unit structure that does not rely on an associated membrane to achieve the appropriate conformation for CEACAM binding.

Accordingly, in a still further embodiment, the invention provides a globular sub-unit molecule comprising the peptide ligand or receptor binding domain of the invention which is not a full-length UspA1 protein and which is capable of binding CEACAM receptors without the need for an outer membrane to be present. Preferably the globular sub-unit molecule comprises less than 200 amino acids, more preferably less than 100 amino acids.

Structurally and/or functionally equivalent receptor binding domains may also occur in other UspA-like proteins since hybrid proteins occur in Mx that may contain mosaic epitopes derived from both UspA 1 and UspA2 proteins[23]. Ligands comprising such equivalent receptor binding domains are also within the scope of the invention.

The CEACAM binding property of the peptide ligand means that it has utility as both an antigen (i.e. in a vaccine) and as an "antibiotic" whereby it is administered in order to block CEACAM binding and so prevent binding and entry of the pathogen.

Hence, the ligand or receptor binding domain is preferably suitable for use in the prevention or treatment of infection.

The present invention also provides a nucleic acid sequence encoding the ligand protein of the present invention together with homologues, fragments, polymorphisms, degenerates and splice variants thereof.

The ligand of the invention, or combinations thereof may be used in a vaccine or other prophylactic treatment of infection.

The vaccine or other prophylactic treatment may comprise any known adjuvant, vehicle, excipient, binder, carrier, preservatives and the like, to provide a pharmaceutically acceptable preparation of the ligand for use in the treatment of a patient.

The invention also provides a pharmaceutically acceptable preparation of the ligand for use in medicine.

The pharmaceutically acceptable preparation of the ligand may be used in the treatment or prevention of any disease where CEACAM receptors are implicated, for example in the treatment or prevention of infection, respiratory disease, neoplastic diseases and associated conditions of neoplastic diseases, and angiogenesis.

Preferably, where an infection is treated, the infection is of, or has occurred via, the mucosal membrane, especially a respiratory infection.

More preferably, the ligand is used as a vaccine for or in other prophylaxis or treatment of *Neisseria meningitidis*, *Haemophilus influenzae* and *Moraxella catarrhalis*. Ideally, the ligand is used as a vaccine for or in other prophylaxis or treatment of otitis media.

In a further aspect, the ligand of the present invention may also be used to identify novel blocking reagents for use as therapeutic agents to protect vulnerable groups and the public in general against several mucosal pathogens. For example the ligand may be used to identify receptor analogs which are useful for this purpose.

Hence the present invention also provides a screening assay for the identification of novel blocking reagents for use as therapeutic agents, the assay comprising the steps of screening potential therapeutic agents for their ability to mimic or for their homology to the ligand of the present invention. The invention further provides therapeutic agents identified by the aforementioned screening assay.

Effective vaccine components may be produced by using the information of the receptor targeting mechanisms identified by the present invention such as biologically active peptide mimics. These could prevent bacterial colonization/invasion of mucosa as well as elicit antibodies which may be blocking, opsonic and bactericidal.

Bacterially derived biologically active peptide sequences identified by the ligand of the present invention could be used to study the roles of CEACAMs in cancer and development as the molecules are associated with these processes. These also have potential as anti-cancer agents and to control or otherwise in the treatment of angiogenesis.

The information generated by the inventors regarding the conformation of the peptide ligand of the invention could be used to design a synthetic nano-structure e.g. from plastic. Such a structure would have the advantages of being resistant to biological degradation and non-immunogenic. As such it would be particularly useful as an "antibiotic" acting to prevent binding and entry of pathogen by blocking CEACAM receptors.

In a further embodiment, the invention provides the use of a CEACAM receptor-binding ligand in the manufacture of a medicament for the treatment or prophylaxis of a disease in which CEACAM receptors are involved in cellular targeting of the pathogen which causes the disease, wherein the ligand comprises or consists of an amino acid sequence selected from the group consisting of residues 463 to 863, 527 to 623, 527 to 668, 527 to 863, 427 to 623, 427 to 668, and 427 to 863 of the sequence shown in FIG. 6, or a fragment, homologue, functional equivalent, derivative, degenerate or hydroxylation, sulphonation or glycosylation product or other secondary processing product thereof.

Other ligands suitable for use in this aspect of the invention are polypeptides comprising or consisting of at least one of the conserved sequences from within the region 427 to 623 of the sequence shown in FIG. 6 which are identified in the alignment shown in FIG. 27, for example:

QHSSDIKTLK (SEQ ID NO: 8),
NVEEGLLDLSGRLIDQKADLTKDIK NO: (SEQ ID NO: 9),
NVEEGLLDLSGRLIDQKADIAKNQA (SEQ ID NO: 10),
DIAQNQT (SEQ ID NO: 11),
DIQDLAAYNELQD (SEQ ID NO: 12),
QTEAIDALNKASS (SEQ ID NO: 13),
TAELGIAENKKDAQIAKAQANENKDGIAK (SEQ ID NO: 14),
NQADIQLHDKKITNLGILHSM-VARAVGNNTQGVATNKADIAK (SEQ ID NO: 15),
NQADIANNIKNIYELA (SEQ ID NO: 16),
NQADIANNI (SEQ ID NO: 17),
NIYELA (SEQ ID NO: 18).

Preferably, the disease is selected from the group consisting of infection, respiratory disease, neoplastic disease and associated conditions of neoplastic disease, and angiogenesis.

Medicaments as described above are of particular utility where the pathogen infects, or enters via, a mucosal membrane. Medicaments as described herein are particularly useful in the treatment or prevention of infections (disease) caused by *Moraxella catarrhalis*. However, ligands as described herein are useful in the manufacture of medicaments for the treatment of any disease where CEACAM receptors are implicated such as diseases caused by *Neisseria meningitidis* and *Haemophilus influenzae*.

In a particularly preferred embodiment, the disease is otitis media.

Ligands of the invention may also be used in the treatment of diseases caused by other oral bacteria, such as dental caries.

The oral bacterium *Fusobacterium nucleatum* is associated with gum disease but has also been linked with otitis media, still births and in rare cases with bacteraemia. Recent work by the inventors has shown that several isolates of *Fusobacterium nucleatum* bind to CEACAMs and that binding of CEACAM1 to *F. nucleatum* can be inhibited by a polypeptide ligand as disclosed herein suggesting that ligands or receptor binding domains of the invention have utility in the treatment or prevention of diseases caused by this pathogen.

The ability of D-7, a preferred polypeptide ligand according to the invention, to block interactions of non-capsulate (not shown) or capsulate bacteria with HeLa-CC1H (Example 7), to block binding to multiple CEACAMs and its efficacy against a number of mucosal opportunist species (Example 7), makes it an anti-microbial agent with significant potential. In addition, its ability to evoke antibody response that block Mx adhesion (Example 8) suggests its potential as a vaccine candidate, alone or as a part of a multicomponent vaccine (together with other Mx antigens such as: UspA2, Hag/MID, OMPCD, Mcap) to prevent otitis media or lung infections in which Mx is often implicated [5]. Vaccines based on adhesins have been successfully used, for example against uropathogenic *Escherichia coli* in a mouse cystitis model by systemic vaccination [29].

Inclusion of a ligand according to the invention as a prophylactic drug may be considered in a variety of situations where the risk of acquiring particularly virulent or antibiotic resistant strains is high and may be delivered by direct topical application or via probiotics. In the case of bacteria that attach to target tissues via carbohydrate-lectin interactions, soluble carbohydrates have successfully prevented infections in in vitro and animal models [30,31,32]. Topical application of a synthetic peptide corresponding to a region of *Streptococcus mutans* protein SAI/II was shown to inhibit binding by *S. mutans* in human subjects. The study used peptide at 1 mg. $ml^{-1}$ in a mouthwash daily for 2 weeks and this was sufficient to prevent colonization [33]. Probiotics in the shape of lactobacilli have been used to prevent numerous infections [34,35]. In addition, a recombinant *E. coli* strain has been used as a probiotic in which LPS genes were modified to encode a structural mimic of the Shiga toxin receptor. Oral administration of this strain was shown to prevent death in mice from lethal challenge with shiga-toxin-producing E. coli[36]. Topically applied interfering peptides have a further advantage in that they can be delivered when and where required by the use of transitory probiotics or by expression vectors that can be controlled for the timing or the levels of expression. Thus the length of exposure to the anti-microbial agent can be controlled [37,38].

Interference by targeting the binding domain of the receptor, mimics bacterial adherence and is unlikely to have deleterious effect over and above that of binding of native commensal bacterial ligands. Also, such specific strategy ensures tolerance towards other commensal microflora, very few of which bind to CEACAMs[7,10,38]. Moreover, the monomeric and monovalent nature of the predominating form of the peptide is less likely to trigger undesirable signaling which, for CEACAMs, appears to be induced on receptor clustering [11,39].

Scope may exist for improvement of D-7 by further identifying critical amino acids involved in CEACAM interaction and modifications to reduce its size whilst ensuring binding as well as its longevity in vivo. Such modifications could include incorporation of unnatural or D-amino acids [33]. Resistance to such anti-adhesive/anti-invasive treatments is unlikely to occur since any changes in the bacterial ligand are likely themselves to lead to a loss of function and in this case colonization/infection. Emergence of mutants with completely altered receptor specificity due to peptide competition would not be expected to arise more frequently than usual since competition for the receptor is likely between the pathogens in the natural situation. Thus, D-7 has the potential to serve as an anti-adhesive agent against several pathogens and as a vaccine candidate.

Embodiments of the present invention will now be described purely by way of non-limiting example in which reference is made to the figures of which:—

FIG. 1 is a graph showing relative binding levels of CEACAM1-Fc (1 µg.ml$^{-1}$) soluble receptor construct alone (white, left hand bars), or in the presence of the CEACAM1 N-domain specific antibody YTH71.3 (grey, centre bars) to 3 strains of Mx immobilized on nitrocellulose. CD33-Fc binding in each case was negligible (black, right hand bars). Strains 1, 2, 3: MX2 (ATCC 25238), MX3, MX4 (clinical isolates) respectively. Binding was determined in a dot blot overlay and the intensity of reactions quantified by densitometric analysis using NIH Scion Image program.

FIG. 2 shows a Western blot of the strain MX2 proteins separated under undissociating (unheated, lane 1) or after boiling for 10 min. (lane 2). Blot was overlaid with CEACAM1-Fc (1 µg.ml$^{-1}$) and the receptor binding detected with anti-human Fc antibody conjugated to horseradish peroxidase and its substrate.

FIG. 3 shows Western blots of denatured whole cell lysates of strains MX2, -3, -4 (lanes 1-3 respectively) were overlaid with CEACAM1-Fc (1 µg. ml$^{-1}$; a), anti-UspA1 peptide antibody (10 µg.ml$^{-1}$; b) and anti-UspA2 peptide antibody (10 µg.ml$^{-1}$; c). Note the similar migration profile of CEACAM1-Fc binding proteins and anti-UspA1 binding proteins in the three strains. Remnants of undissociated proteins at c. 250 kDa, (detected in this case due to higher sensitivity of detection in the alkaline phosphatase assay), bind to CEACAM1-Fc. These are only weakly recognized by the anti-peptide antibodies, presumably since the epitopes contained within synthetic peptides are not fully exposed in the native protein, which become progressively exposed as the complex denatures. Anti-UspA2 antibodies bind to proteins of apparent masses >200 kDa, which remain undissociated after boiling, a property indicative of UspA2 proteins.

FIG. 4 shows a mass spectrum of tryptic peptides of the CEACAM1 binding protein of MX2 following electro-elution (4a). The summary of data input into the ProFound protein identification database is shown in (4b). A table of the top ten identified proteins and the probability values are shown in (4c). Detail of the number 1 ranked candidate, in this case UspA1 with a Z-score of 2.34 is shown in (4d) indicating the number of peptides matched, their positions within the protein, the % of the protein covered and a list of peptides unmatched on this occasion. SEQ ID NOS 19-29 are disclosed from top to bottom, respectively.

FIG. 5 shows Western blot analysis of tryptic fragments of UspA1 of MX2. A: control blot using secondary antibodies (mixture of goat anti-human Fc and goat anti-rabbit Ig used in B and C). B: blot overlaid with CEACAM1-Fc and goat anti-human Fc. C: blot overlaid with affinity purified rabbit antibodies raised against UspA1 peptide (ET-NNHQDQKIDQLGYALKEQGQHFNNR (SEQ ID NO:1)) (see FIG. 6) and anti-rabbit Ig. *=lanes with molecular weight markers—shown on the left. The peptides shown by the double arrows react strongly with CEACAM1-Fc (B) as well as the anti-UspA1 peptide antibodies (C). The binding of the anti-UspA1 peptide antibodies to the lowest MW peptide (arrowhead) identifies this CEACAM-binding fragment as the C-terminal fragment contained within N-199 to K-863 of UspA 1 of MX2 (see FIG. 6).

FIG. 6 shows the amino acid sequence of MX2 UspA1 protein (SEQ ID NO:2). UspA1-specific peptide used to raise antisera in rabbits is shown in bold. The CEACAM-binding region is contained in the underlined C-terminal fragment of UspA1 of MX2.

FIG. 7 shows the separation of tryptic peptides reacting with CEACAMs. M catarrhalis strain MX2 was treated with 1 mg/ml trypsin at 37° C. for 10 min. Trypsinized sample was subjected to SDS-PAGE. After staining, 50 kDa region was electroeluted overnight. Electroeluted protein was freeze dried and resuspended in buffer and applied to a second gel. Part of the gel was blotted onto nitrocellulose and peptide bands reacting with CEACAM were identified by Western blot overlay using CEACAM1-Fc (Blot).

'*' denotes peptide bands sent for N-terminal sequencing.

FIG. 8 shows the amino acid sequence of a tryptic peptide of MX2 UspA1 protein (SEQ ID NO:3). The 50 kDa tryptic peptide shown (amino acids 463 to 863) binds CEACAM and antiserum against UspA1 peptide (amino acids 753-780 underlined). The N-terminal sequence of the c. 50 kDa CEACAM binding peptide is "ALESNVEEGL" (SEQ ID NO:4) that occurs after the trypsin cleavage site at amino acid 462.

FIG. 9 shows a diagrammatic representation of the positions of primers used to generate uspA1 gene fragments for the expression of recombinant peptides. The CEACAM1 binding site was encoded by DNA amplified by primers P4 and P7, additional primers throughout this region (letters A-I) were designed and employed.

FIG. 10 shows the sequence of the recombinant fragment 4-7 (SEQ ID NO:5). The underlined region is the N-terminal region of the CEACAM1-reactive tryptic peptide. The predicted molecular weight of the fragment 4-7 is c. 26 kDa. The predicted MW of the His-tagged fragment: c. 28 kDa. The position of the truncated peptide is shown by 'T' (see FIG. 13).

Figure 13:
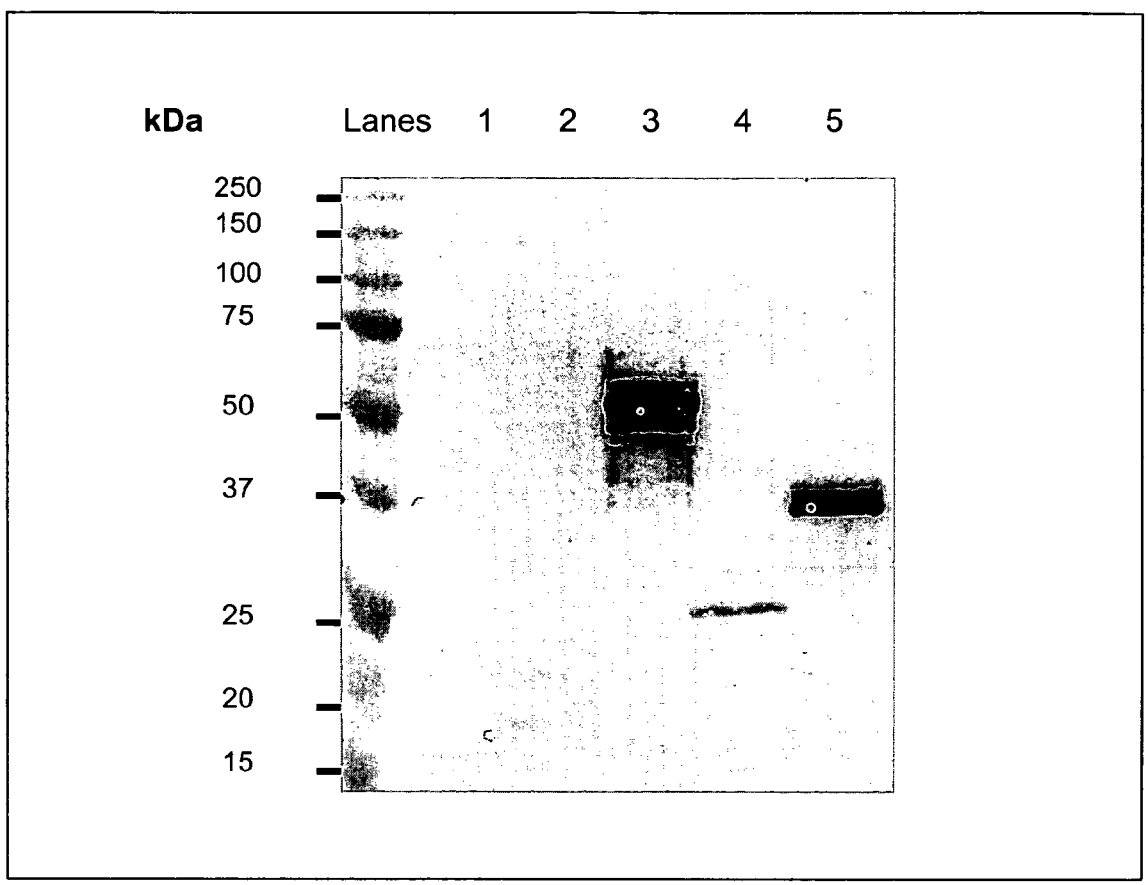

FIG. 13 shows binding of CEACAM1-Fc in blot overlay to recombinants 4-8 (lane 3), 4-T (lane 4) and 4-7 (lane 5) polypeptides. Lane 1 contained a Treponemal control recombinant peptide and lane 2 contained lysates of non-induced M15 containing 4-8 construct.

Figure 14:
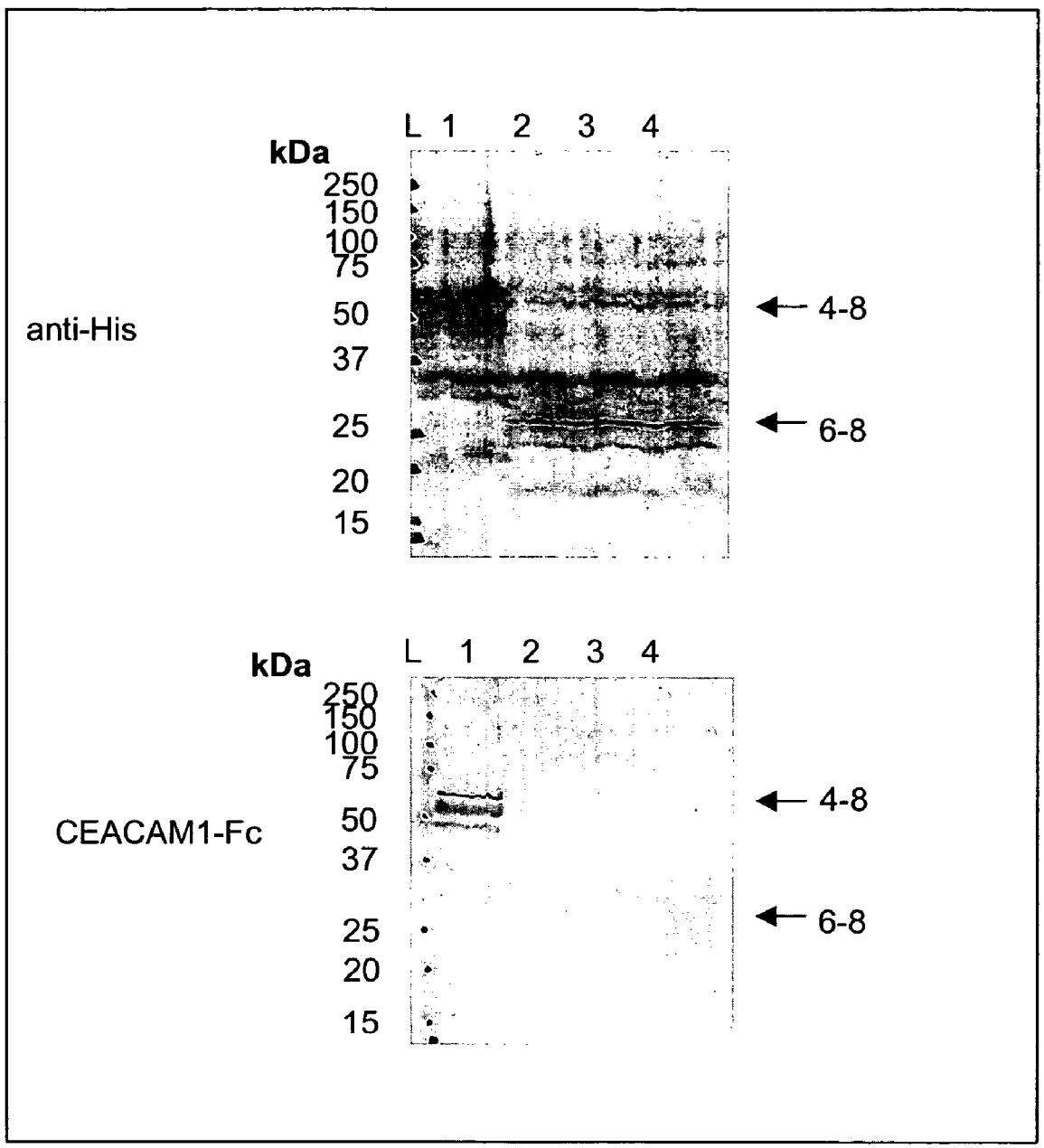

FIG. 14 shows Western blots showing recombinant peptide reactivity with anti-His tag antibody (top) and CEACAM1-Fc (bottom). Lanes 2-4 contained 6-8 peptide, lane 1 contained 4-8 as a control. Predicted migration positions of the peptides are shown on the right. Both peptides bind anti-His antibody. However, whilst 4-8 binds to CEACAM1-Fc, 6-8 does not.

Figure 15:
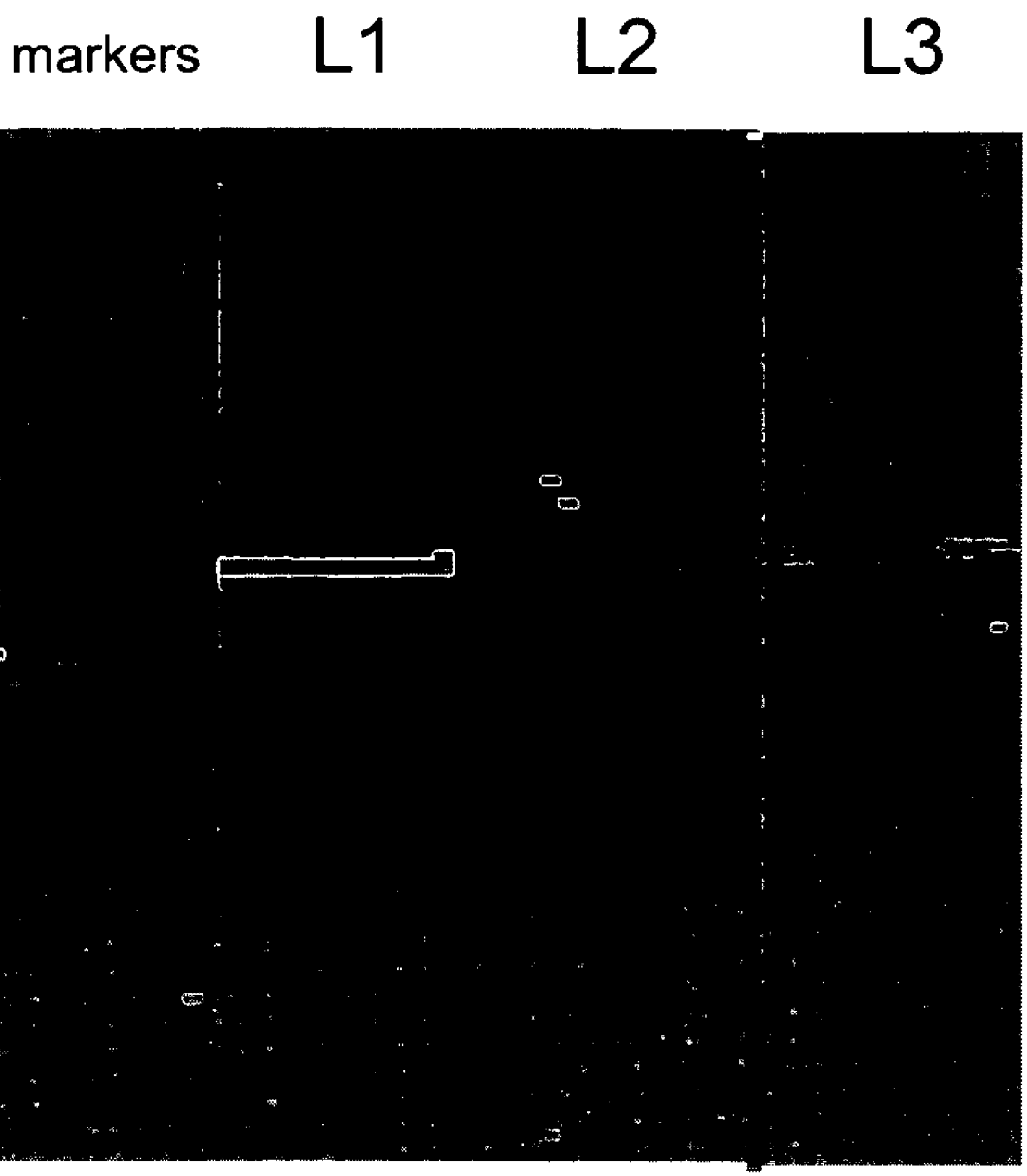

FIG. 15 shows that D-8 polypeptide binds CEACAM1-Fc (lane 1) but not CD33-Fc used as a control (lane 2). The origin of this peptide was confirmed by reactivity with the anti-His tag antibody (lane 3).

Figure 16:
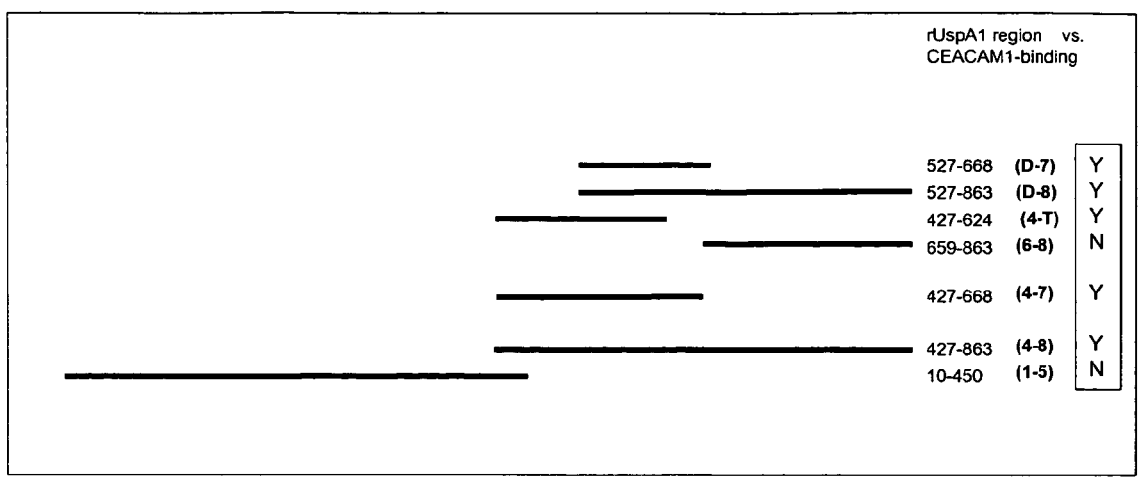

FIG. 16 is a schematic diagram showing the relative sizes and positions of rUspA1 fragments. Recombinant 4-7 has been used for bacterial blocking—see FIG. 17.

Figure 17:
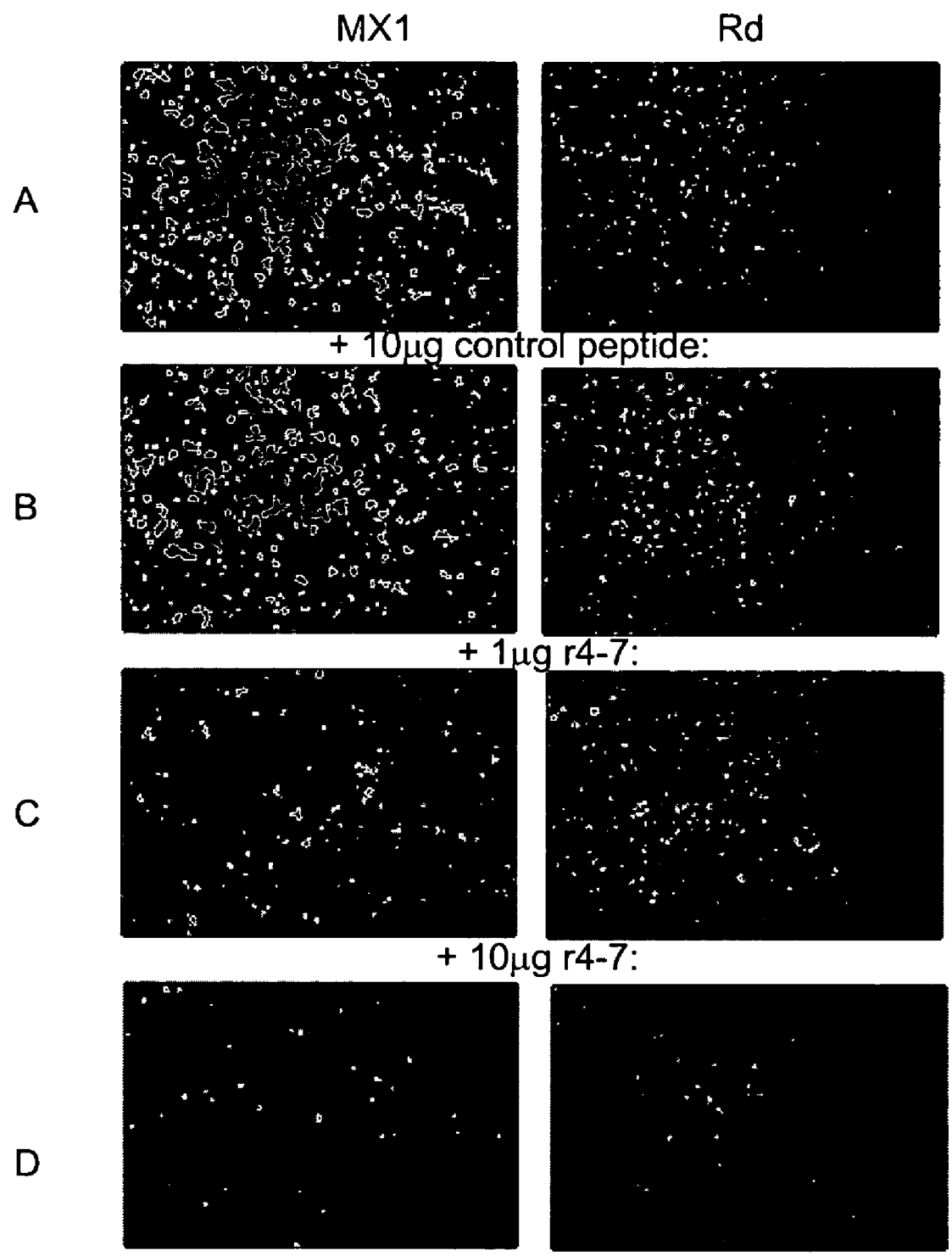

FIG. 17 shows CHO-CEACAM1 transfectants were incubated in the absence of peptides (A) or with recombinant control peptide (a treponemal peptide, B) or UspA1 r4-7 peptide (sequence corresponding to the strain MX2, C and D) at the concentrations shown and bacteria added for a period of 2 hours. At the end of this incubation, unbound bacteria were washed off and bound bacteria detected with anti-M. catarrhalis polyclonal antiserum and TRITC conjugated secondary antibody. At 1 μg/ml significant inhibition of a heterologous M. catarrhalis strain (MX 1) was obtained and at 10 μg per ml, H. influenzae binding was significantly inhibited by M. catarrhalis UspA1 recombinant peptide.

Figure 18:
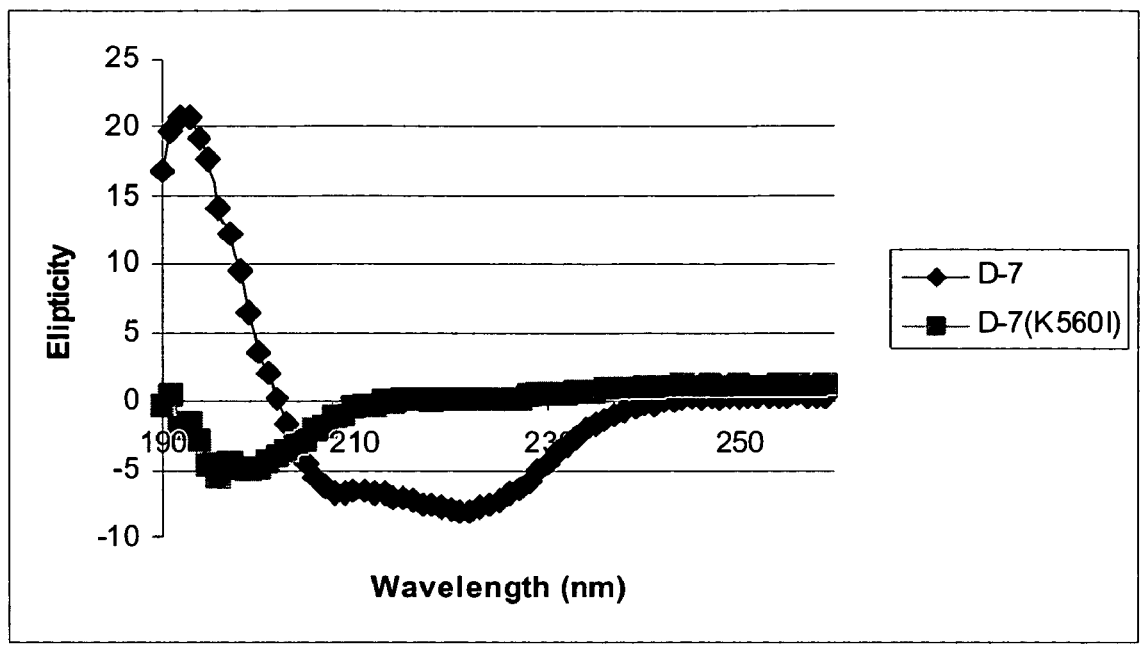

FIG. 18 is a graph showing the circular dichroism spectra of recombinant D-7 peptide and D-7 with K 560 I mutation. The spectra indicate that D-7 has an α-helical structure whereas D-7 (K 560 I) adopts a random coil formation.

FIG. 19 shows a series of linear peptides spanning the D-T region which do not bind CEACAM1 (SEQ ID NOS 29-39 are disclosed from top to bottom, respectively). The K residue corresponding to K560 of D-7 is underlined.

FIG. 20 is an alignment of the D-7 region of the amino acid sequences of the UspA1 proteins of ten strains of Mx: TTA24 (SEQ ID NO: 42), TTA37 (SEQ ID NO: 43), p44 (SEQ ID NO: 44), O12E (SEQ ID NO: 45), 035E (SEQ ID NO: 46), O46E (SEQ ID NO: 47), MX2 (SEQ ID NO: 48), V1171 (SEQ ID NO: 49), MX3 (SEQ ID NO: 50) and MX4 (SEQ ID NO: 51). The top line shows the majority sequence (SEQ ID NO: 41).

FIG. 21 is a manual alignment of O35E D-7 (SEQ ID NO: 46) versus MX2 D-7 (SEQ ID NO: 48). The top line shows the majority sequence (SEQ ID NO: 60).

FIG. 22 is a table showing sequence identity of D-7 regions of Mx isolates as determined by MegAlign™ (DNASTAR Inc.).

Figure 23:
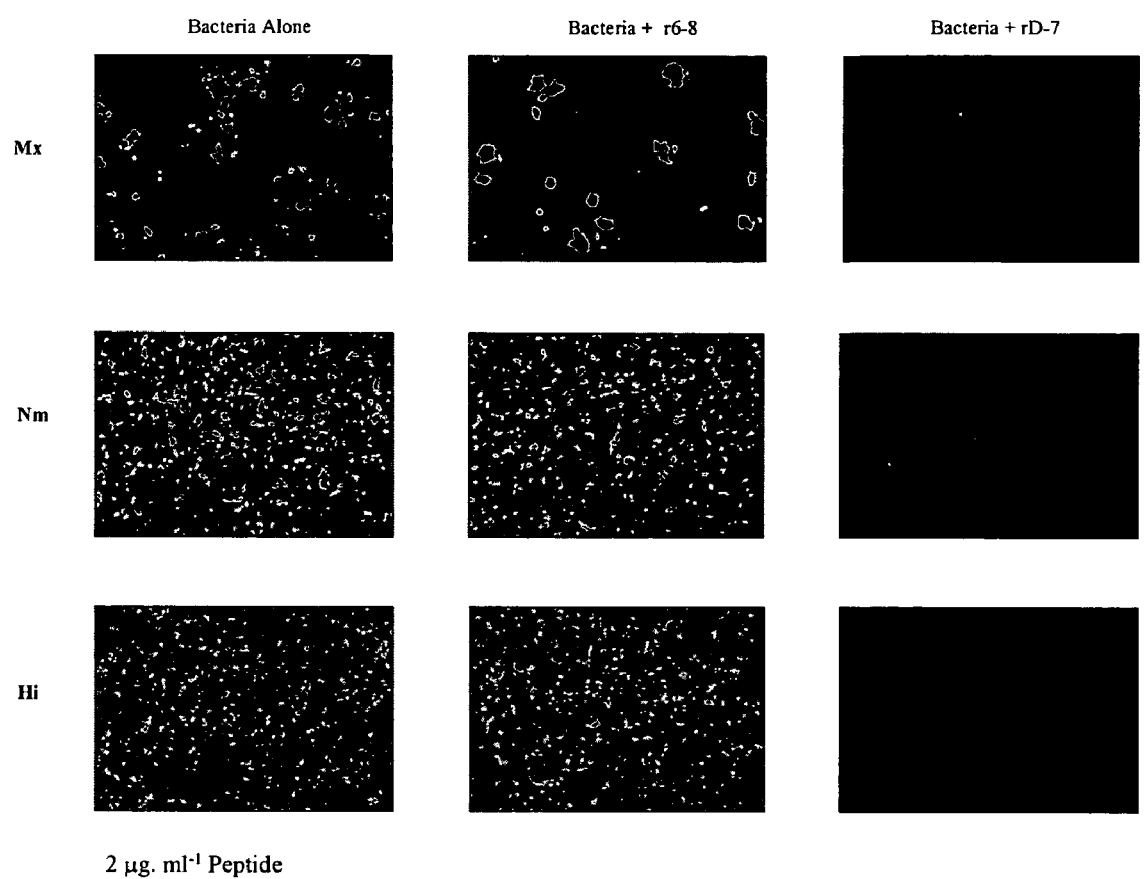

FIG. 23 shows recombinant peptide D-7 (but not recombinant 6-8 i.e. residues E659-K863 of UspA1 of MX2) inhibits binding of both homologous and heterologous strains to transfected CHO cells expressing CEACAM1. Following preincubation of cells with either no peptide (column 1), control peptide (2 μg.ml$^{-1}$; column 2), or D-7 (2 μg.ml$^{-1}$; column 3) bacteria were added and non-adherent bacteria removed by washing after 1 h incubation. Bacteria associated with cells were then detected using antisera raised against distinct strains and rhodamine conjugated secondary antibodies. Mx: Moraxella catarrhalis, Nm. Neisseria meningitidis; Hi: Haemophilus influenzae.

Figure 24A:
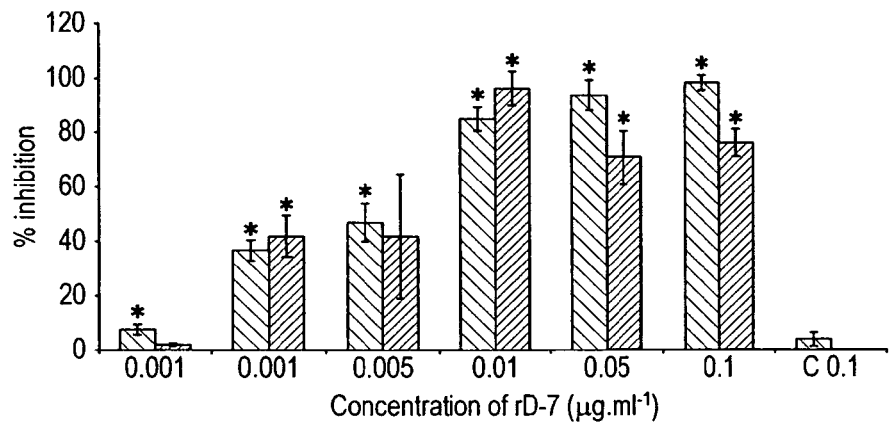
Figure 24B:
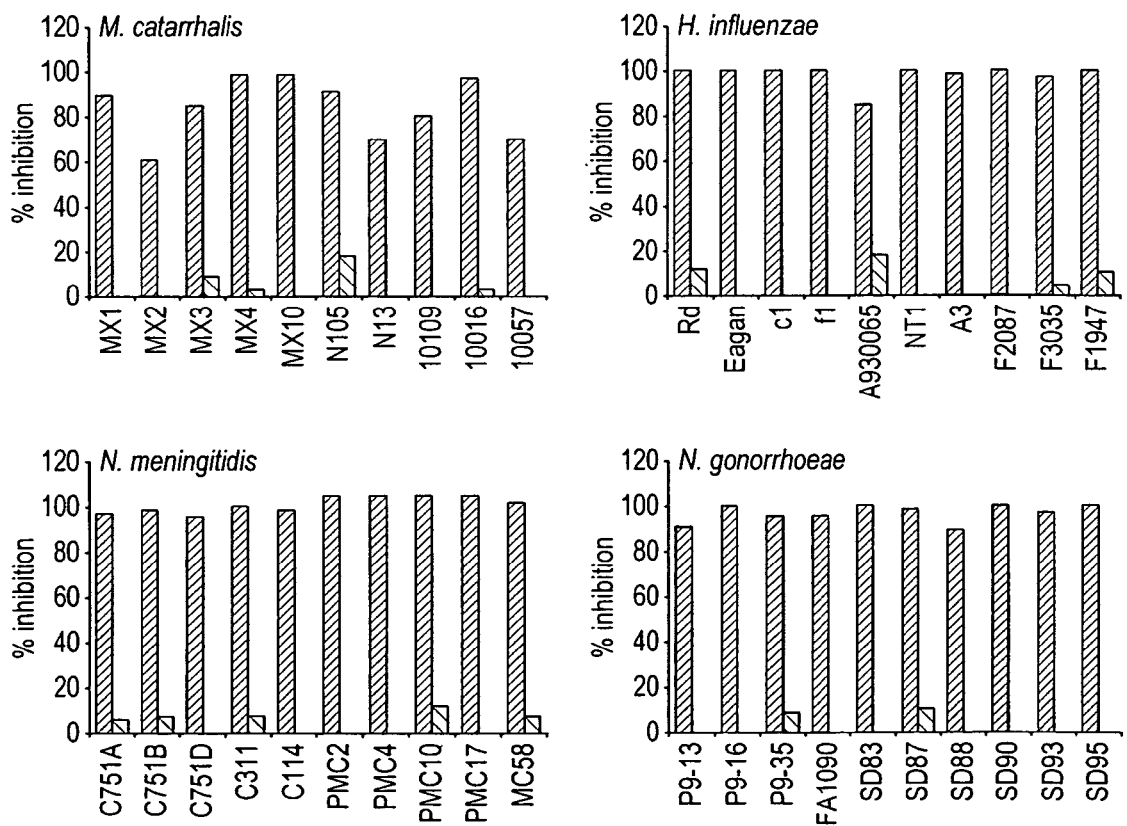
Figure 25A:
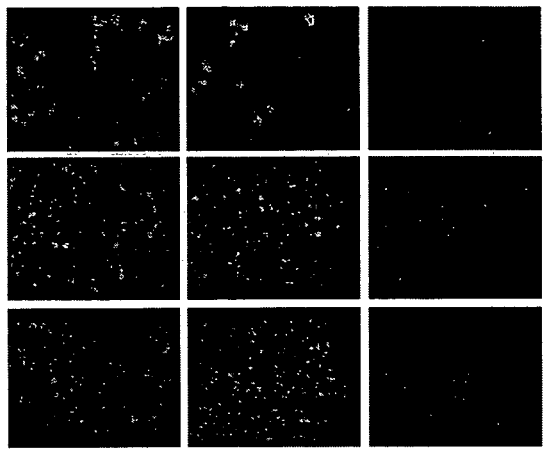
Figure 25B:
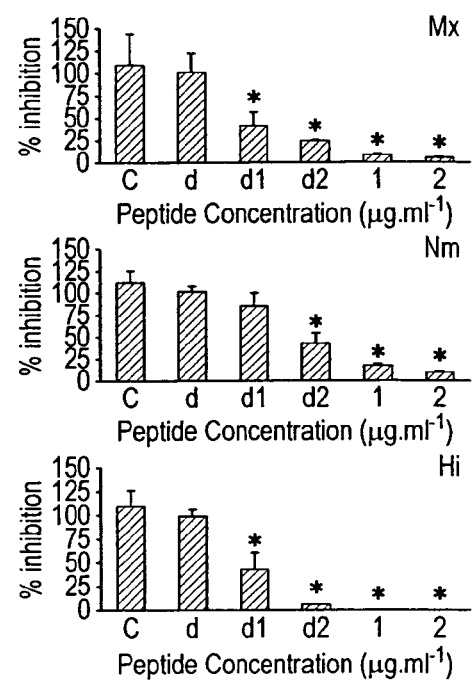
Figure 25C:
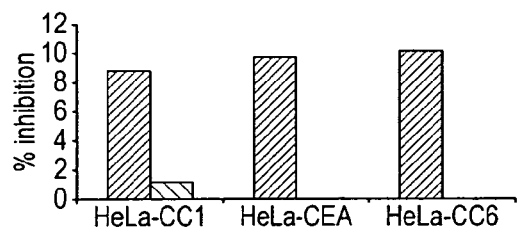
Figure 25D:
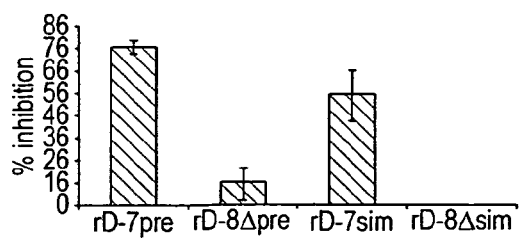
Figure 25E:
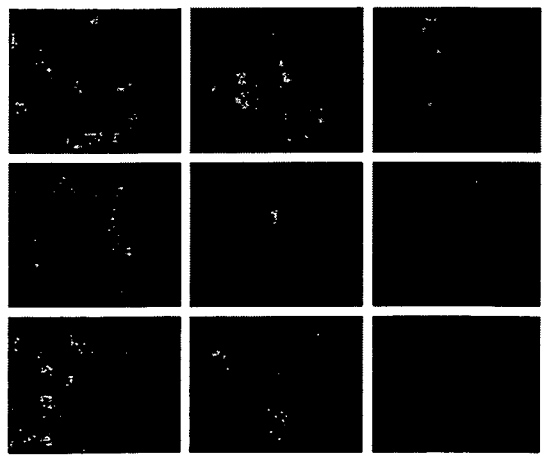

FIG. 24 is a series of charts showing inhibition of bacterial-CC 1-Fc interactions by D-7. (a) A dose dependent inhibition of the receptor binding to the homologous Mx strain MX2 (grey columns) and to a heterologous strain MX1 (black columns) was displayed over the peptide concentration range 0.001-0.1 μg.ml$^{-1}$. C represents the control peptide D-8Δ. Mean values are shown n=3, *P<0.015 relative to CC1-Fc alone. (b) Recombinant D-7 (black columns) but not D-8Δ (grey columns) inhibits the binding of multiple strains of both homologous and heterologous species (as indicated above each graph) to CC1-Fc. Whole cell lysates of distinct isolates from different genera were dotted on to nitrocellulose and overlaid with CC1-Fc alone or in the presence of the peptides (2 $\mu g.ml^{-1}$ each). Percent inhibition values in the presence of the peptides relative to their absence were obtained by densitometric analysis using NIH Scion Image software. Data are representative of two to three independent experiments.

FIG. 25 shows that D-7 inhibits bacterial binding to a range of CEACAM expressing cell lines. (a) Immunofluorescence analysis of bacterial interactions with transfected CHO cells expressing CEACAM1 following preincubation of cells without or with peptides (2 $\mu g.ml^{-1}$) as indicated. Inhibition of the adherence of bacteria visualized by rhodamine labelling is observed in the presence of D-7. (b) Quantitative analysis of inhibition of bacterial binding to CHO-CEACAM1 cells using a viable count assay. Target monolayers were preincubated with control peptide (2 $\mu g.ml^{-1}$; C) or a range of D-7 as shown. Mean values of % inhibition with D-7 compared to the control peptide are shown (n=3-6, *P<0.05). Strains used in a and b were: Mx (MX1), Nm (C751D), Hi (THi, Rd) and Hi-aeg (A3), (c) Inhibition of Nm (C751D) binding to distinct CEACAMs by D-7. HeLa cells expressing CEACAM1 (CC1), CEA or CEACAM6 (CC6) were preincubated with either no peptide, control peptide (2 $\mu g.ml^{-1}$; grey columns), or D-7 (2 $\mu g.ml^{-1}$; black columns). Mean numbers of adherent Nm per cell were obtained using an immunofluorescence assay and by direct counting of 20 cells in each case. (d) A HeLa cell line with high levels of CEACAM1-expression (HeLa-CC1H) that supports adhesion via pili and Opa protein, was infected with h18.18, a capsulate and piliated derivative of strain MC58 expressing Opa and Opc adhesins. Cellular adhesion was reduced with prior (pre) or simultaneous (sim) addition of D-7 but not D-8Δ as indicated. (e) Inhibition of bacterial interactions with A549 lung epithelial cells known to express CEACAMs following preincubation of cells with either no peptide, control peptide (2 $\mu g.ml^{-1}$), or D-7 (2 $\mu g.ml^{-1}$) as indicated. Strains used were Mx (MX1), Nm (C751D) and Hi (Hi-aeg, A3).

Figure 26:
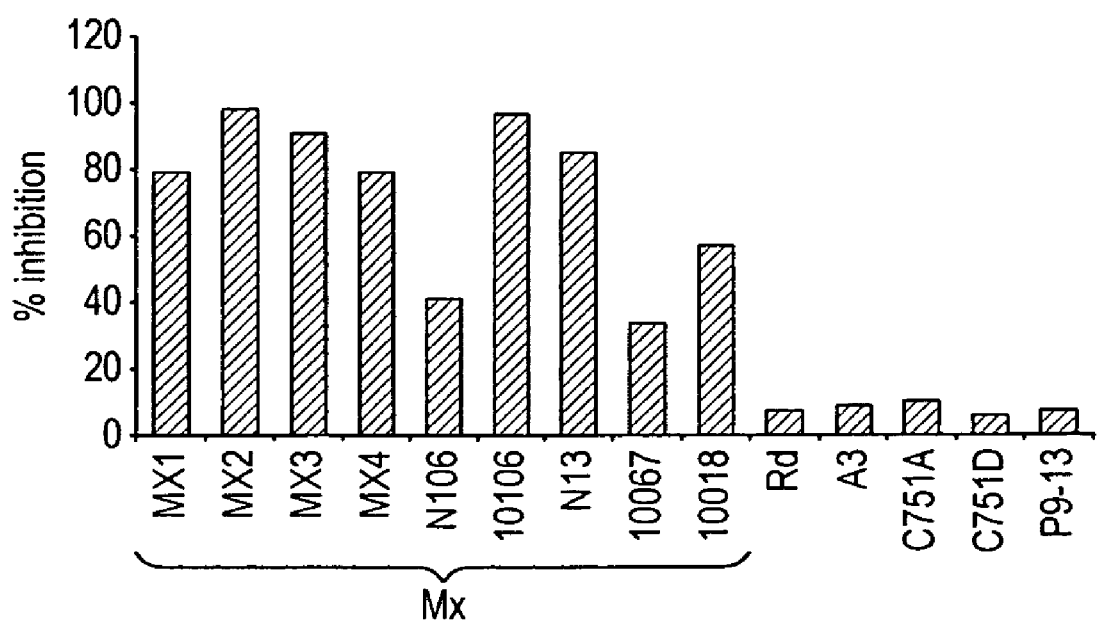

FIG. 26 is a chart showing that affinity purified rabbit antibody raised against D-7 inhibits both homologous and heterologous Mx binding to CEACaM1-Fc (CC1-Fc). In a dot-blot overlay experiment, binding relative to no antibody control was determined by densitometric analysis using NIH Scion Image software. Good inhibition is observed for the Mx strains tested but not so for other bacterial species tested including Hi (THi Rd & Hi-aeg A3), Nm (C751A & C751D) and Ng (P9-13). Data are representative of three independent experiments.

Figure 27:
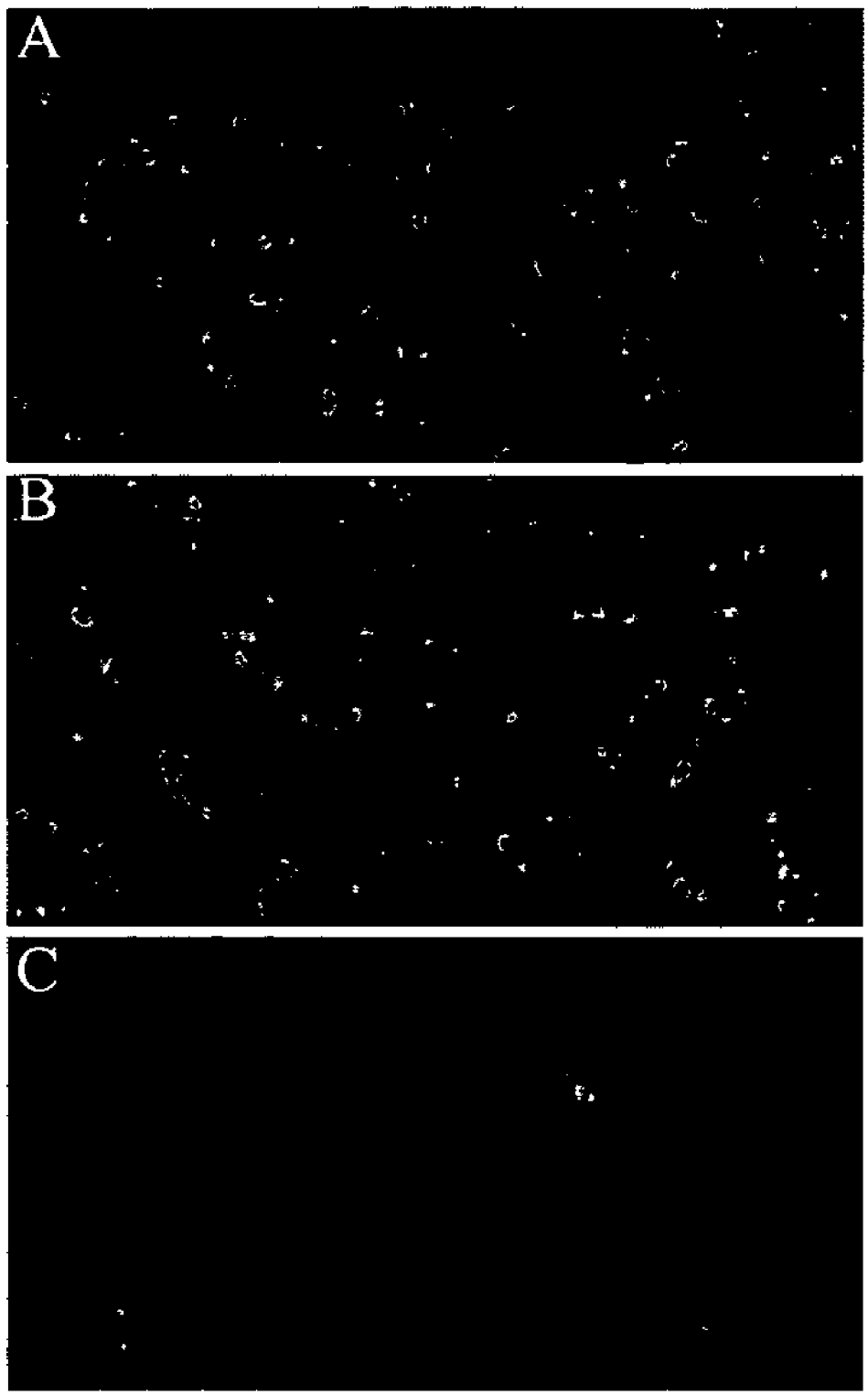

FIG. 27 shows adhesion of *N. meningitidis* to HMEC1 cells alone (A) or in the presense of control peptide (B) or the lbocking peptide D-7 (C). Note the virtual complete inhibition in the precense of D-7.

FIG. 28 is a multiple alignment of fragments of known UspA1 protein sequences corresponding to fragment 4-T of MX2 sequence. Residues that are conserved in all of the sequences analysed are shaded black. Residues that are conserved in all sequences where they are present, but there is a deletion of the corresponding position in one or more sequences are shaded dark grey. Where there is variation in the residue present at that position, the consensus residues are shaded light grey (SEQ ID NOS 52-59 are disclosed from top to bottom, respectively).

EXAMPLE 1

*Moraxella catarrhalis* Strains Bind to Human CEACAM1-Fc Via the UspA1 Proteins The strains of *Moraxella catarrhalis* (Mx) used in this study include clinical isolates (MX3 and MX4) as well as reference strain purchased from American Type Culture Collection (ATCC 25238, a clonal culture of this was designated MX2).

Receptor Overlay Assays show that Mx Bind to CEACAM1-Fc Receptor Constructs

To assess the interaction of *M. catarrhalis* strains with CEACAM1, bacteria (c. 4-8×$10^6$) were applied to nitrocellulose, air dried and non-specific binding sites blocked in 3% BSA-PBST. Nitrocellulose strips were overlaid with either CEACAM1-Fc (1-2 $\mu g\ ml^{-1}$) alone or in the presence of the CEACAM1 N-domain antibody YTH71.3. CD33-Fc (1-2 $\mu g\ ml^{-1}$) was used as a negative control. Chimeric protein constructs were prepared as previously described[11]. Chimeric receptor binding was detected by goat anti-human Fc antibodies conjugated to either horseradish peroxidase or alkaline phosphatase. Blots were developed with either diamino benzidene and hydrogen peroxide or nitroblue tetrazolium and 5-bromo-4-chloro-3-indoylphosphate substrates respectively. All Mx strains bound to CEACAM1-Fc but not to CD33-Fc (FIG. 1). The receptor binding was inhibited in the presence the monoclonal antibody YTH71:3 suggesting that the strains bound to the N terminal domain of the receptor. Accordingly, all the strains bound equally well to the truncated N-Fc construct of CEACAM1, containing only the N domain (not shown).

Identification of CEACAM1-Fc Binding Protein of *M. catarrhalis*

Figure 1:
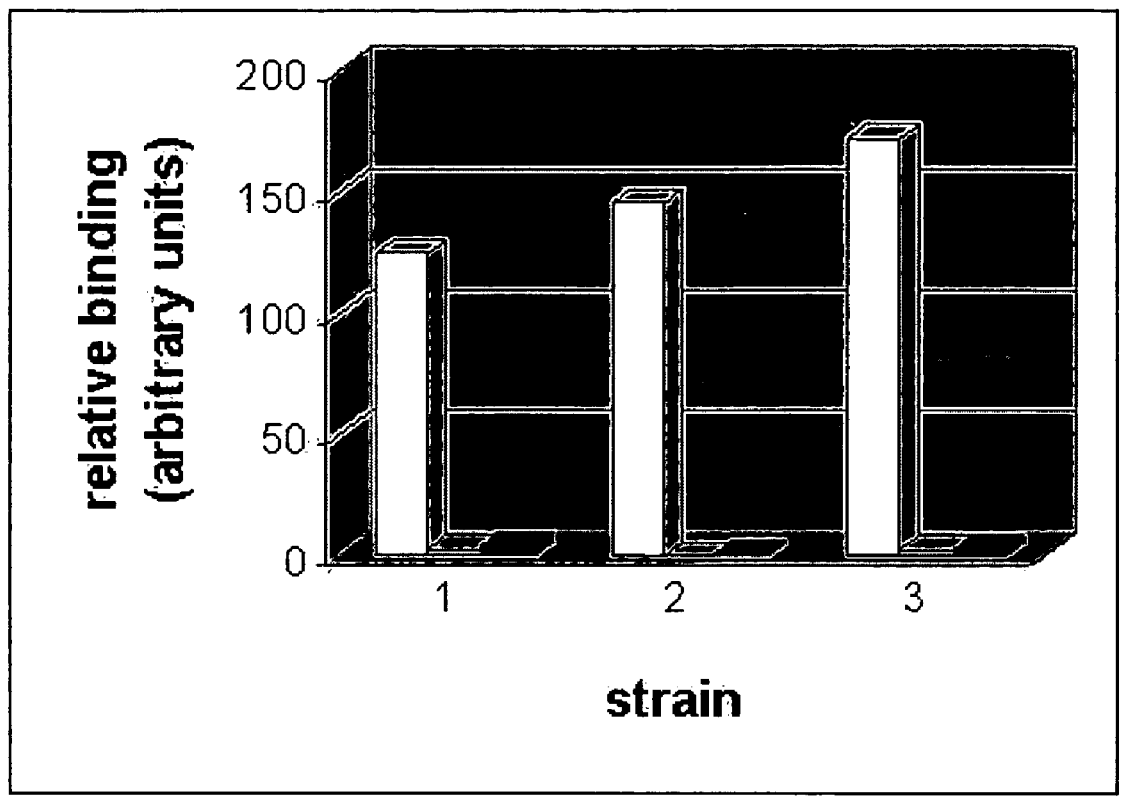
Figure 2:
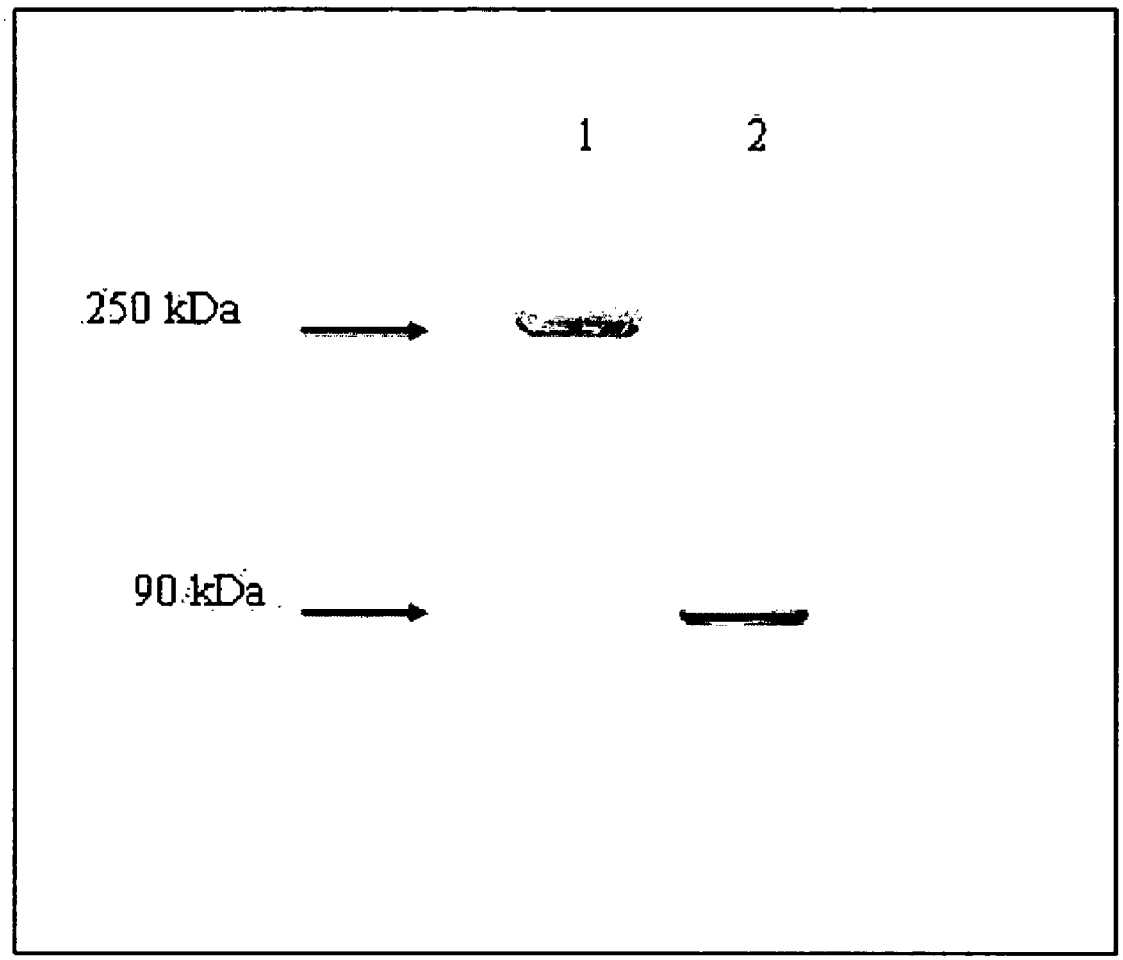
Figure 3:
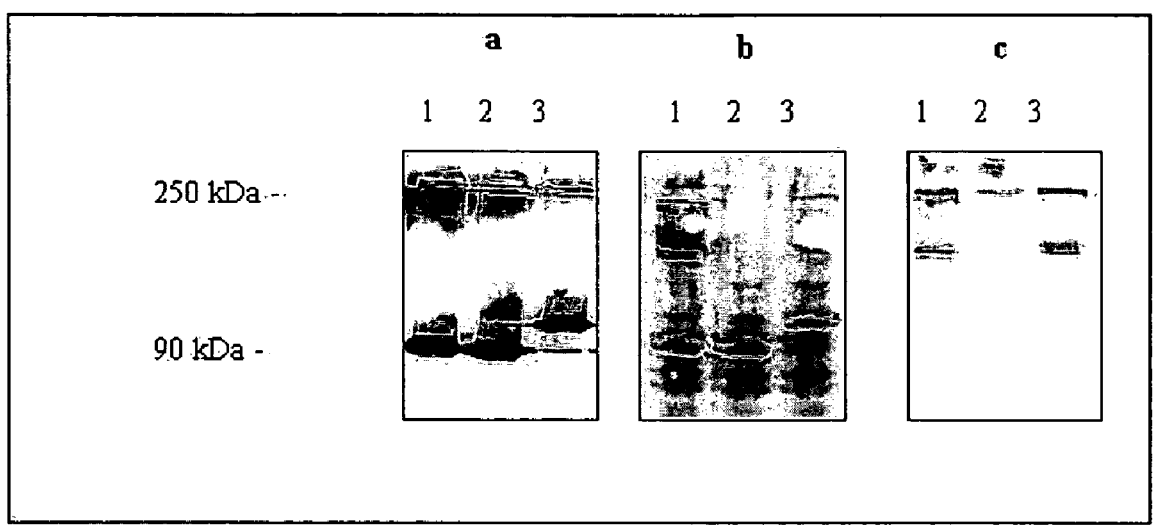

Whole cell lysates of Mx (c. 3×$10^7$) were applied to individual lanes of a 10% bis-tris polyacrylamide gel (Invitrogen) either without previous heat treatment or after heating at 100° C. for 10 minutes and subjected to electrophoresis for 45 min at 180 V. Proteins from the gels were transferred to nitrocellulose membranes using standard blotting conditions. Nitrocellulose membranes were overlaid with soluble chimeric constructs as described above. In each case, a single protein was observed that bound specifically to CEACAM1-Fc. The migration of the protein on gels was indicative of UspA1 protein of Mx, since when bacterial lysates were applied without heat denaturation, the CEACAM1 binding proteins migrated with an apparent mass of >200 kDa whereas when the lysates were first heated, the CEACAM1-binding-proteins migrated with a reduced mass of circa 92 kDa (FIG. 2)

Antibodies Raised Against UspA1 but not those Against a Similar Protein UspA2 Bind to the CEACAM1-Fc Binding Proteins of Mx Strains Peptides were designed according to published sequences for the UspA proteins of *M. catarrhalis* strains. Namely, ETNNRQDQKIDQLGYALKEQGQHFNNR (SEQ ID NO:1; UspA1-peptide) and KDEHDKLITANKTAIDANKAS (SEQ ID NO:6; UspA2-peptide). Peptides were coupled to KLH via an N-terminal cysteine residue that was incorporated and were used to immunise rabbits (200 μg peptide per rabbit) at 14 day intervals, initially with complete Freund's adjuvant and thereafter with incomplete Freund's adjuvant. Rabbits were bled at day 0 and at 14 day-intervals post immunization. Polyclonal antibodies were purified using the appropriate peptide coupled to AminoLink Plus columns (Pierce). UspA-specific antibodies were used at a concentration of 1-10 μg ml$^{-1}$ for Western blot overlays and detected with goat anti-rabbit secondary antibody coupled to alkaline phosphatase. Blots were developed as described earlier. The migration of the CEACAM1-Fc binding proteins on SDS-PAGE of the three Mx strains was identical to that of the UspA 1-antibody binding proteins but not UspA2-antibody binding proteins (FIG. 3)

*M. catarrhalis* Ligand co-precipitating with CEACAM1-Fc is Identified as UspA1

Overnight cultures of bacteria were suspended in 100 mM octyl βD glucopyranoside in PBSB containing a protease inhibitor cocktail (pic; PMSF 1 mM, E-64 1 μM, pepstatin A 1 μM, bestatin 6 nM and EDTA 100 μM). Samples were mixed end over end overnight at 4° C. Meanwhile 100 μl protein A coupled to sepharose CL-4B (Sigma) was incubated with either, 20 μg CEACAM1-Fc or CD33-Fc (used as a control) overnight at 4° C. and subsequently washed 3 times with PBSB to remove any unbound receptor. Insoluble bacterial material was removed by centrifugation at 15,000 g for 30 min. Soluble extract was incubated with either receptor-Protein A sepharose complex for 2 h at 4° C. (at a ratio of $5 \times 10^8$ bacteria per μg of receptor construct). Following extensive washing with 50 mM octyl βD glucopyranoside and PBSB samples were analysed by SDS-PAGE electrophoresis and Western Blotting under denaturing conditions.

In co-precipitation experiments with CEACAM1-Fc, MX4 yielded a strongly staining protein of c. 97 kDa and MX3 yielded a relatively weakly staining protein of c. 92 kDa. The masses of co-precipitated proteins corresponded to those observed in the receptor overlay experiments (shown in FIG. 3). Neither protein co-precipitated with CD33-Fc. The co-precipitated proteins were further identified as UspA1 proteins since they bound to anti-UspA1 peptide antibody. In addition, following excision from the gel, the MX4 protein was subjected to MALDI-TOF mass spectrometry (see below).

Figure 4A:
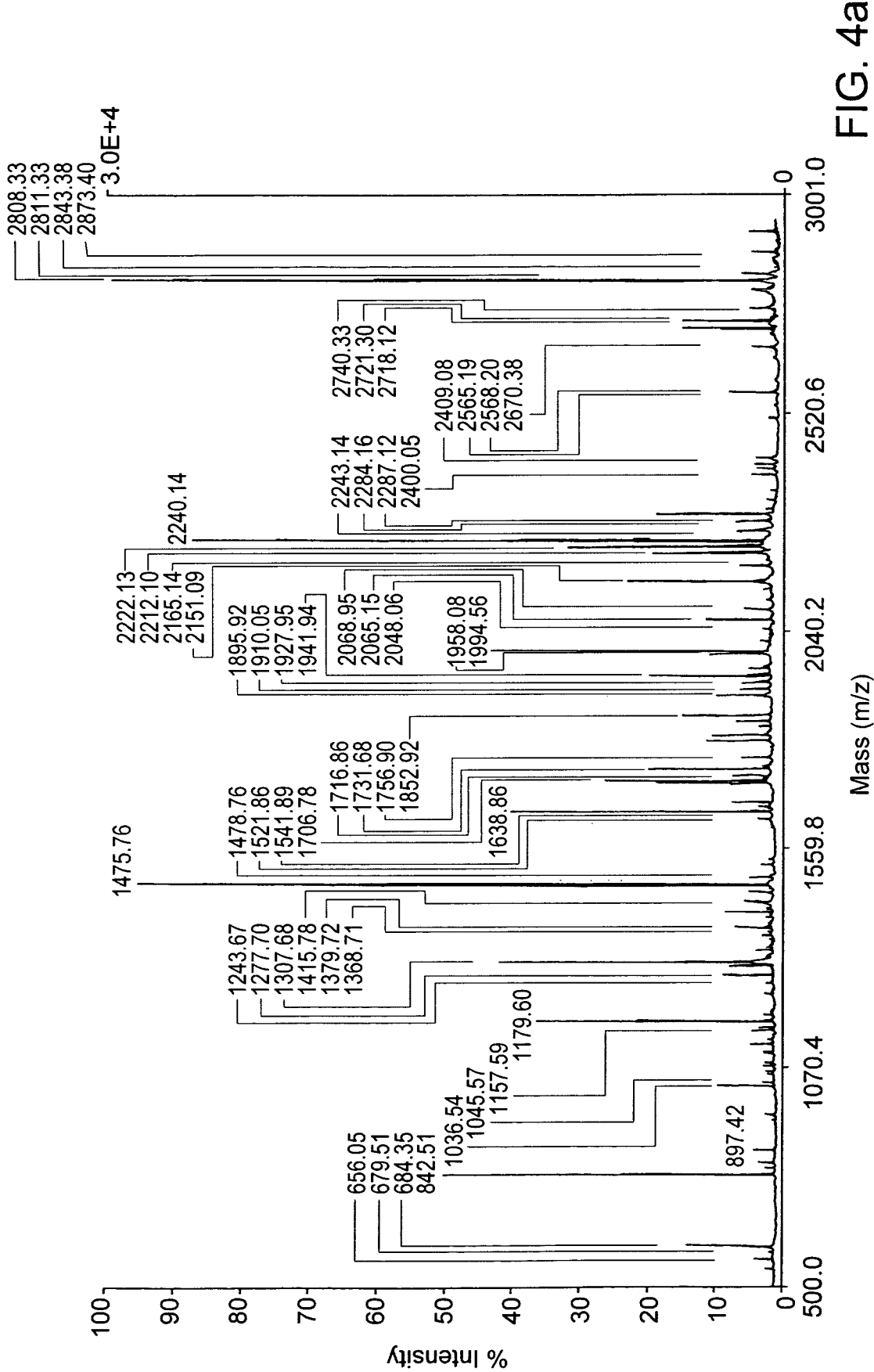
Figure 4D:

CEACAM1 Ligand Identification by MALDI-TOF Mass Spectrometry (a) Western overlay samples. Whole cell lysates of MX2 and MX3 were subjected to SDS-PAGE in trench gels and the protein band corresponding to CEACAM1-Fc binding ligand was electroeluted from the gel. The sample was concentrated and reapplied in a single lane of a second gel, subjected to electrophoresis prior to in-gel trypsin digestion of the appropriate protein. The resulting peptides were analysed by Matrix-assisted Laser desorption/ionization-time-of-flight (MALDI-TOF) mass spectrometry. An example of the resulting mass spectrum is shown for the CEACAM binding protein of MX2 (FIG. 4a). The peptide masses obtained were entered into the ProFound protein identification site and the results were obtained as shown for this protein (FIG. 4b, c). In this case 10 peptide masses were matched to predicted masses for tryptic peptides of UspA1 of M catarrhalis covering approximately 18% of the protein (FIG. 4d). The estimated Z score of 2.34 is strongly suggestive of the protein being UspA 1 (Z score >1.65 are above the 95$^{th}$ percentile;

http://129.85.19.192/profound_bin/webProFound.exe). In addition, another non-binding high molecular weight band of MX2 was identified as UspA2 following a similar analysis. Similarly for strain MX3, the CEACAM1 binding and non-binding proteins were identified as UspA1 and UspA2 respectively.

(b) Co-precipitated samples: For MX4, the CEACAM1-Fc co-precipitated protein (as described above) was also identified as UspA1 by MALDI-TOF MS with a Z score of 2.27 in an all taxa search. 12 peptides were matched covering 21% of the protein.

This study therefore has identified that *Moraxella catarrhalis* targets human CEACAM1 via the high molecular weight protein UspA1 in the reference and clinical strains indicated.

Figure 5:
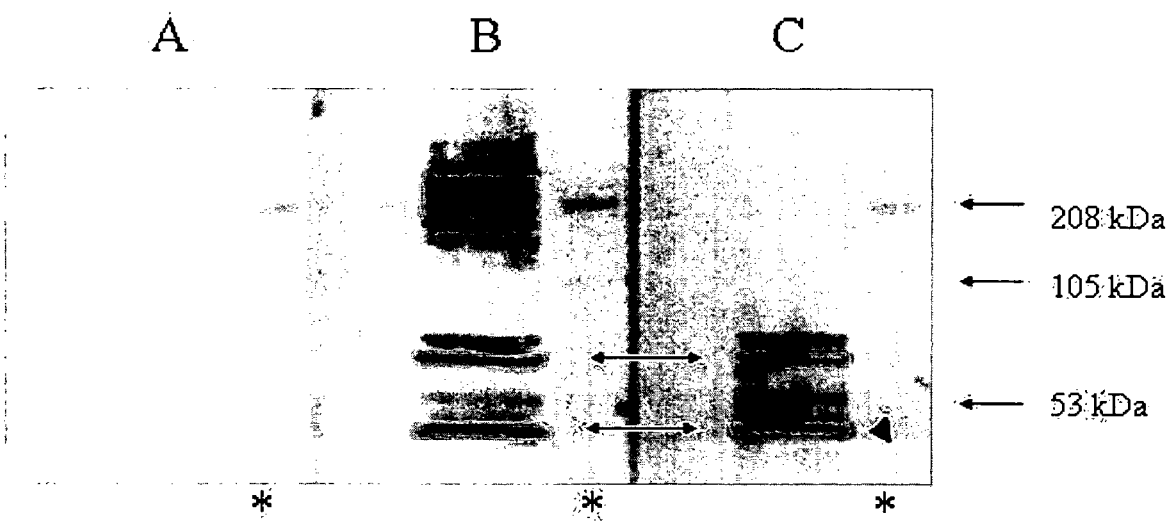

Enzymatic Cleavage of UspA1 and Recombinant Peptide (a) Tryptic Peptides of UspA1 Bind to CEACAM1-Fc MX2 bacterial suspensions (10$^{10}$ ml$^{-1}$) were treated with Trypsin (Sigma) at 0.1-1 mg/ml concentrations and incubated for 1-4 hours at 37° C. Digested lysates were dissociated in SDS-PAGE buffer, boiled and subjected to electrophoresis. After transfer to nitrocellulose, the blots were overlaid with the receptor construct CEACAM1-Fc or the affinity purified anti-UspA1 peptide antibodies. A small fragment reacting with the receptor also bound to the anti-UspA1-specific antibodies (FIG. 5).

(b) Localization of CEACAM Binding Domain of UspA 1 of *M. catarrhalis* Strain MX2

MX2 bacterial suspensions were treated with Trypsin at 1 mg/ml for 10 minutes at 37° C.

Figure 7:
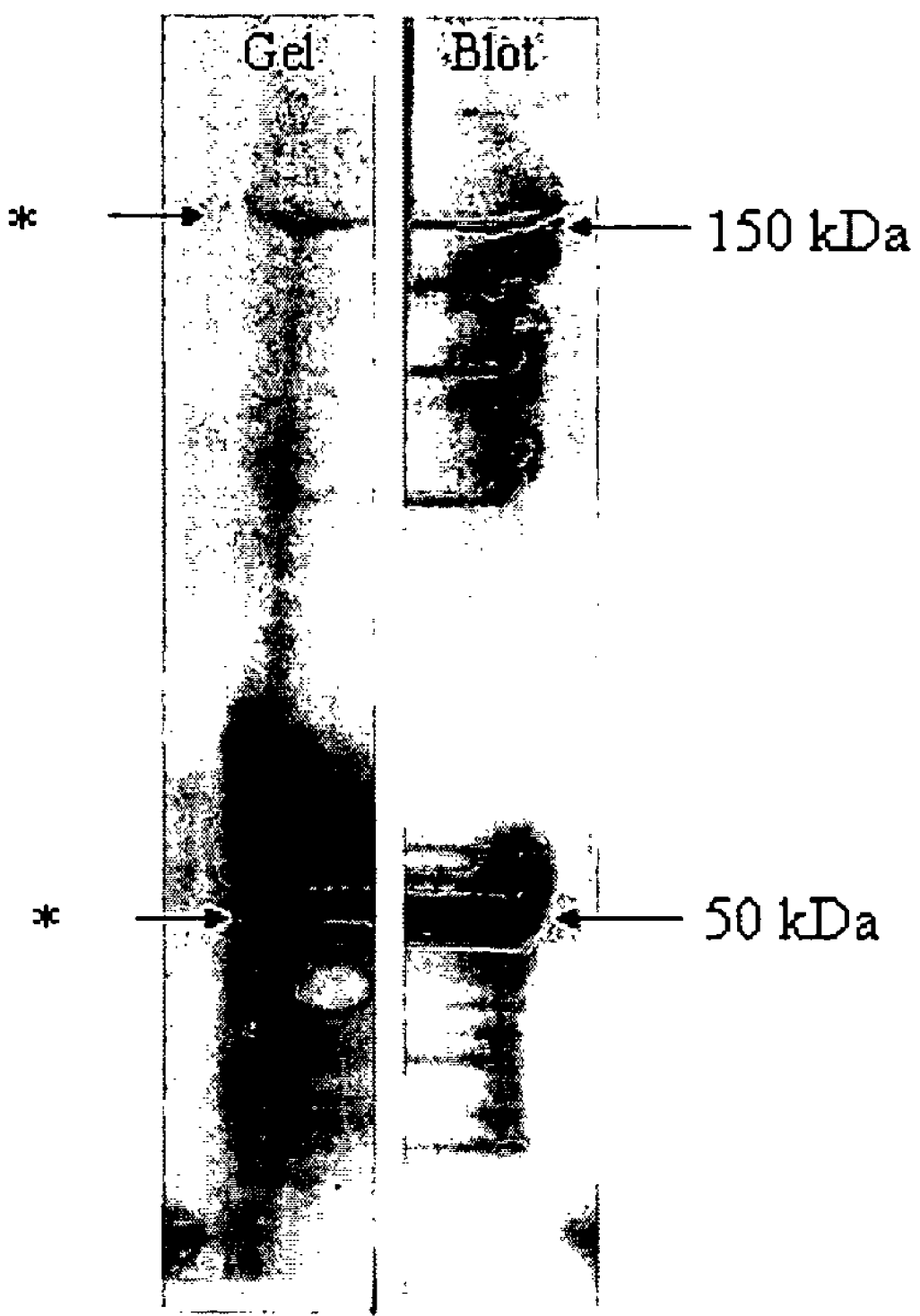

The trypsinized sample was run on an SDS-PAGE gel. After staining, the 50 kDa region was electroeluted overnight. Electroeluted protein was freeze dried and resuspended in buffer and applied to a second gel. Part of the gel was blotted onto nitrocellulose and peptide bands reacting with CEACAM were identified by Western blotting overlay using CEACAM1-Fc. (FIG. 7).

Peptide bands corresponding to circa. 50 kDa and circa. 150 kDa peptides were subjected to N-terminal sequencing. The N-terminal sequences were ALESNVEEGL (SEQ ID NO:4) (c. 50 kDa peptide) and ALESNV (SEQ ID NO:7) (c. 150 kDa peptide). The 150 kDa protein is apparently a trimer of the 50 kDa protein as they have the same N-terminal sequence. The N-terminal sequence of this peptide of MX2 UspA1 is shown in FIG. 8.

(c) Recombinant Peptide

The N-terminal recombinant MX2 peptide that was constructed consisting of amino acids 1 to 449 of the sequence shown in FIG. 6 does not bind CEACAM. This further indicates that the c. 50 kDa tryptic peptide consisting of amino acids 463 to 863 of the sequence shown in FIG. 8, having the N-terminal sequence ALESNVEEGL (SEQ ID NO:4) contains the CEACAM-binding domain.

EXAMPLE 2

Identification of Receptor Binding Domains on Multiple Virulence Determinants of Mucosal Pathogens

*N. meningitidis* and *H. influenzae* target human CEACAM molecules via ligands that bind to overlapping sites on CEACAM. The Mx ligand/s of the present invention also target the N domain. These observations point to an exciting possibility that similar features on ligands of several mucosal pathogens may be involved in receptor targeting.

Because Nm and Hi interactions with CEACAMs are affected by the structural features of the surface expressed variable domains, this suggests that they may contain similar crucial amino acids in a spatial configuration that are able to bind to the receptor and these may be conserved in otherwise variable proteins. Indeed our studies and those of others suggest that the two hyper-variable loops of Opa (HV1 and HV2) may be involved in CEACAM targeting [9,18]. One powerful technique that can identify possible determinants of interactions between ligands and receptors is phage display, which can be used to identify mimotopes (random sequences to mimic the binding domains)[19] as well as aptamers (sequences more closely related to the original structure that inhibit ligand binding) [20].

The current invention also makes it highly feasible that the Mx ligand domain that binds CEACAMs will act as a mimic for other CEACAM-binding mucosal pathogens and the structural features of this ligand will help identify the salient features required in Nm and Hi ligands for CEACAM N-domain targeting. Antibodies to the Mx domain could have the potential of identifying other ligands that have the capacity to target the same, similar or closely positioned region of the receptor.

Identification of the minimal CEACAM1 binding domain of MX2 UspA1 is being undertaken using known methods of protein engineering and recombinant DNA technology. Recombinant peptides can be screened in vitro by receptor overlay assays described above to detect the domain of MX2 that binds to the receptor. His-Tagged peptides can be separated on a nickel column, His-Tag cleaved as required and used for immunising rabbits and mice to obtain antibodies for further investigations.

A peptide of suitable length for biological applications may be determined by examining immunological stimulatory properties as well other functions such as blocking of receptor binding.

EXAMPLE 3

Salient Features of the Receptor Required for Ligand Interactions

Since the N-domain of CEACAM is sufficient for the interactions of Opa proteins, the present inventors are using phage display technique also to investigate adhesive epitopes of the CEACAM N-domain. The knowledge of the ligand-binding region/s on the receptor, which has been studied by the present inventors by alanine scanning mutagenesis of the receptor[9] has facilitated this study. In this case also, a ligand overlay assay is available for biopanning (affinity concentration) of chimeric phages that bear receptor sequences.

Receptor analogues have the potential to block multiple strains independently of the Opa type produced since our studies have already shown that despite their antigenic variation, distinct Opa proteins require common features on the receptor for primary adhesion[9]. It is also of interest to note that CEA antigens are shed from the gut mucosa and may block adhesion of *E. coli* strains also known to target CEACAMs. This has been proposed as a mechanism of innate immunity vs. enteric pathogens. [12] Thus these receptor analogues act as therapeutic agents.

EXAMPLE 4

Production of Recombinant CEACAM-binding *Moraxella catarrhalis* UspA1 Peptides

Summary

Figure 9:
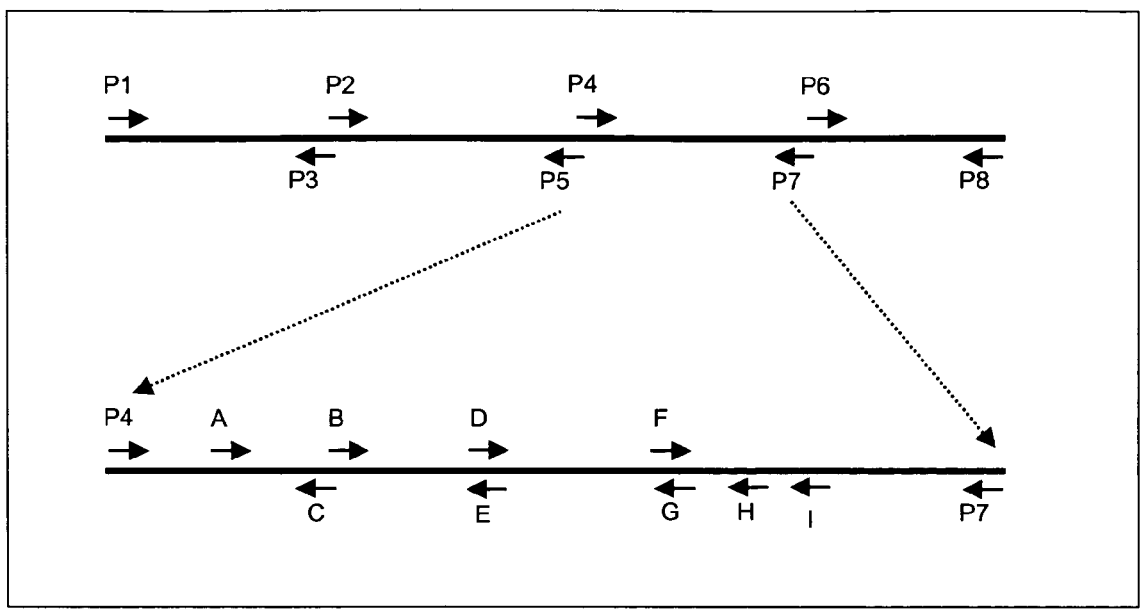

PCR amplification of several fragments along the length of UspA 1 was carried out using the primers shown in FIG. 9. Recombinant peptides were obtained as described below. In the first round, it was found that the recombinant peptide that bound to CEACAM1 was encoded by DNA amplified by primers P4 and P8 but not that encoded by region between P1 and P5. Further, recombinant P4-P7 bound CEACAM1 but not P6-P8. Additional primers were used within P4 and P7 region. Region D-7 retained CEACAM-binding. The sequence of fragment 4-7 is shown in FIG. 10.

Figure 11:
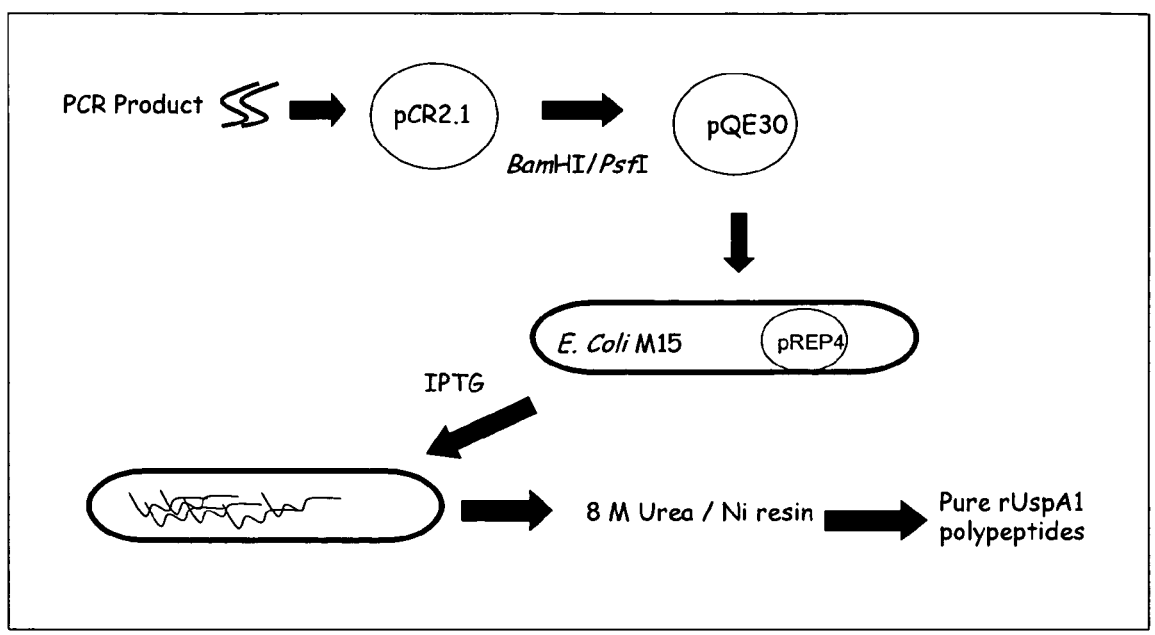
FIG. 11 is a diagram showing the general cloning, expression and purification strategy for recombinant UspA1 peptides, as exemplified by the pQE30 system.

General Cloning, Expression and Purification Strategy for Recombinant UspA1 peptides The UspA1 fragment 1-5 was produced using the pBAD system. The required PCR products were TA cloned into pBAD vector and TOP10 *E. coli* strain was used for amplification. The rest of the procedure was as shown in FIG. 11 with the exception that pBAD was induced using arabinose. The fragment 4-7 was produced using both the pBAD and pQE30 (FIG. 11) systems with similar CEACAM-binding results. The rest of the fragments were produced using the strategy in FIG. 11.

Vector and the pQE30 Expression System

Figure 12:
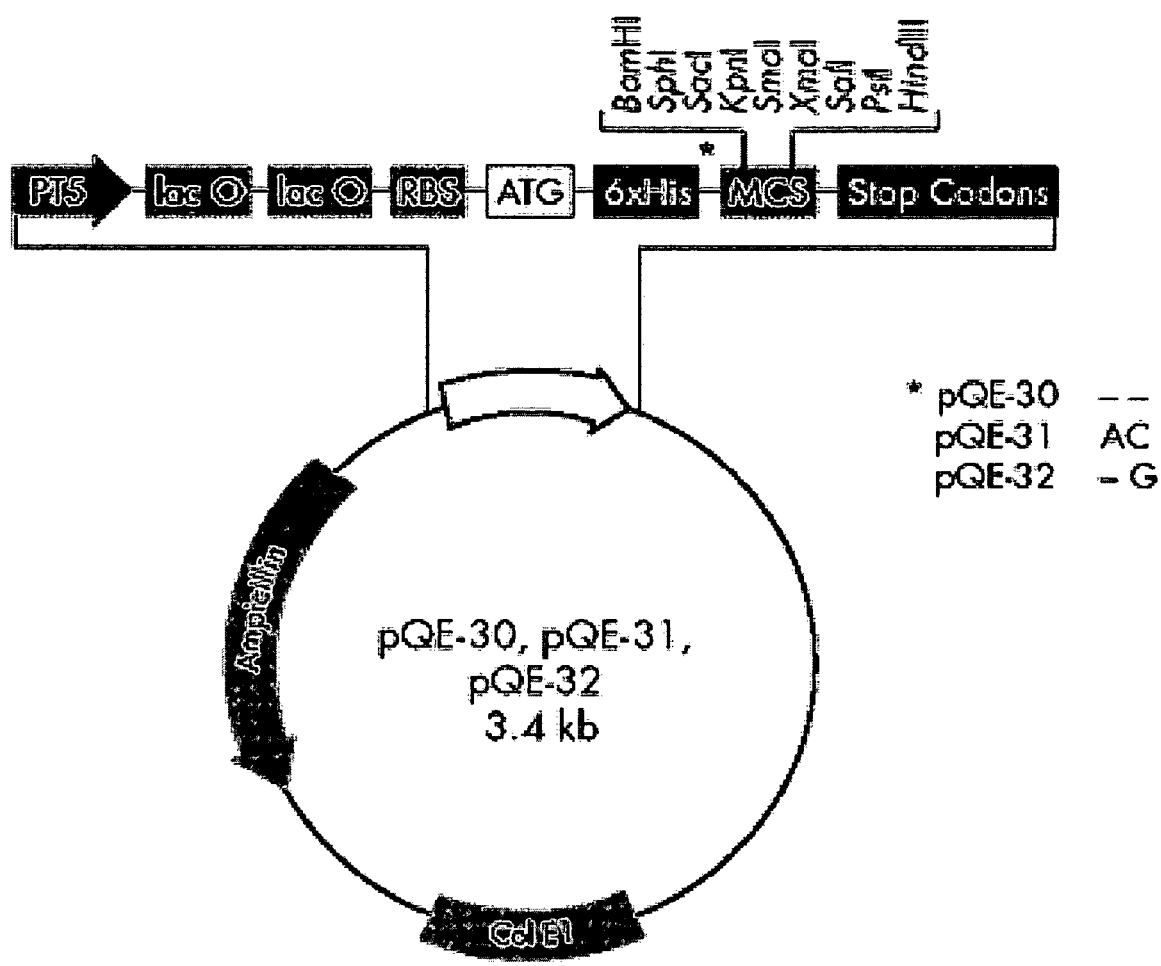
FIG. 12 is a map of the vector pQE30 (6xHis tap disclosed as SEQ ID NO: 40).

The vector pQE30 (FIG. 12) was used in conjunction with *E. coli* strain M15. M15 contains the plasmid pREP4 encoding a repressor, which restricts transcription of DNA cloned into pQE30. The addition of IPTG to a concentration of 1 mM prevents coding of this repressor and thus transcription of the cloned fragments in pQE30.

The Cloning Strategy

PCR amplimers were first ligated into pCR2.1. This provided a stable host from which the amplimer could be recovered by restriction digest (BamHI/PstI), ensuring that each end of the gene fragment was cut. pQE30 was similarly digested and recovered by gel purification, which also ensured that both restriction sites had been cut. Digested pQE30 and UspA1 amplimer were ligated overnight at 16° C. with T4 DNA ligase and transformed into $CaCl_2$ competent *E. coli* M15. Transformants were selected for on LB agar supplemented with ampicillin (100 μg/ml) and kanamycin (25 μg/ml). 4-8 colonies were picked and grown in LB broth with antibiotics. Bacteria from 3-4 ml of culture were collected by centrifugation and subjected to the alkaline-lysis miniprep method. Purified vector was digested as above to check for uspA1 insert. Bacteria containing pQE30 with a correct sized insert were grown in 50 ml. cultures and induced with IPTG (see below). Western blots were then used to screen for recombinant protein production. In addition, vectors were sequenced to determine that the insert was the correct region of DNA and to check for any sequence errors.

Expression and Purification

M15 containing pQE30/uspA1 constructs were grown in LB (supplemented with 100 μg/ml Ampicillin and 25 μg/ml Kanamycin) broth with shaking to OD600=0.5 before the addition of IPTG to a concentration of 1 mM. Cultures were incubated for a further 3-4 hours and bacteria recovered by centrifugation. Bacterial pellets were solubilized in buffer B (8M urea, 50 mM Tris, 10% ethanol, 2% Tween, 5 mM imidazole, pH 7) for 1-3 hrs and membrane material removed by centrifugation at 20,000 g for 20 min. Supernatants were incubated with nickel resin for 1-2 hrs on a rotary mixer, and passed through a polypropylene column. The retained resin was washed with 5-10 ml buffer B and bound protein eluted with 0.5 ml elutions of buffer B supplemented with 100 mM imidazole. Eluted proteins were checked by SDS-PAGE before dialysis to remove urea and other salts.

Recombinant Fragments

A: Fragments 1-5 and 4-8

These fragments produced by pBAD system showed that 1-5 did not bind CEACAM1 but 4-8 did.

B: Fragments 4-8,4-8T, 4-7 and 6-8 Produced using pQE30 System.

Fragment 4-8 was the first rUspA1 fragment produced and was found to bind CEACAM1 with a high affinity in blot-overlay assays. In addition to the full-length 4-8 rUspA1 peptide, a smaller, truncated, protein was observed. This peptide (designated 4-T) also bound CEACAM1 and appeared to be expressed at lower levels than 4-8 (FIG. 13). Sequence analysis of pQE30/4-T found that a mismatch (CAA to TAA) led to a termination codon at residue Q624 (see FIG. 10).

Peptides 4-7 and 6-8 were produced in order to rule out the possibility that a second CEACAM binding site occurred in 6-8. As predicted from the 4-T peptide, 4-7 demonstrated CEACAM binding (FIG. 13) but 6-8 did not (FIG. 14).

C: Fragments D-8 and D-7 Produced by pQE30 System

Both rUspA1 fragments D-8 (FIG. 15) and D-7 (not shown) were found to bind CEACAM1.

Biological Activity of Recombinant Peptide 4-7

*M. catarrhalis* strain MX1 and *H. influenzae* strain Rd bind to Chinese Hamster Ovary (CHO) cells transfected with CEACAM1. Their binding can be blocked with *M. catarrhalis* UspA1 recombinant peptide 4-7 but not a control peptide (FIG. 17).

In a further experiment it was shown that recombinant peptide D-7 (but not recombinant 6-8 i.e. residues E659-K863 of UspA1 of MX2) inhibits binding of both homologous and heterologous strains to transfected CHO cells expressing CEACAM1 (FIG. 23). Following preincubation of cells with either no peptide (column 1), control peptide (2 µg.ml$^{-1}$; column 2), or D-7 (2 µg.ml$^{-1}$; column 3) bacteria were added and non-adherent bacteria removed by washing after 1 h incubation. Bacteria associated with cells were then detected using antisera raised against distinct strains and rhodamine conjugated secondary antibodies. Mx: *Moraxella catarrhalis*, Nm. *Neisseria meningitidis*; Hi: *Haemophilus influenzae*.

EXAMPLE 5

Characterization of CEACAM1-Binding Peptides

Peptide D-7 was found to be the strongest binding recombinant peptide. Therefore, region D-7 (142 amino acids; see FIG. 16) of MX2 contains the CEACAM1 binding information.

Truncated peptide 4-T (197 amino acids) retains weak binding (FIG. 13). Therefore region D-T may contain a region with CEACAM1 binding ability.

A single amino acid substitution, K 560 1, in D-7 was found to nearly abolish CEACAM1 binding.

Deletion of the region 571-632 in the peptide D-8 (D-8Δ) resulted in a loss of CEACAM1 binding.

Linear overlapping peptides spanning the D-T region (FIG. 19) were made and tested for their ability to bind CEACAM1. No binding to CEACAM1 was observed.

Circular Dichroism Spectroscopy

The peptide D-7 and the mutant D-7 (K 560 1) were analysed by circular dichroism (CD) spectroscopy. Circular dichroism spectra were obtained at room temperature using a Jobin-Yvon CD6 spectropolarimeter. Spectra of recombinant D-7 and D-7 (K 560I) at concentrations 0.1 mg/ml were measured in quartz cuvettes. All spectra are averages of 8 scans with relevant protein-free buffer spectra subtracted and were plotted using Excel (Microsoft Inc.).

The spectra obtained show that D-7 has an α-helical structure whereas D-7 (K 560I) adopts a random coil formation (FIG. 18). Without wishing to be bound by any particular theory, it is proposed that CEACAM1 binding of Mx UspA1 requires an α-helical based conformation, perhaps a coiled coil structure.

Summary

From the results described above, the inventors concluded that CEACAM1 binding of Mx UspA1 requires a region within D-7 in addition to an α-helical based conformation, perhaps a coiled coil structure.

The finding that the CEACAM1 binding domain of Mx UspA1 adopts an α-helical based conformation that is required for receptor binding is particularly interesting. Opa proteins require careful reconstitution for presentation of the CEACAM-binding domains which occur on different surface exposed loops. The present findings suggest that D-7 refolds spontaneously to provide the CEACAM-binding property. In D-7 the coiled structure provides a globular sub-unit structure with appropriate conformation for CEACAM1 binding. This advantageous property of the D-7 peptide means that the peptide, and derivatives, homologues or fragments thereof, could have particular utility as a sub-unit vaccine or therapeutic. Derivatives of the D-7 peptide having the required α-helical based conformation may be identified by the unique "fingerprint" circular dichroism spectrum.

EXAMPLE 6

Sequence Analysis

An alignment of the D-7 region of the amino acid sequences of the UspA1 proteins of ten strains of Mx is shown in FIG. 20.

Six out of ten strains are identical over the sequenced region. Strains MX3 and MX4 are 100% identical over the available sequence of the D-7 region and have overall identities 90.85% and 88.03% respectively, taking into account the N-terminal 13 and 17 amino acid residues for MX3 and MX4 respectively that have not been determined.

The remaining two strains TTA37 and O35E have deletions as shown (FIG. 20) which occur within the region D-T. Overall identity including the gaps in D-7 is 70.4% and 50% respectively. TTA37 is identical in the remaining region of 100 amino acids whereas O35E is identical in 71 out of 72 amino acids when aligned manually (FIG. 21). It is known that 035E does not bind to CEACAM1. TTA37 is not available for testing.

EXAMPLE 7

Adhesion Blocking Properties of D-7

Results

The potential of D-7 as an anti-adhesive agent effective against homologous and heterologous strains of Mx, Nm, Ng and Hi was first examined using the-soluble receptor. CEACAM1-Fc (CC1-Fc) was preincubated with D-7 prior to overlay of whole cell lysates of two Mx strains dotted onto nitrocellulose. Recombinant D-7 was shown to inhibit binding of CC1-Fc significantly to a heterologous strain MX1 and to the homologous strain MX2 in a dose dependent manner (FIG. 24 a). Inhibition was significant and appeared to reach a plateau above 0.01 µg. ml$^{-1}$. No such inhibition was displayed by the control peptide (D-8Δ), previously shown not to bind CEACAM1 (Example 5). Further, the inhibition of multiple bacterial strains was determined. The majority of the strains used represented clinical isolates of world-wide origins (see Methods). Significant and specific inhibition was displayed by D-7 but not D-8Δ (FIG. 24 b). The blocking effect of D-7 was then examined using Chinese Hamster Ovary (CHO) cells transfected with CEACAM1 (CHO-CEACAM1). As with the soluble receptor, an inhibition of binding of Mx, Nm and Hi to CHO-CEACAM1 cells was observed following preincubation with D-7 but not with the control peptide (FIGS. 25 a and b). The inhibition of bacterial binding to CHO-CEACAM1 cells was dose dependent and significant at or above 0.1 µg. ml$^{-1}$ for Mx and Hi and 0.2 µg. ml$^{-1}$ for Nm (FIG. 25 b). Near complete abrogation of bacterial binding to CHO-CEACAM1 was obtained at concentrations of c. 2 µg. ml$^{-1}$ (FIGS. 25 a and b). Values obtained for inhibition tentatively suggest an order of affinity for CEACAM interactions of the bacteria used in this study as Nm>Mx>Hi. Besides CEACAM1, N. meningitidis has been shown to target other members of the human CEACAM family, including epithelial CEA and CEACAM6 (NCA)[9], this is also the case with some Mx strains, Hi strains tend to target CEACAM1 as a preferred receptor (data not shown). Following preincubation with D-7 (2 µg. ml$^{-1}$), inhibition of Nm binding was observed to transfected HeLa cells expressing CEACAM1, 6 and CEA (FIG. 25 c).

The efficacy of D-7 was further tested using HeLa-CC1 H, a cell line generated to express high-levels of CEACAM1 to mimic, in part, a possible in vivo inflammation state of epithelial cells. High receptor density allows Opa-expressing bacteria to attach to target cells despite the presence of capsule[7]. Therefore, this model allowed us to also use a phenotype of Nm (h18.18) that may be found in vivo i.e. capsulate, piliated and expressing the outer-membrane proteins Opa as well as Opc[15,25]. First, binding of an Opa-deficient derivative of h 18.18 to HeLa-CC1H was tested and was found to be relatively low (10-20 bacteria per cell) and was due to the expression of pili. As expected, the adherence of h18.18 to HeLa-CC1 H was much enhanced (100-150 bacteria per cell) and despite the contribution of pili, cellular adhesion by h18.18 was considerably reduced by the prior or simultaneous treatment with D-7 (FIG. 25 d). In addition to the above, D-7 was tested on the human lung epithelial cell line A549, known to express CEACAMs[26]. This cell line was chosen since it also expresses receptors for other Mx ligands 27, thus the efficacy of the D-7 in reducing bacterial-load could be tested. In the presence of D-7 (2 µg. ml-1) but not D-8Δ, a dramatic decrease in interaction of Nm and Hi with A549 cells was observed (FIG. 25 e). Reduction in binding was observed for Mx strain also, and although in comparison relatively lower, it was nonetheless significant (FIG. 25 e).

Methods

Bacterial Isolates and Culture

Mx and Nm were grown on BHI agar supplemented with 10% heated horse blood whereas, Hi were grown on brain heart infusion (BHI) agar supplemented with Levinthal base. Ng strains were cultured on GC agar. All bacteria were cultured at 37° C. for up to 16 h in a 5% $CO_2$ incubator. Mx strains were clinical isolates obtained from cases of otitis media and COPD and represent isolates from several countries. Eagan, cl and fl are typable Hi with capsules of type b, c and f respectively, Rd is an acapsulate derivative of a type d strain. Strains A930065 and NT1 are NTHi. Strains A3, F2087, F3035 and F1947 are Hi biogroup aegyptius isolates. Nm isolates C751A, C751B and C751D are three distinct Opa expressing isolates of a serogroup A strain C751. Other isolates were of the following serogroups: PMC17(A), C311 and MC58 (B), and C114 (C) PMC2 (29E), PMC4 (W135) and PMC10 (Y). Ng isolates P9-13, 16 and 35 are intrastrain Opa variants of strain P9 and other clinical isolates were of worldwide origin. The majority of strains employed in the current study have been described further previously [10,26,28].

Antibodies

Anti-poly histidine mouse monoclonal antibody was purchased from Qiagen and used at 0.2 µg. ml$^{-1}$. Polyclonal antisera against Mx, Nm and Hi strains were raised in rabbits using standard protocols and whole cell lysates of multiple strains as antigens. Anti-UspA1 antibody (R38) used in this study has been described in Example 1 and 26 Polyclonal antiserum against D-7 was generated in rabbits by immunization with peptide bound to Ni-NTA resin (Qiagen; 100-200 µg of peptide per immunization). Complement was inactivated by heating the antisera at 56° C. for 30 min. Anti-D-7 antibodies were affinity purified using peptide D-7 coupled to AminoLink Plus column according to the manufacturer's protocol (Pierce).

Soluble Receptor Constructs & Cell Lines

Soluble CEACAM1-Fc and CHO cells transfected with CEACAM1 used in this study have been described previously [11,9]. HeLa cells expressing a range of CEACAM molecules were a gift from Professor Wolfgang Zimmerman (University of Munich, Germany) and Dr Scott Gray-Owen (University of Toronto, Canada) and-were grown-in RPMI 1640 containing 10% foetal calf serum (FCS). A549 human lung carcinoma cells (Flow laboratories) were cultured in F12 Ham medium containing 10% (FCS). HeLa cells expressing high levels of CEACAM were generated by using Tet-On™ (Clontech) gene expression system. The ceacaml gene was cloned into the pTRE-2hyg response plasmid (Clontech) and transformed into HeLa cells that contained the regulatory gene (Clontech) using Fugene-6 (Roche). Transfectants were selected using 400 µg. ml$^{-1}$ hygromycin. Those transfectants that were positive for CEACAM expression were selected using FACS and limiting dilution. HeLa-CC1H clone in the presence of 0.25 µg. ml$^{-1}$ doxycycline produced the highest levels of the receptor.

Receptor Overlay Assays

These experiments were based on a previously described method[9] with the following exceptions. For inhibition studies CEACAM1-Fc (0.1 µg. ml$^{-1}$) was preincubated with D-7 or control peptide (0.001-2 µg. ml$^{-1}$) for 1 h at RT. Blots were subsequently overlaid either with CEACAM1-Fc (0.1 µg. ml$^{-1}$) alone or preincubated with peptides as described. Alternatively blots were overlaid with purified rabbit anti-D-7 antibody (10 µg. ml$^{-1}$) for 1 h prior to overlay with receptor (0.1 µg. ml$^{-1}$). In either case, levels of receptor binding were determined by densitometric analysis using the NIH Scion Image program.

Inhibition of Bacterial Adherence to CEACAM Expressing Cells by Peptide D-7

Confluent monolayers of cells were pre-incubated with peptide D-7 or control peptide (0.1-2 µg. ml$^{-1}$) for 30-60 min at 37° C. in 199 medium with the addition of 2foetal bovine serum. Monolayers were examined following preincubation with peptide to ensure no deleterious effect on the cells had occurred. Subsequently, monolayers were incubated at a ratio of c. 100-200 bacteria per cell in 199 medium with the addition of 2% foetal bovine serum for 1 h at 37° C. Non-adherent bacteria were removed by washing 4 times with 199 medium and monolayers were then either treated for immunofluorescence detection or lysed with 1% saponin and dilutions of bacteria plated out for determination of colony forming units (cfu) as described previously [25]. For immunofluorescence detection, cells were fixed in absolute methanol for 10 min., washed and blocked with 1% bovine serum albumin in PBS containing 0.05% Tween for 1 h. The attached bacteria were detected using anti-bacterial antisera and rhodamine conjugated secondary antibodies. Numbers of bacteria adhering to HeLa-CEACAM expressing cells were obtained by direct counting using an Olympus IX70 microscope, with ×400 magnification. Mean values of bacteria bound were obtained after counting adherent bacteria to 20 cells chosen at random from duplicate experiments. Bacterial adherence to HeLa-CC1H was determined by cfu analysis as described above.

EXAMPLE 8

Anti D-7 Antibody Inhibits Mx-CEACAM1 Interactions

Results

Rabbit antisera generated against D-7 contained antibodies that were cross-reactive with UspA1 from several Mx strains in Western blot overlay of whole cell lysates (data not shown). No binding of anti-D-7 was observed to Nm Opa or Hi P5 by Western blotting using affinity purified antibodies (data not shown). Incubation of whole cell lysates of a range of Mx strains with anti-D-7 (10 µg. ml$^{-1}$) prior to CC1-Fc overlay resulted in a significant inhibition of the receptor binding with the majority of strains showing greater than 80% inhibition (FIG. 26). However, only low levels of inhibition were observed for strains of Hi, Nm and Ng in similar experiments. Thus antibodies against D-7 could offer protection against Mx infection whereas D-7 may serve as a more general antimicrobial peptide for a diverse range of CEACAM targeting bacteria.

EXAMPLE 9

Inhibition of Bacterial Adherence to CEACAM Expressing Human Endothelial Cells by Peptide D-7

In order to assess the effect of D-7 on endothelial cells, confluent monolayers of HMEC-1 cells were used. The human microvasular endothelial cells were preincubated with either D-7 or a recombinant control molecule (both at 1 µg.ml$^{-1}$) for 60 min. Bacteria (OpaD-expressing isolate of *N. meningitidis* strain C751) were then added at infection ratio of 100 bacteria per cell and incubated for 1 hr at 37° C. Following this time, non-adherent bacteria were removed by washing and the monolayer fixed in methanol for 10 min at room temperature. Adherent bacteria were detected by overlay with rabbit polyclonal antisera against *N. meningitidis* and subsequently anti-Rabbit TRITC conjugated secondary antibody.

The majority of the endothelial cells had up to 30 associated bacteria per cell in the absence of peptides. In the presence of the control peptide no obvious inhibition of bacterial binding was observed. However, in the presence of D-7, the binding was virtually abrogated with occasional cells having 1-2 bacteria attached (FIG. 27).

Thus D-7 is capable of inhibiting Opa-CEACAM mediated adhesion of *N. meningitidis* to endothelial cells as well as epithelial cells.

EXAMPLE 10

Conservation of the Sequence of Fragment "4-T" (Amino Acids 427-623 of MX2 UspA1) amongst known UspA1 Protein Sequences

TABLE II

Strains and sequences used

| GenBank accession number | Strain | Length (aa) |
|---|---|---|
| AAN84895 | P44 | 913 |
| AAB96359 | O35E | 832 |
| AAF40122 | TTA37 | 873 |
| AAF40118 | O12E | 922 |
| AAF36416 | O46E | 892 |
| AAD43469 | V1171 | 912 |
| AAD43467 | TTA24 | 941 |
| AAD43465 | ATCC25238 (MX2) | 863 |

A multiple alignment with all full length protein sequences was done to identify the corresponding fragment in sequences of other strains.

TABLE III

Location of corresponding fragment

| Strain | From aa | To aa | Length |
|---|---|---|---|
| ATCC25238 | 427 | 623 | 197 |
| O12E | 515 | 682 | 168 |
| O35E | 495 | 592 | 98 |
| O46E | 456 | 652 | 197 |
| P44 | 477 | 673 | 197 |
| TTA24 | 505 | 701 | 197 |
| TTA37 | 486 | 633 | 148 |
| V1171 | 476 | 672 | 197 |

The multiple alignment for these fragments is shown in FIG. 28. The associated identity percentages are shown below.

TABLE IV

Percentage sequence identity of fragments defined in Table III

| | O12E | O35E | O46E | P44 | TTA24 | TTA37 | V1171 |
|---|---|---|---|---|---|---|---|
| ATCC25238 | 95 | 85 | 96 | 99 | 96 | 97 | 97 |
| O12E | | 92 | 95 | 96 | 95 | 79 | 94 |
| O35E | | | 90 | 86 | 91 | 89 | 89 |
| O46E | | | | 97 | 98 | 98 | 98 |
| P44 | | | | | 97 | 97 | 97 |
| TTA24 | | | | | | 98 | 98 |
| TTA37 | | | | | | | 98 |

As shown in Example 6 for the region D-7, the above results indicate that the region 4-T is highly conserved among different strains, with sequence identity of 95% or more for all strains tested except O35E (85% identity). As previously noted, O35E does not bind to CEACAM. Accordingly, peptides comprising or consisting of conserved regions of sequence 4-T (427-623), as shown in FIG. 28, are preferred peptides according to the invention with utility for the treatment or prophylaxis of disease, in particular diseases where CEACAM receptors are implicated.

REFERENCES

1. Cartwright, K. et al. 1995. In *Meningococcal Disease*. John Wiley & Sons.
2. van Alphen, L. & van Ham, S. M. 1994. *Rev Med Microbiol* 5:245.
3. Foxwell, A. R. et al. 1998. *Microbiol Mol Biol Rev* 62:294.
4. van Alphen, L. et al. 1995. *Am J Respir Crit Care Med* 151:2094.
5. Karalus, R. et al. 2000. *Microbes & Infection* 2:5
6. Kraft, M. 2000. *Clin Chest Med* 21:301.
7. Virji, M. et al. 1996. *Mol Microbiol* 22:929.
8. Virji, M. et al. 1996. *Mol Microbiol* 22:941.
9. Virji, M. et al. 1999. *Mol Microbiol* 34:538.
10. Virji, M. et al. 2000. *Mol Microbiol* 36:784.
11. Hill, D. et al. 2001 *Mol Microbiol* 39: 850.
12. Hammarström, S. 1999 *Cancer Biol* 9:67.
13. Stephens, D. S. 1989. *Clin Microbiol Rev* 2:S 104.
14. Virji, M. et al. 1991. *Mol Microbiol* 5:1831.
15. Achtman, M. 1995 *Trends Microbiol* 3:186.
16. Merz, A. J. & So, M. 2000 *Annu Rev Cell Dev Biol* 16:423.
17. Woods, J. P. & Cannon, J. G. 1990 *Infect Immun* 58:569.
18. Wang, L-F & Yu, M. 1996 In *Methods Mol Biol* 66:269 (Morris, G. E. ed). Humana Press.
19. Colman-Lerner. 2000. *Trends Guide* p. 56 (Wilson, E. ed.).
20. Beauchemin, N., et al., 1999. *Exp Cell Res* 252: 243-249.
21. Boulton I. C. & Gray-Owen S. D. 2002. *Nat Immunol* 3(3):229-36.
22. Chen T. et al., 2001. *J Leukoc Biol* 70(2):335-40.
23. Lafontaine, E. R., et al., 2000. *J Bacteriol* 182: 1364-1373.
24. Virji, M. 2001. *Trends in Microbiology*, 9: 258-259.
25. Virji, M. et al. 1995. *Mol Microbiol* 18: 741-754.
26. Hill, D. J. & Virji, M. 2003. *Mol Microbiol* 48: 117-129.
27. Holm, M. M., et al. 2004. *Infect Immun* 72:1906-1913.
24. Virji, M. 2001. *Trends in Microbiology*, 9: 258-259.
25. Virji, M. et al. 1995. *Mol Microbiol* 18: 741-754.
26. Hill, D. J. & Virji, M. 2003. *Mol Microbiol* 48: 117-129.
27. Holm, M. M., et al. 2004. *Infect Immun* 72:1906-1913.
28. Virji, M. et al. 1990. *Microb Pathog* 9:441-450.
29. Langermann, S. et al. 1997. *Science* 276:607-611.
30. Ofek, I. et al. 2003. *FEMS Immunol Med Microbiol* 38:181-191.
31. Simon, P. M. et al. 1997. *Infect Immun* 65:750-757.
32. Idanpaan-Heikkili, I. et al. 1997. *J Infect Dis* 176:704-712.
33. Kelly, G. C. et al. 1999. *Nat Biotechnol* 17:42-47.
34. Gan, B. S. et al. 2002. *J Infect Dis* 185:1369-1372.
35. Reid, G. & Burton, J. 2002. *Microbes Infect* 4:319-324.
36. Pinyon, R. A. et al. 2004. *J Infect Dis* 189:1547-1555.
37. Reid, G. et al. 2001. *Trends Microbiol* 9:424-428.
38. Toleman, M. et al. 2002. *Cell Microbiol* 3:33-44.
39. Budt, M. et al. 2002. *Biol Chem* 383:803-812.

Incorporation by Reference

The contents of all references (including literature references, issued patents, published patent applications, and co-pending patent applications) cited throughout this application are hereby expressly incorporated herein in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

---

The invention claimed is:

1. An isolated ligand that consists of an amino acid sequence selected from the group consisting of residues 463 to 863, 527 to 623, 527 to 668, 527 to 863, 427 to 623, 427 to 668 and 427 to 863 of SEQ ID NO: 2 and that inhibits bacterial adhesion to CEACAM1 expressing cells in vitro.

2. A method of inhibiting bacterial adhesion comprising contacting a cell with the isolated ligand of claim 1 thereby inhibiting bacterial adhesion to the cell.

3. A fusion protein comprising an isolated ligand that consists of an amino acid sequence selected from the group consisting of residues 463 to 863, 527 to 623, 527 to 668, 527 to 863, 427 to 623, 427 to 668 and 427 to 863 of SEQ ID NO: 2 and that inhibits bacterial adhesion to CEACAM1 expressing cells in vitro.

4. A method of inhibiting bacterial adhesion comprising contacting a cell with the fusion protein of claim 3, thereby inhibiting bacterial adhesion to the cell.

* * * * *